United States Patent
Ke et al.

(10) Patent No.: US 12,221,414 B2
(45) Date of Patent: *Feb. 11, 2025

(54) QUATERNARY AMMONIUM SALT COMPOUND, PREPARATION METHOD THEREFOR AND USE THEREOF

(71) Applicant: WEST CHINA HOSPITAL, SICHUAN UNIVERSITY, Sichuan (CN)

(72) Inventors: Bowen Ke, Sichuan (CN); Jin Liu, Sichuan (CN); Wensheng Zhang, Sichuan (CN); Jun Yang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 844 days.

This patent is subject to a terminal disclaimer.

(21) Appl. No.: 17/427,521

(22) PCT Filed: Jan. 21, 2020

(86) PCT No.: PCT/CN2020/073387
§ 371 (c)(1),
(2) Date: Jul. 30, 2021

(87) PCT Pub. No.: WO2020/156359
PCT Pub. Date: Aug. 6, 2020

(65) Prior Publication Data
US 2022/0135526 A1    May 5, 2022

(30) Foreign Application Priority Data
Feb. 1, 2019 (CN) .......................... 201910102803.0

(51) Int. Cl.
| | | |
|---|---|---|
| C07D 211/60 | (2006.01) | |
| C07D 205/04 | (2006.01) | |
| C07D 207/16 | (2006.01) | |
| C07D 223/06 | (2006.01) | |
| C07D 413/06 | (2006.01) | |
| C07D 413/12 | (2006.01) | |

(52) U.S. Cl.
CPC .......... C07D 211/60 (2013.01); C07D 205/04 (2013.01); C07D 207/16 (2013.01); C07D 223/06 (2013.01); C07D 413/06 (2013.01); C07D 413/12 (2013.01)

(58) Field of Classification Search
CPC .. C07D 213/20; C07D 211/60; C07D 205/04; C07D 207/16; C07D 413/06
See application file for complete search history.

(56) References Cited

U.S. PATENT DOCUMENTS 11,697,639 B2 * 7/2023 Liu ................. C07C 229/16
                                            514/210.17

FOREIGN PATENT DOCUMENTS

| CN | 1295558 A | 5/2001 |
| CN | 103601650 A | 2/2014 |
| CN | 110156665 A | 8/2019 |

OTHER PUBLICATIONS

Narahashi ( Nature vol. 223 pp. 748-749 published 1969) (Year: 1969).*
Courtney Kenneth R., Mechanism inhibition of frequency-dependent of sodium currents in frog myelinated nerve by the lidocaine derivative gea 968-1, Journal of pharmacology and experimental therapeutics. 1975, vol. 195, No. 2:225-236.
Ries, Craig R. et al.; QX-314 Produces Long-lasting Local Anesthesia Modulated by Transient Receptor Potential Vanilloid Receptors in Mice, Anesthesiology, Jul. 2009; vol. 111, No. 1:122-126.
Kohane, Daniel S.; Prolonged sensory-selective nerve blockade, PNAS. Feb. 23, 2010; vol. 107, No. 8, pp. 3740-3745.

* cited by examiner

Primary Examiner — Theodore R. Howell
Assistant Examiner — George W Kosturko
(74) Attorney, Agent, or Firm — NKL Law; Allen Xue

(57) ABSTRACT

A quaternary ammonium salt compound of formula I is fast-acting and has a long-term local anaesthetic effect after a single administration, the sensory nerve block time being longer than the motor nerve block time, has both a long-acting local anaesthetic effect and a selective local anaesthetic effect, and also significantly reduces the side effects of quaternary ammonium salt compounds with the structural features of surfactants and is highly safe; thus, the compound of formula I and the pharmaceutically acceptable salt thereof can be used for the preparation of saft drugs having a long-term local anaesthetic effect and a selective local anaesthetic effect

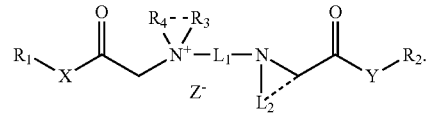

Formula I

12 Claims, No Drawings

QUATERNARY AMMONIUM SALT COMPOUND, PREPARATION METHOD THEREFOR AND USE THEREOF

TECHNICAL FIELD

The present invention belongs to the field of chemical medicine, and specifically relates to a quaternary ammonium salt compound, as well as a preparative method and a use thereof.

BACKGROUND TECHNOLOGY

Local anesthetics is a class of drugs that can reversibly block the occurrence and transmission of sensory nerve impulses in the administration area. Under the condition that animals or humans are waking and conscious, it can locally and reversibly block the generation and signal conduction of sensory nerve impulse, resulting in the temporary sensory loss in the innervated area, and thereby reversibly causing the loss of local tissue pain. Generally, the effect of local anesthetics is limited to the administration site and disappears rapidly as the drug diffuses from the administration site. Local anesthetics block the generation of action potentials and the conduction of nerve impulses by directly inhibiting the related ion channels in nerve cells and fiber membranes, thereby producing local anesthesia. Currently, the well-known action mechanism for local anesthetics is blocking voltage-gated $Na^+$ channels in nerve cell membranes, inhibiting nerve impulses, thereby producing local anesthesia.

The local anesthetics currently used in clinical practice are all hydrophobic compounds without electric charge, and they can easily enter nerve cells through cell membranes by diffusion and permeation, to reach the blocking site of sodium channels, and thereby interrupt the excitability of neurons by blocking sodium channels. In fact, although these local anesthetic molecules can easily enter nerve cells by diffusion to exert their actions, they also easily diffuse rapidly from the drug delivery site by diffusion, thereby escaping from nerve cells and resulting in that the local anesthetic effect cannot be kept for a long time. Even if the dosage is increased, the local anesthesia time can only be prolonged to a certain extent. These local anesthetic drugs cannot realize the ideal effect of long-time local anesthesia. At present, most of the local anesthetics commonly used in clinical have an action time of less than 4 hours. Because traditional local anesthetics last for a short period of time, analgesic pumps have to be used to maintain nerve block. The use of catheters in the spinal canal, nerve roots, and subcutaneous locations has greatly increased medical costs and the incidence of infection.

On the other hand, traditional local anesthetics do not have specific selectivity for nerve blocking. They block a variety of nerve fibers extensively during use, and affect various nerve functions such as sensation, pain, movement, and sympathetic nerves. This pharmacological feature greatly limits the wide application of local anesthetics in clinical practice. For example, early functional exercise and rehabilitation of patients after knee replacement is particularly important, however, there are no drugs that selectively block pain in the current local anesthetics. Most of surgical patients who use local anesthetics experience the motor nerves being blocked, unable to restore motor function, that limits postoperative rehabilitation. The study on local anesthetics urgently needs to introduce new research ideas and develop long-acting local anesthetics that selectively block sensory function, without affecting motor function, to meet clinical requirements.

The chemical structure of traditional local anesthetics generally contains at least one or more non-amide tertiary N atoms. When N is substituted, the corresponding quaternary ammonium compound will be obtained. The molecular structure of the quaternary ammonium compound has a positive charge, and the ability to penetrate the cell membrane is significantly reduced. For example, once the tertiary amine N atom in lidocaine is substituted with ethyl, a quaternary ammonium compound called QX-314 will be obtained. Similar to QX-314, QX-222 is also another quaternary ammonium salt having similar structure. Because the structures of QX-314 and QX-222 have positive charges, they cannot pass through cell membranes under normal conditions, and thus cannot quickly produce local anesthesia. But once it passes through the cell membrane, it can significantly inhibit sodium ion channels in nerve cells, resulting in a lasting local anesthetic effect (Courtney K R. *J Pharmacol Exp Ther.* 1975, 195:225-236). Current research has found that QX-314 can easily enter nerve cells through the activation of TRPV1 channel with the assistance of capsaicin (transient receptor potential channel vanilloid subtype 1 agonist, i.e. TRPV1 Agonist), producing a long-time nerve block (Craig R. Ries. *Anesthesiology.* 2009; 111:122-126). However, the strong irritation of capsaicin makes it difficult to have application prospects.

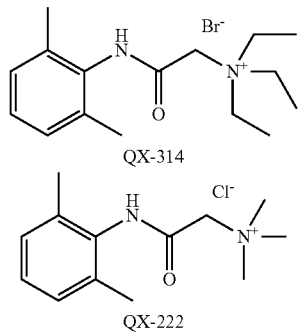

QX-314

QX-222

Studies have further shown that the combination of QX314 and local anesthetics clinically used such as bupivacaine and lidocaine can quickly produce anesthesia and avoid the irritation of capsaicin. However, the synergistic use of above drugs still cannot achieve the expected effect of local anesthesia. With the addition of surfactants, it can also help QX314 enter the cell membrane and cause local anesthesia for more than 8 hours (Daniel S. Kohane, *PNAS.* 2010; 107: 3745-3750). The current research has indicated that QX314 has some safety issues, which are mainly manifested as local nerve damage, and the death of experimental animals during intrathecal injection and so on. Based on QX-314, a series of long-chain compounds with surfactant structure have been developed, and they can realize a longer local anesthetic effect to a certain extent. However, since this kind of compounds have a surfactant-like structure, although they can produce long-acting effect at a certain degree, they will also cause serious muscle and nerve damage in local injection site, with poor safety. Meanwhile, similar compounds that have been reported so far do not have selective local anesthesia, and cannot meet clinical needs.

Therefore, whether QX314 is used alone, or it is used in combination with other active drugs, or long-chain compounds of QX314 have structural characteristics of surfactant, have the disadvantages of poor safety and poor selectivity for local anesthesia.

Therefore, it is of great significance to study a local anesthetic with fast onset, long-time action, good safety, and specific selectivity.

CONTENT OF THE INVENTION

In view of above-mentioned problems, the present invention provides a new class of quaternary ammonium compounds, which have both long-acting and selective local anesthesia (the block time of sensory nerve is longer than that of motor nerve), and the compound has the advantages of fast onset, long-time local anesthetic action, good local anesthetic selectivity, less nerve damage, and high safety, compared with the existing QX314, QX314 composition, and the long-chain compound with surfactant structure characteristics.

The present invention provides compound of formula I, or a pharmaceutically acceptable salt thereof, or a stereoisomer thereof, or a solvate thereof, or a prodrug thereof, or a metabolite thereof:

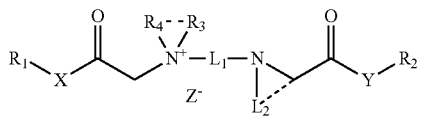

Formula I
wherein,
each of X and Y is independently selected from O or $NR_{10}$, wherein $R_{10}$ is selected from the group consisting of H, deuterium, or $C_1$-$C_4$ alkyl;
$Z^-$ is a pharmaceutically acceptable anion;
$R_1$ is selected from $n_1$ $R_{11}$-substituted aryls;
$R_2$ is selected from $n_1'$ $R_{11}'$-substituted aryls;
wherein, $n_1$ and $n_1'$ are each independently selected from an integer of 0 to 5, and $R_{11}$ and $R_{11}'$ are each independently selected from the group consisting of deuterium, $C_1$-$C_4$ alkyl, $C_1$-$C_4$ alkoxy, halogen, nitro, cyano, hydroxyl, carboxyl, and amino;
when the dotted line between $R_3$ and $R_4$ in Formula I is none, $R_3$ is selected from substituted $C_1$-$C_{10}$ alkyl or unsubstituted $C_5$-$C_{10}$ alkyl, and $R_4$ is independently selected from substituted or unsubstituted $C_1$-$C_{10}$ alkyl, wherein said substituent is deuterium, substituted or unsubstituted $C_1$-$C_4$ alkoxy, halogen, nitro, cyano, hydroxyl, carboxy, amino, ester, $C_1$-$C_6$ alkylthio, mercapto; the substituent of said alkoxy is hydroxyl;
when the dotted line between $R_3$ and $R_4$ in formula I is a bond, $R_3$ and $R_4$ are independently selected from substituted or unsubstituted $C_1$-$C_4$ alkylenes, and the substituent is $C_1$-$C_3$ alkyls; wherein, the main chain of the alkylene contains 0~4 heteroatoms, and the heteroatom is selected from O, S, and NR12, wherein said $R_{12}$ is selected from hydrogen, deuterium, and $C_1$-$C_4$ alkyls;
$L_1$ is selected from substituted or unsubstituted $C_1$-$C_{14}$ alkylenes; wherein the main chain of the alkylene contains 0~4 heteroatoms, and the heteroatom is selected from O, S, and $NR_{12}$, wherein said $R_{12}$ is selected from the group consisting of hydrogen, deuterium, $C_1$-$C_4$ alkyl, and $C_1$-$C_4$ alkoxy; the substituent is deuterium, $C_1$-$C_4$ alkyl, $C_1$-$C_4$ alkoxy, and halogen;
In formula I, the dotted line of $L_2$ is a bond, and $L_2$ is selected from the group consisting of substituted or unsubstituted $C_1$-$C_8$ alkylenes, and the substituent is deuterium, $C_1$-$C_4$ alkyls, $C_1$-$C_4$ alkoxys, and halogen.

Further,
each of X and Y is independently selected from NH or $NCH_3$;
$Z^-$ is $Br^-$, $Cl^-$, and sulfonate;
$R_1$ is selected from $n_1$ $R_{11}$-substituted aryls;
$R_2$ is selected from $n_1'$ $R_{11}'$-substituted aryls;
wherein, each of $n_1$ and $n_1'$ is independently selected from an integer of 0 to 5, and each of Ru and $R_{11}'$ is independently selected from the group consisting of deuterium, $C_1$-$C_4$ alkyl, $C_1$-$C_4$ alkoxy, halogen, nitro, cyano, hydroxyl;
when the dotted line between $R_3$ and $R_4$ in Formula I is none, $R_3$ is selected from substituted $C_1$-$C_{10}$ alkyl or unsubstituted $C_5$-$C_{10}$ alkyl, and $R_4$ is independently selected from substituted or unsubstituted $C_1$-$C_{10}$ alkyl, wherein said substituent is deuterium, substituted or unsubstituted $C_1$-$C_4$ alkoxy, hydroxyl, carboxy, $C_2$-$C_5$ alkylthio, mercapto; the substituent of said alkoxy is hydroxyl;
when the dotted line between $R_3$ and $R_4$ in formula I is a bond, $R_3$ and $R_4$ are independently selected from $C_1$-$C_4$ alkylenes, wherein the main chain of the alkylene contains 0-2 heteroatoms, and the heteroatom is 0;
$L_1$ is selected from $C_3$-$C_{14}$ alkylenes; wherein the substituent is alkyl, and the main chain of the alkylene contains 0-2 heteroatoms, and the heteroatom is selected from O and S;
In formula I, the dotted line of $L_2$ is a bond, and $L_2$ is selected from $C_1$-$C_6$ alkylenes.

Further,
each of X and Y is independently selected from NH or $NCH_3$;
$Z^-$ is $Br^-$, $Cl^-$, and sulfonate;
$R_1$ is selected from $n_1$ $R_{11}$-substituted aryls;
$R_2$ is selected from $n_1'$ $R_{11}'$-substituted aryls;
wherein, each of $n_1$ and $n_1'$ is independently selected from an integer of 2 to 3, as well as $R_{11}$ and $R_{11}'$ are methyl, propyl, methoxy, hydroxy, nitro, cyano, and halogen;
when the dotted line between $R_3$ and $R_4$ in Formula I is none, $R_3$ is selected from substituted $C_1$-$C_8$ alkyl or unsubstituted $C_5$-$C_{10}$ alkyl, and $R_4$ is independently selected from substituted or unsubstituted $C_1$-$C_{10}$ alkyl, as well as said substituent is deuterium, substituted or unsubstituted $C_1$-$C_3$ alkoxy, hydroxyl, carboxy, $C_2$-$C_5$ alkylthio, mercapto; the substituent of said alkoxy is hydroxyl;
when the dotted line between $R_3$ and $R_4$ in formula I is a bond, $R_3$ and $R_4$ are independently selected from substituted or unsubstituted $C_2$-$C_3$ alkylenes, wherein the substituent is $C_1$ alkyl, and the main chain of the alkylene contains 0~1 heteroatoms, and the heteroatom is O; $L_1$ is selected from unsubstituted $C_3$-$C_{14}$ alkylenes; wherein the main chain of the alkylene contains 0~2 heteroatoms, and the heteroatom is selected from O and S;
In formula I, the dotted line of $L_2$ is a bond, and $L_2$ is selected from unsubstituted $C_1$-$C_6$ alkylenes.

Further,
each of X and Y is independently selected from NH;
$Z^-$ is $Br^-$;
$R_1$ is selected from $n_1$ $R_{11}$-substituted aryls;
$R_2$ is selected from $n_1'$ $R_{11}'$-substituted aryls;

wherein, each of $n_1$ and $n_1'$ is independently selected from an integer of 2 to 3, as well as $R_{11}$ and $R_{11}'$ are methyl;

when the dotted line between $R_3$ and $R_4$ in Formula I is none, $R_3$ is selected from substituted $C_1$-$C_8$ alkyl or unsubstituted $C_5$-$C_{10}$ alkyl; said substituent is deuterium, substituted or unsubstituted $C_1$-$C_3$ alkoxy, hydroxyl, carboxy, $C_2$-$C_3$ alkylthio, mercapto; the substituent of said alkoxy is hydroxyl;

when the dotted line between $R_3$ and $R_4$ in formula I is a bond, $R_3$ and $R_4$ are independently selected from unsubstituted $C_2$-$C_3$ alkylenes; wherein the main chain of the alkylene contains one heteroatom, and the heteroatom is O;

$L_1$ is selected from unsubstituted $C_3$-$C_{14}$ alkylenes; wherein the main chain of the alkylene contains one heteroatom, and the heteroatom is selected from O and S;

In formula I, the dotted line of $L_2$ is a bond, and $L_2$ is selected from unsubstituted $C_2$-$C_6$ alkylenes.

Further, said compound is as shown in formula II:

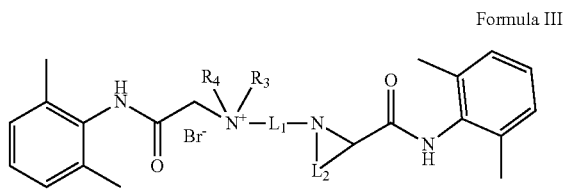

Formula II wherein, each of X and Y is independently selected from NH or $NCH_3$;

each of $n_1$ and $n_1'$ is independently selected from an integer of 2 to 3, as well as $R_{11}$ and $R_{11}'$ are methyl, propyl, methoxy, hydroxy, nitro, cyano, and halogen;

$R_3$ is selected from substituted $C_1$-$C_8$ alkyl or unsubstituted $C_5$-$C_{10}$ alkyl; $R_4$ is independently selected from substituted or unsubstituted $C_1$-$C_{10}$ alkyl; the substituent of said alkyl is deuterium, substituted or unsubstituted $C_1$-$C_3$ alkoxy, hydroxyl, carboxy, $C_2$-$C_5$ alkylthio, mercapto; the substituent of said alkoxy is hydroxyl;

$L_1$ is selected from unsubstituted $C_3$-$C_{14}$ alkylenes; wherein the main chain of the alkylene contains 0, 1 or 2 heteroatoms, and the heteroatom is selected from O and S;

$L_2$ is selected from unsubstituted $C_2$-$C_6$ alkylenes.

Further, said compound is as shown in formula III:

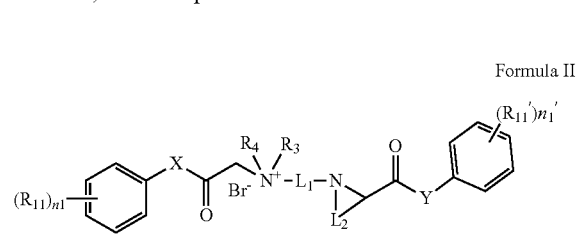

Formula III wherein, $R_3$ is selected from substituted $C_1$-$C_5$ alkyl; $R_4$ is independently selected from substituted or unsubstituted $C_1$-$C_5$ alkyl; the substituent of said alkyl is hydroxyl;

$L_1$ is selected from unsubstituted $C_3$-$C_6$ alkylenes;

$L_2$ is selected from unsubstituted $C_4$ alkylenes.

Further, said compound is as shown in formula IV:

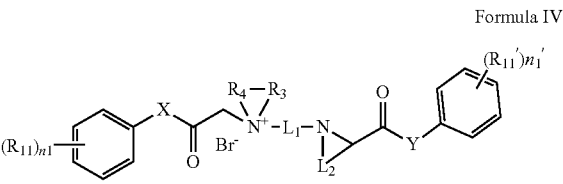

Formula IV wherein, each of X and Y is independently selected from NH;

each of $n_1$ and $n_1'$ is independently selected from an integer of 2 to 3; $R_{11}$ and $R_{11}'$ are methyl; $R_3$ and $R_4$ are independently selected from substituted or unsubstituted $C_2$-$C_3$ alkylenes; wherein said substituent is $C_1$ alkyl, as well as the main chain of the alkylene contains one heteroatom, and the heteroatom is O;

$L_1$ is selected from unsubstituted $C_3$-$C_{14}$ alkylenes; wherein the main chain of the alkylene contains 0 or 1 heteroatom, and the heteroatom is selected from O and S;

$L_2$ is selected from unsubstituted $C_2$-$C_6$ alkylenes.

Further, the structure of the compound is one of the followings:

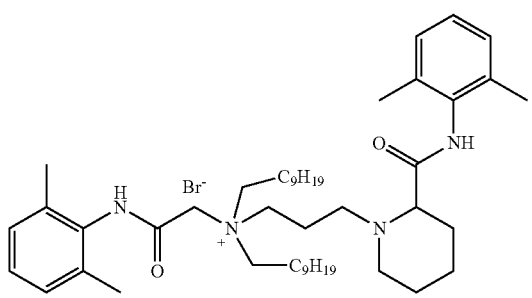

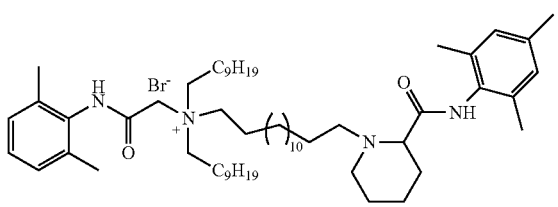

1
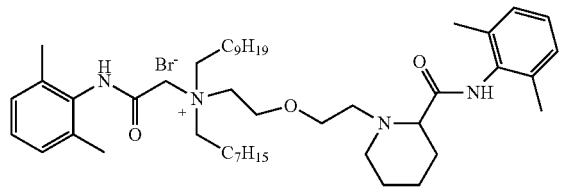
2
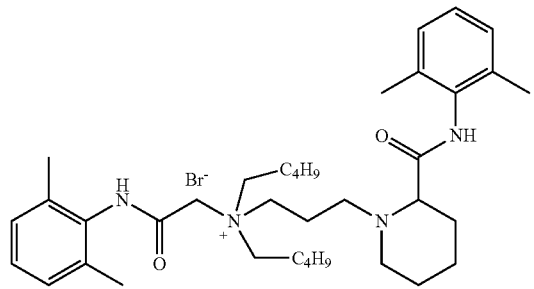
3
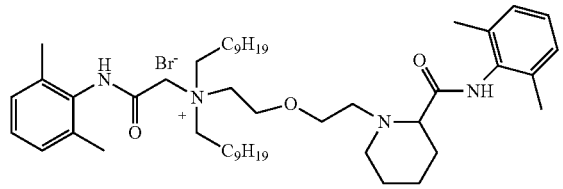
4
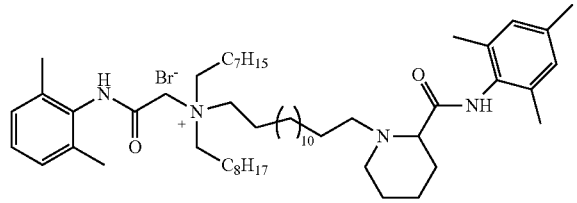
5
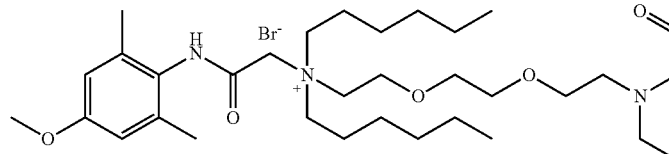
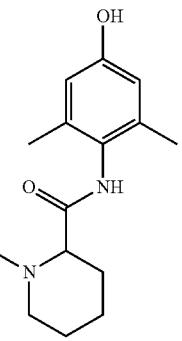
6
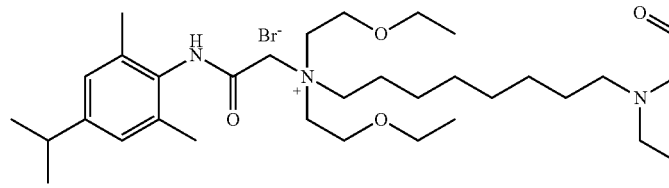
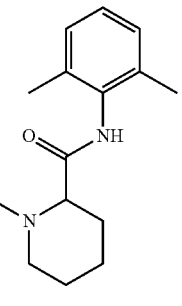
7
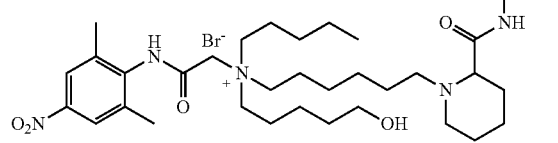
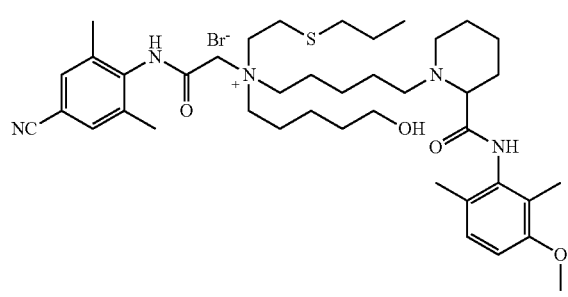

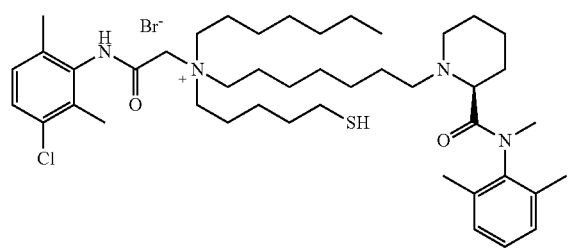
8
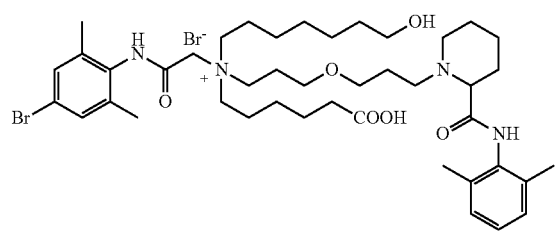
9
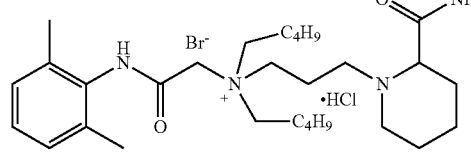
10
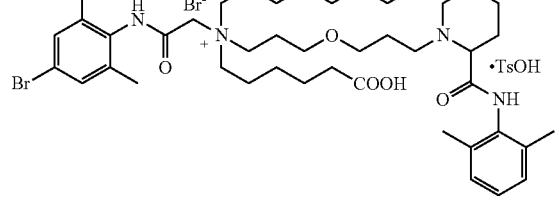
11
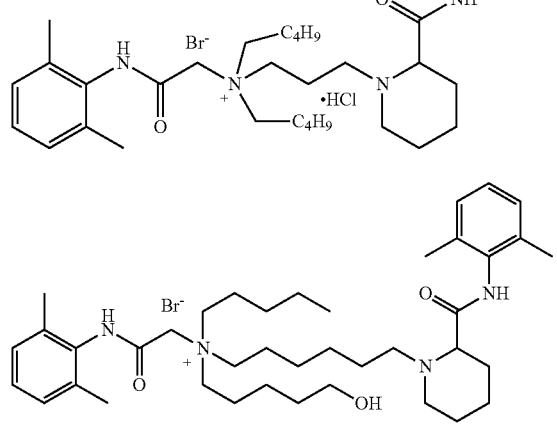
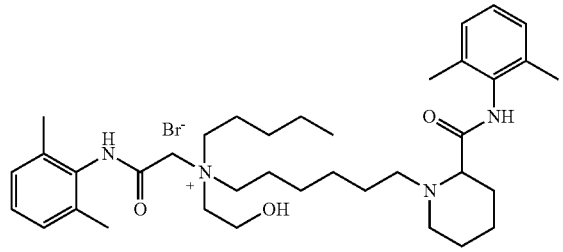
13
12
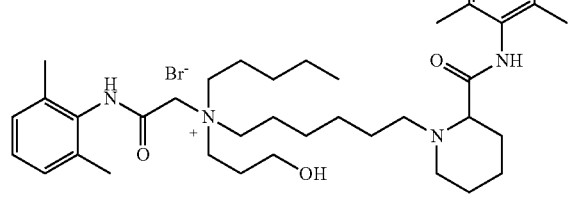
14
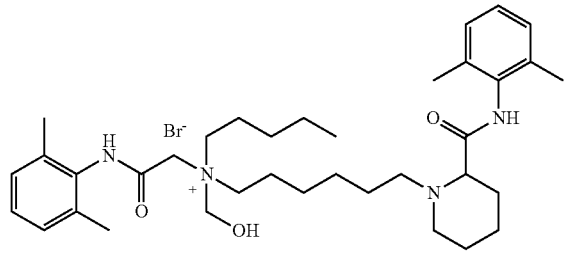
15
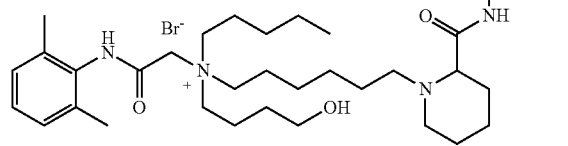
16
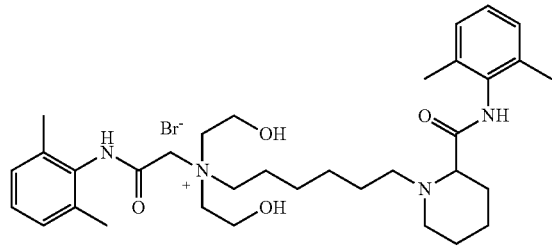
17
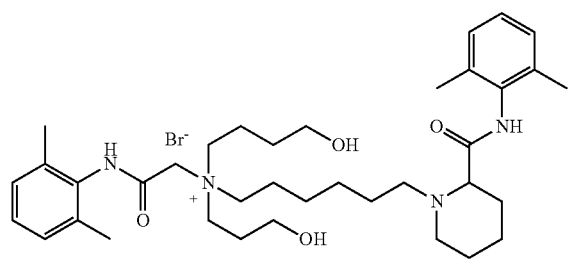
18
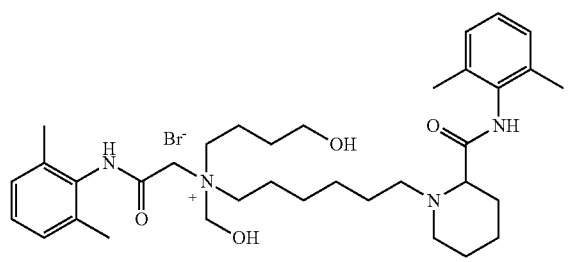
19

-continued
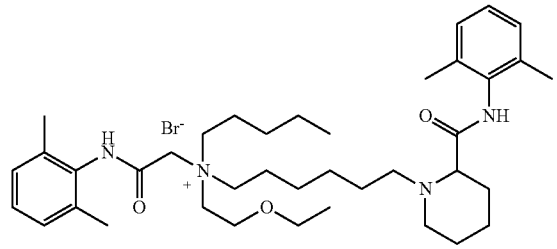
20
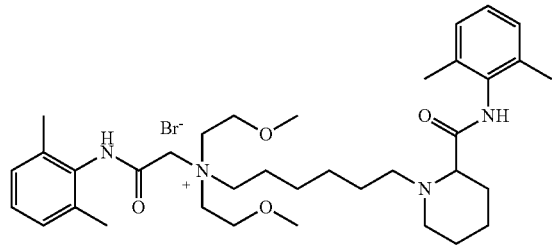
21
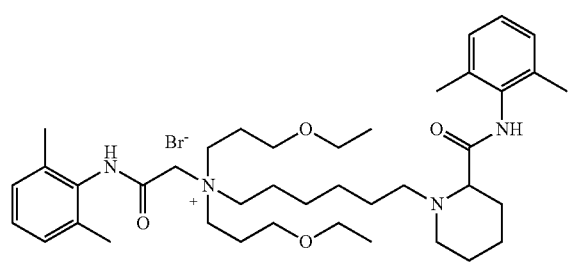
22
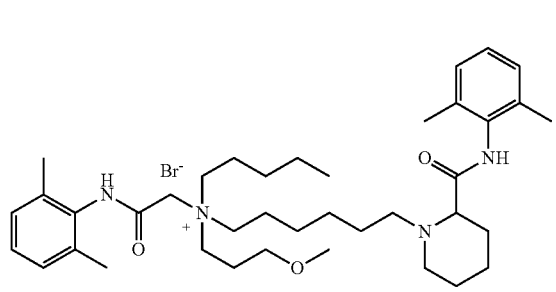
23
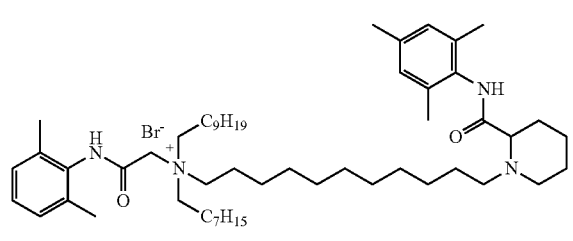
24
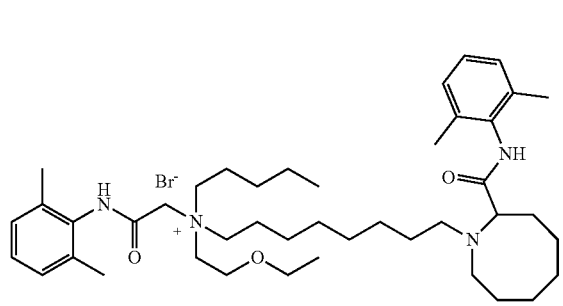
25
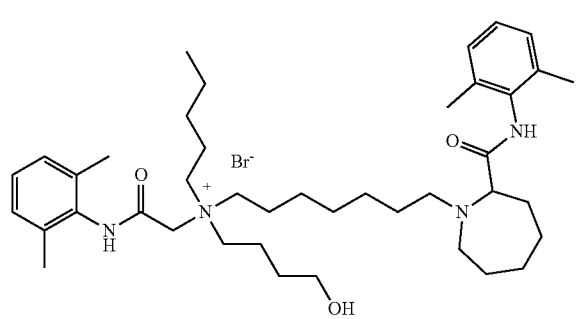
26
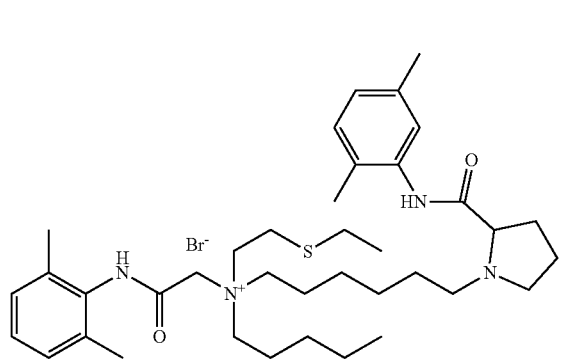
27
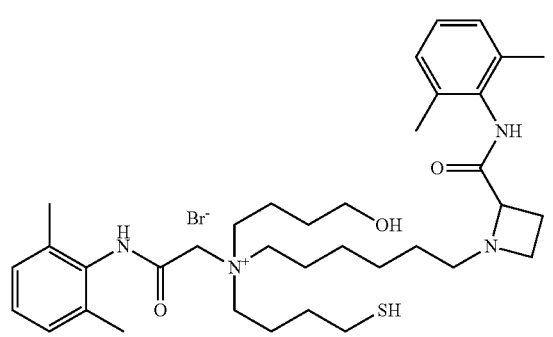
28
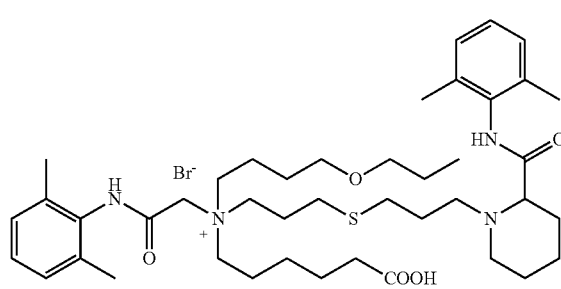
29

-continued
30
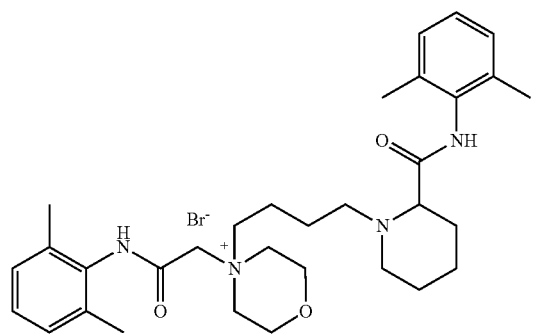
31
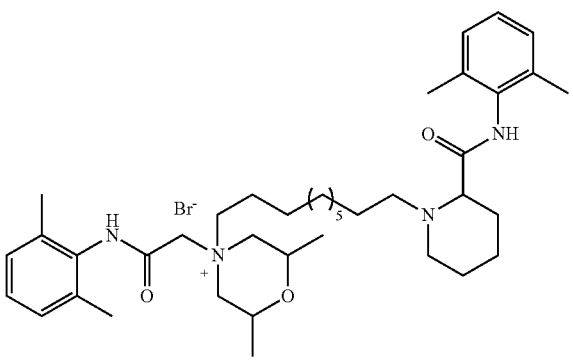
32
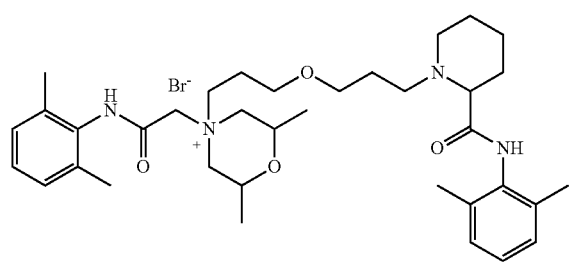
35
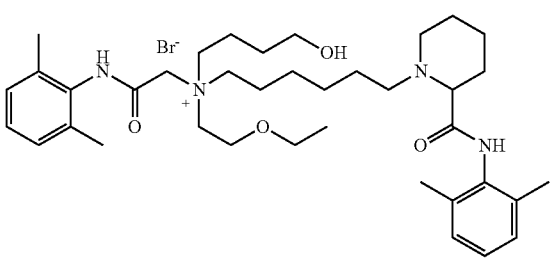
36
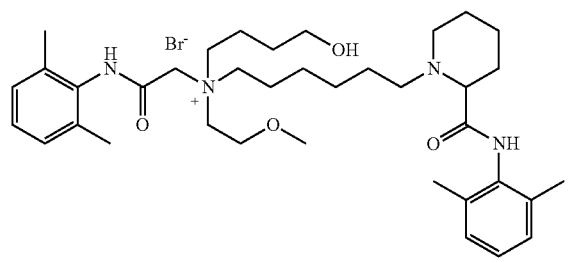
37
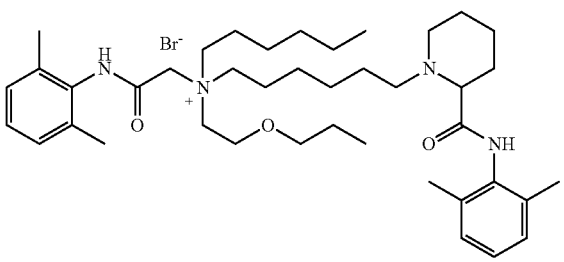
38
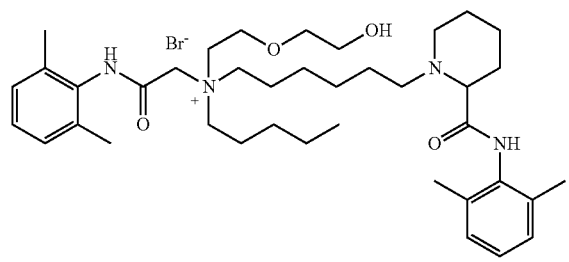
39
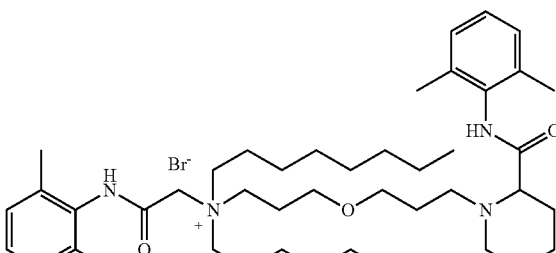
40
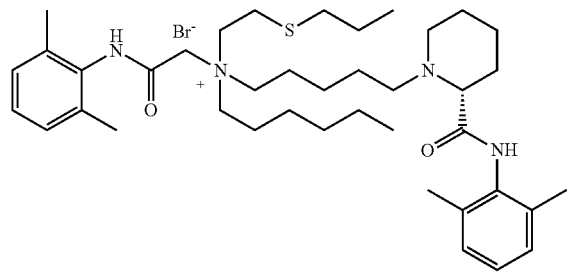
41
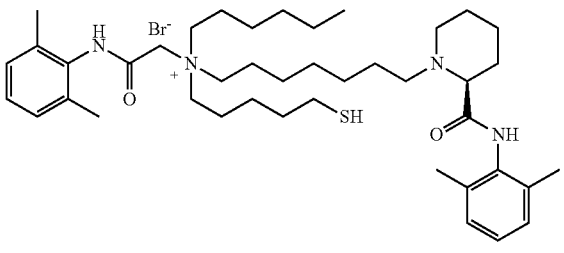

-continued
42
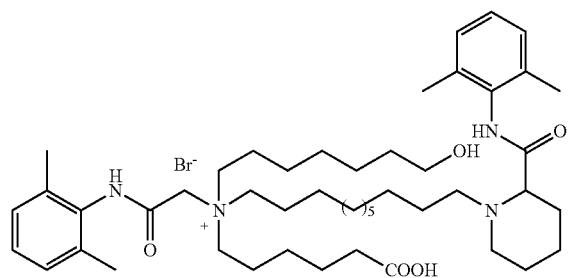
43
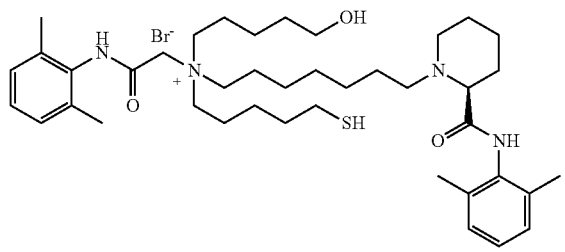
44
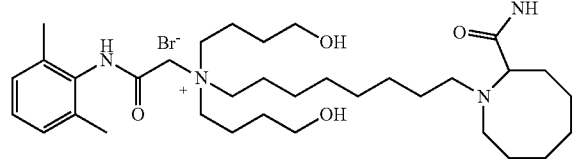
45
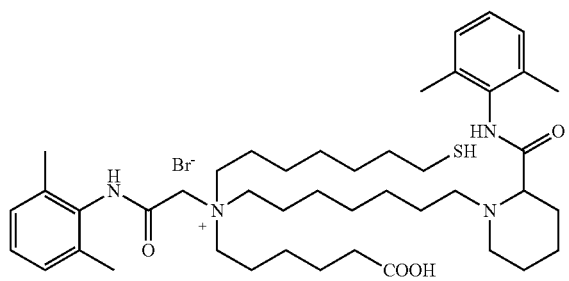
46
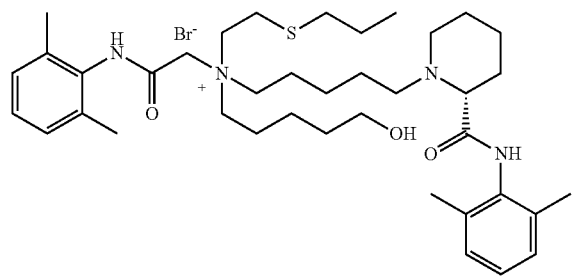
47
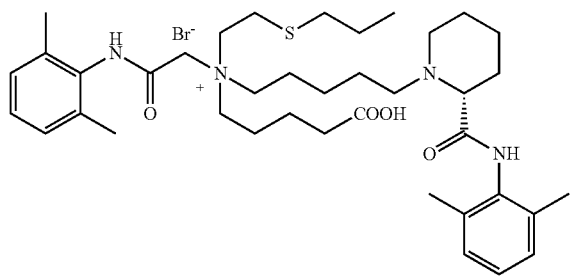
48
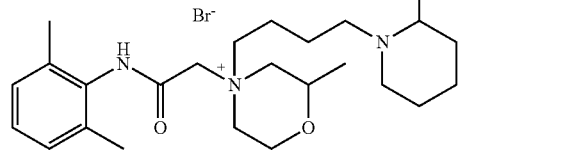
49
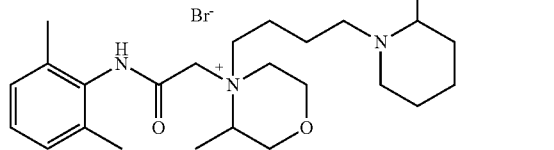
50
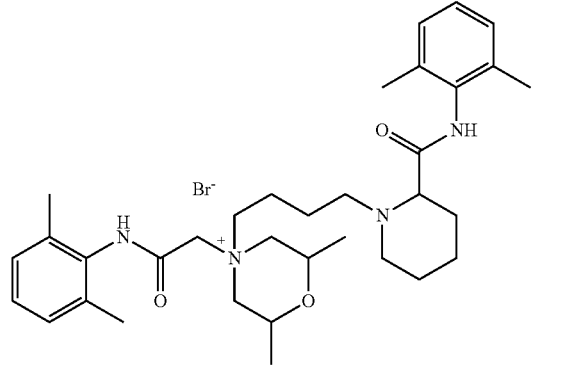
51
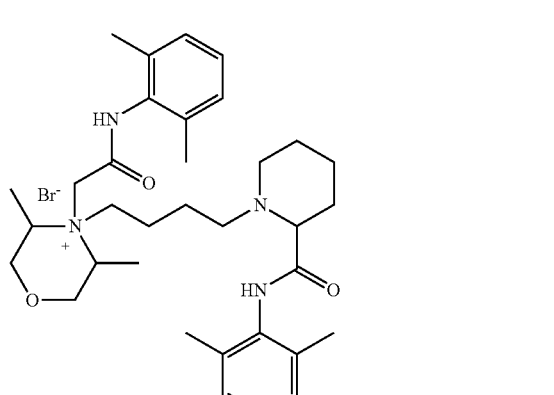

-continued
52
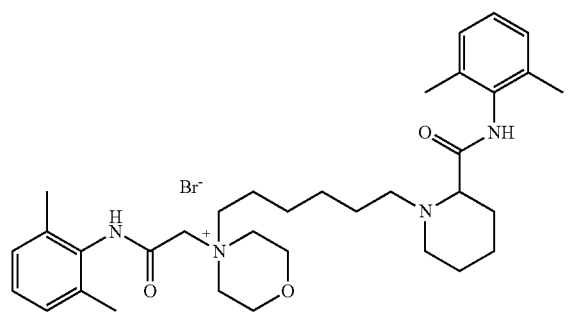
53
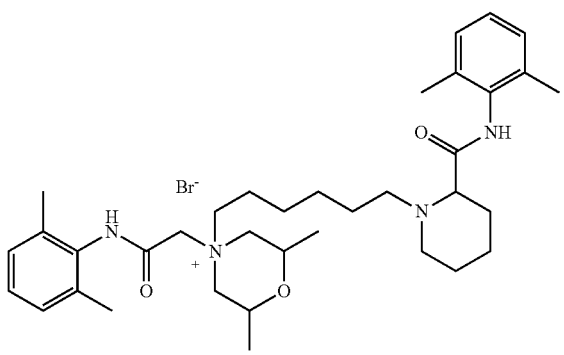
54
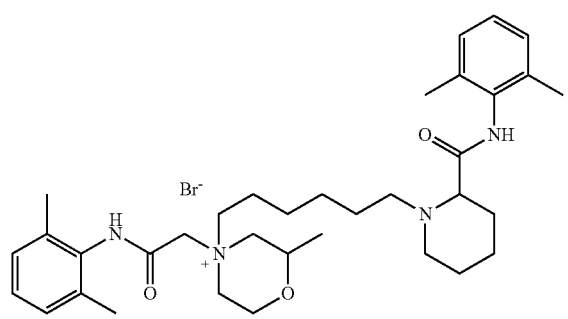
55
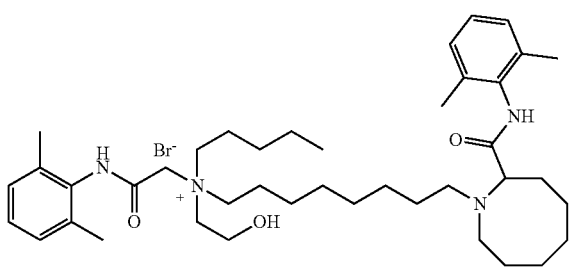
56
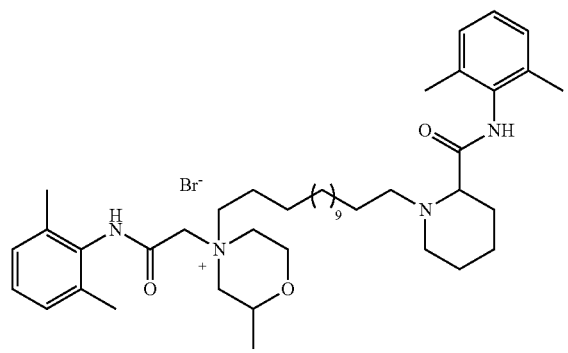
57
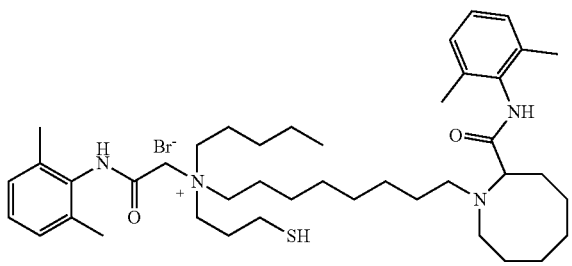
58
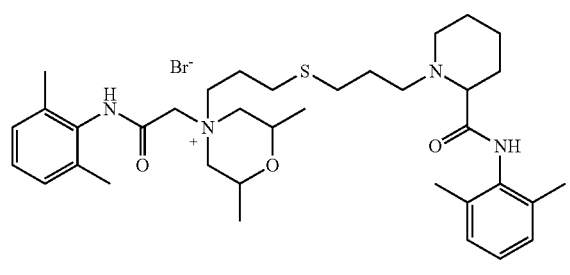
59
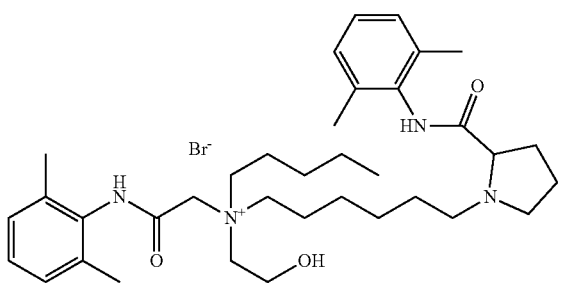

-continued
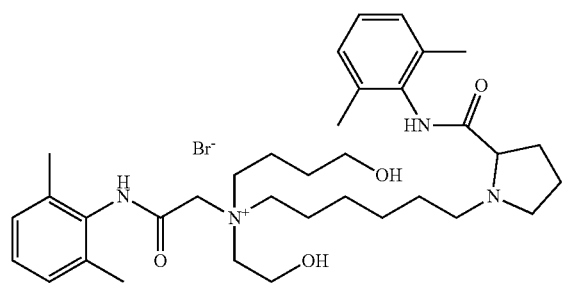
60
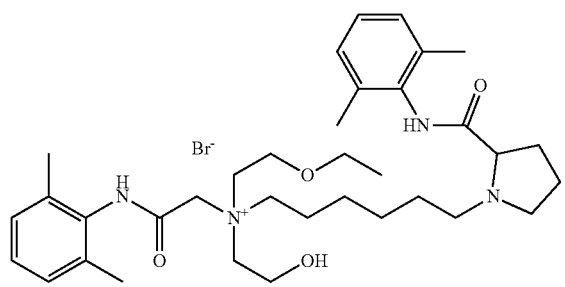
61
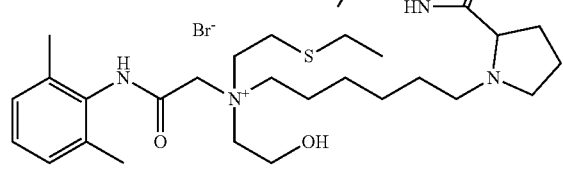
62
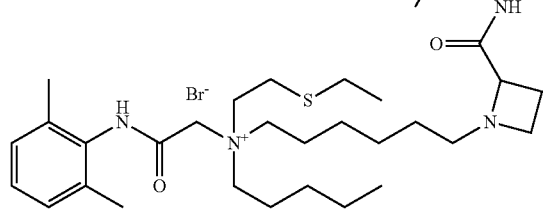
63
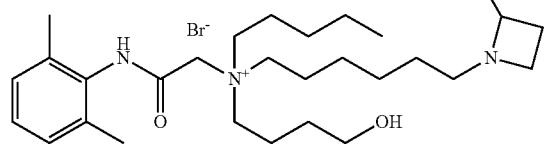
64
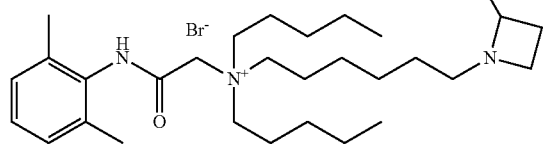
65
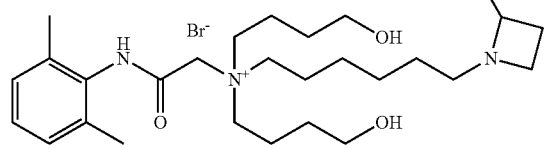
66
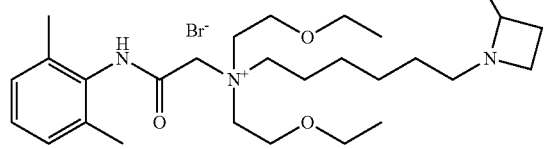
67
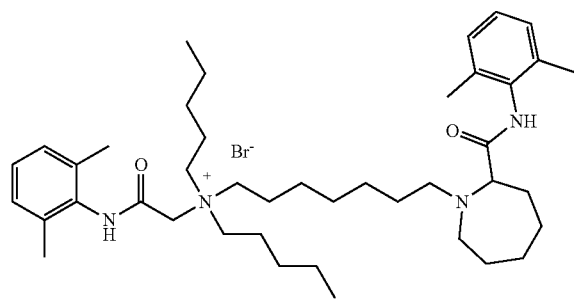
68
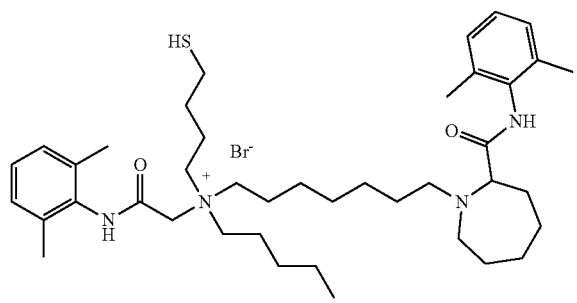
69

-continued

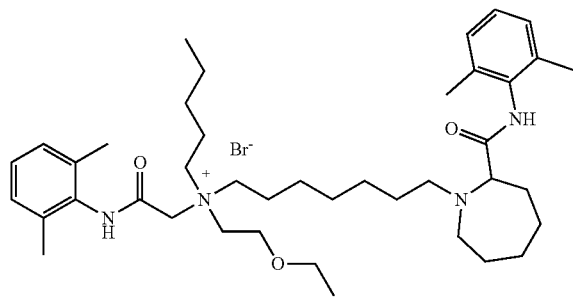
70

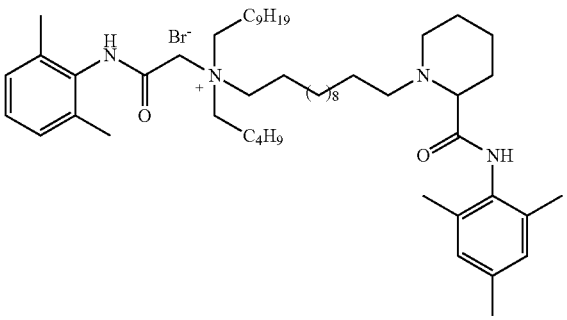
71

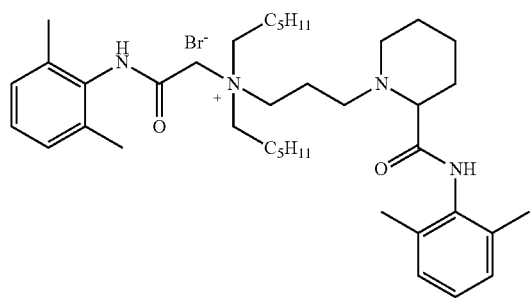
73

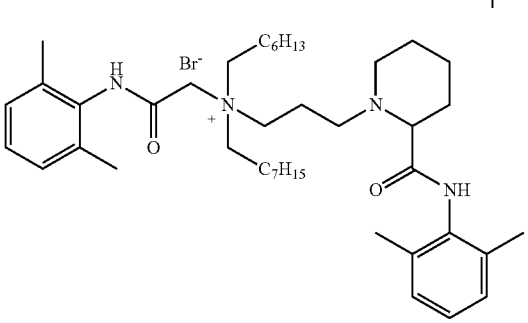
74

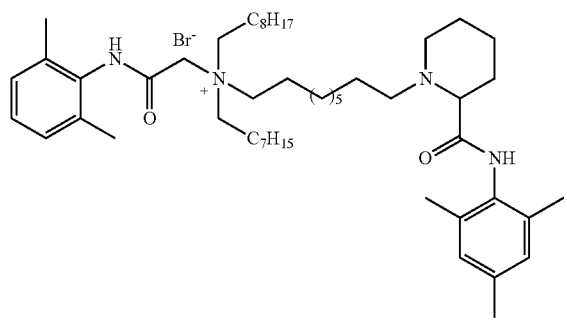
75

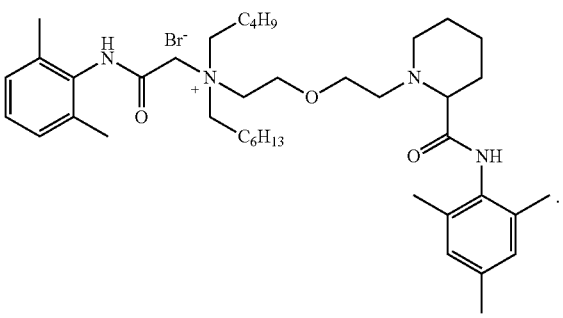
76

The present invention also provides the use of the preparation in preparing a local anesthetic medicine, and said preparation is formed by the compound mentioned above, or a pharmaceutically acceptable salt thereof, or a stereoisomer thereof, or a solvate thereof, or a prodrug thereof, or a metabolite thereof, together with a pharmaceutically acceptable carrier.

Further, said local anesthetic medicine makes the block time of sensory nerve longer than that of motor nerve;
and/or said local anesthesia is long-acting local anesthesia;
Preferably, the anesthesia time of said local anesthesia exceeds 24 hours.

The present invention also provides a drug, which is a preparation formed by the compound mentioned above, or a pharmaceutically acceptable salt thereof, or a stereoisomer thereof, or a solvate thereof, or a prodrug thereof, or a metabolite thereof, with the addition of pharmaceutically acceptable excipients.

The compounds and derivatives provided in the present invention can be named according to IUPAC (International Union of Pure and Applied Chemistry) or CAS (Chemical Abstracting Service, Columbus, OH) naming system.

For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that the hydrogen in a molecule is substituted by other different atoms or molecules.

Halogen is fluorine, chlorine, bromine, or iodine.

"Alkyl" is a hydrocarbon group formed by losing one hydrogen in an alkane molecule, such as methyl —$CH_3$, ethyl —$CH_3CH_2$, etc. "$C_{1-4}$ alkyls" denotes a straight or branched hydrocarbon chain containing 1-4 carbon atoms.

"Alkylenyl" denotes the hydrocarbon group formed by losing two hydrogens in the alkane molecule, such as methylene —$CH_2$—, ethylidene —$CH_2CH_2$—, etc. "$C_{1-4}$ alkylenes" denotes a straight or branched hydrocarbon chain containing 1~4 carbon atoms.

"Substituted or unsubstituted $C_1$-$C_{12}$ alkyls" denote $C_1$-$C_{12}$ alkyls that can be substituted or not be substituted.

"$L_1$ is selected from substituted or unsubstituted $C_{1-12}$ alkylenes; wherein, the main chain of said alkylenyl contains 0~4 heteroatoms" means a straight or branched hydrocarbon chain containing 1~12 carbon atoms; said hydrocarbon chain can be substituted or unsubstituted; "the main chain of said hydrocarbon contains heteroatoms" means that a carbon in the main chain is substituted with a heteroatom, which is O, S, and substituted N.

"Aryls" denote all-carbon monocyclic or fused polycyclic (i.e. ring sharing adjacent carbon atom pairs) groups with conjugated 7E electron system, such as phenyl and naphthyl. Said aryl ring can be fused to other cyclic groups (including saturated and unsaturated rings), but can not contain heteroatoms such as nitrogen, oxygen, or sulfur. At the same time, the point connecting with the parent must be on the carbon in the ring having the conjugated 7E electron system. Aryls can be substituted or unsubstituted, i.e. aryls can be substituted by 0~4 deuterium, $C_1$-$C_4$ alkyl, $C_1$-$C_4$ alkoxy, $C_1$-$C_4$ alkylthio, halogen, nitro, cyano, hydroxyl, carboxyl, amino, and so on.

The term "pharmaceutically acceptable salt" denotes the salt formed by the compound of the present invention and pharmaceutically acceptable inorganic and organic acids, which is suitable for contacting the tissue of the object (e.g. human) without undue side effects. Among them, the preferred inorganic acids include (but not limited to) hydrochloric acid, hydrobromic acid, phosphoric acid, nitric acid, sulfuric acid; the preferred organic acids include (but not limited to) formic acid, acetic acid, propionic acid, succinic acid, naphthalene disulfonic acid (1,5), asiatic acid, oxalic acid, tartaric acid, lactic acid, salicylic acid, benzoic acid, valeric acid, diethylacetic acid, malonic acid, succinic acid, fumaric acid, pimelic acid, adipic acid, maleic acid, malic acid, sulfamic acid, phenylpropionic acid, gluconic acid, ascorbic acid, niacin, isoniacin, methanesulfonic acid, p-toluenesulfonic acid, citric acid, and amino acids.

The term "solvate" denotes the solvate formed by the compound of the present invention and pharmaceutically acceptable solvents, in which the pharmaceutically acceptable solvent includes (but not limited to) water, ethanol, methanol, isopropanol, propylene glycol, tetrahydrofuran, and dichloromethane.

The term "pharmaceutically acceptable stereoisomer" means that the chiral carbon atom involved in the compound of the present invention may be R-configuration, S-configuration, or a combination thereof.

The present invention provides a class of quaternary ammonium compounds with novel structures, as well as the preparative method and the use thereof. The compound has a fast onset of action, a long-time local anesthetic (more than 24 hours, and the local anesthesia time for most compounds exceeding 40 hours) effect after a single administration, a selectivity for nerve block (the block time of sensory nerve is longer than that of motor nerve, and the difference time is greater than or equal to 5 hours, and the difference time for most compounds is greater than 10 hours), as well as has both long-acting and selective local anesthetic effect, that significantly reduced the side effects of QX314, QX314 composition, and the quaternary ammonium compound with surfactant structure characteristics. Moreover, the compound has better safety, that is, the compound of the present invention and its pharmaceutically acceptable salts can be used to prepare safe drugs with long-acting and selective local anesthesia, which has the advantages of long-time local anesthetic action, good local anesthetic selectivity, less nerve damage, and high safety.

Obviously, based on above content of the present invention, according to the common technical knowledge and the conventional means in the field, without department from above basic technical spirits, other various modifications, alternations, or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The starting materials and equipment used in the specific examples of the present invention are all known products and can be obtained by purchasing commercially available items.

Example 1 Preparation of the Compound According to the Present Invention

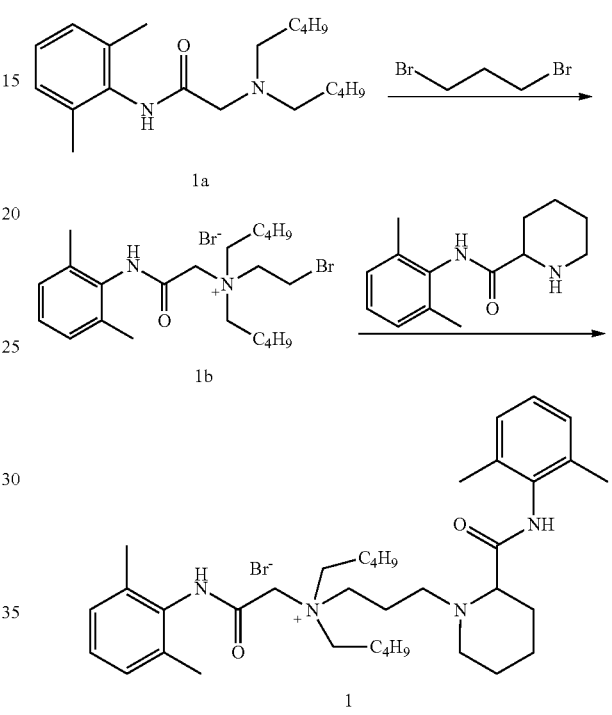

Compound 1a (5.0 g, 45.39 mmol) was dissolved in 1,3-dibromopropane (15 mL), and the mixture was heated to 75° C. and reacted for 40 h. The reaction was monitored by TLC (DCM:MeOH=10:1, Rf=0.3). A suitable amount of ethyl acetate was added to form a viscous syrupy substance. The supernatant was poured out, to obtain the residue of 6 g crude product, which was dissolved in 30 mL methanol and mixed with silica gel. After dry loading, the crude product was purified by silica gel column chromatography, using eluent $CH_2Cl_2$:MeOH=10:1. The eluent was collected and concentrated to obtain 3 g crude product. The resultant product was recrystallized in ethyl acetate and dichloromethane, to prepare 2.5 g off-white solid powder (1b) with a yield of 31.6%, which was used in the next reaction.

Intermediate 1b (2.00 g, 3.66 mmol) prepared above and N-(2,6-dimethylphenyl)-2-piperidinecarboxamide (0.934 g, 4.03 mmol, CAS: 15883-20-2) were dissolved in 20 mL ethanol, to which was added DIPEA (0.94 g, 1.21 mL, 7.32 mmol). The mixture was warmed to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 1.2 g white solid (1). Yield: 48.19%. $^1$H NMR (300 MHz, $CDCl_3$) δ (ppm): 10.35 (s, 1H), 7.84 (s, 1H), 7.11-7.01 (m, 6H), 4.89 (s, 2H), 3.80-3.45 (m, 7H), 2.71-2.57 (m, 4H), 2.28-2.17 (m, 12H), 1.90-1.63 (m, 8H), 1.60-1.27 (m, 12H), 1.02-0.87 (m, 6H). HRMS: m/z 591.9048 $[C_{37}H_{59}N_4O_2]^+$.

Example 2 Preparation of the Compound According to the Present Invention

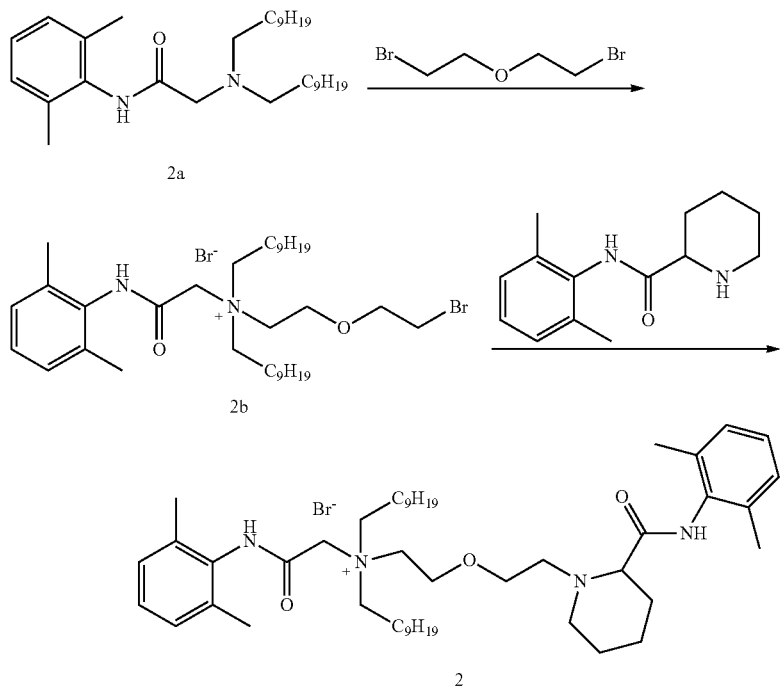

Compound 2a (2.0 g, 40.32 mmol) was dissolved in 2-bromoethyl ether (5 mL), and the mixture was heated to 75° C. and reacted for 24 h. The reaction was monitored by TLC (DCM:MeOH=10:1, Rf=0.3). A suitable amount of ethyl acetate was added, then the reaction solution solidified to produce white solids, and 3 g crude product was filtered out as white solid, that was purified by silica gel column chromatography, using eluent $CH_2Cl_2$:MeOH=20:1. The eluent was collected and concentrated to obtain 5.9 g white solid (intermediate 2b), with a yield of 31.5%, which was used in the next reaction.

Intermediate 2b (1.0 g, 2.16 mmol) prepared above and N-(2,6-dimethylphenyl)-2-piperidinecarboxamide (0.55 g, 2.37 mmol, CAS: 15883-20-2) were dissolved in 15 mL ethanol, to which was added DIPEA (0.53 g, 0.68 ml, 4.12 mmol). The mixture was allowed to react for 10 days at the temperature of 30° C. Then, the solvent was evaporated, and the crude product was purified by silica gel column chromatography, using eluent $CH_2Cl_2$:MeOH=10:1. The eluate was collected and concentrated to obtain 995 mg solid as white powder (2). Yield: 75.1%. $^1$H NMR (300 MHz, $CDCl_3$) δ (ppm): 9.79 (s, 1H), 7.60 (s, 1H), 7.02-6.90 (m, 6H), 4.33 (s, 2H), 3.63-3.41 (m, 3H), 3.25-3.01 (m, 6H), 2.87-2.68 (m, 6H), 2.08 (s, 6H), 2.07 (s, 6H), 1.89-1.74 (m, 6H), 1.60-1.40 (m, 4H), 1.40-1.20 (m, 28H), 1.05-0.88 (m, 6H). HRMS: m/z 763.2013 $[C_{48}H_{81}N_4O_3]^+$.

Example 3 Preparation of the Compound According to the Present Invention

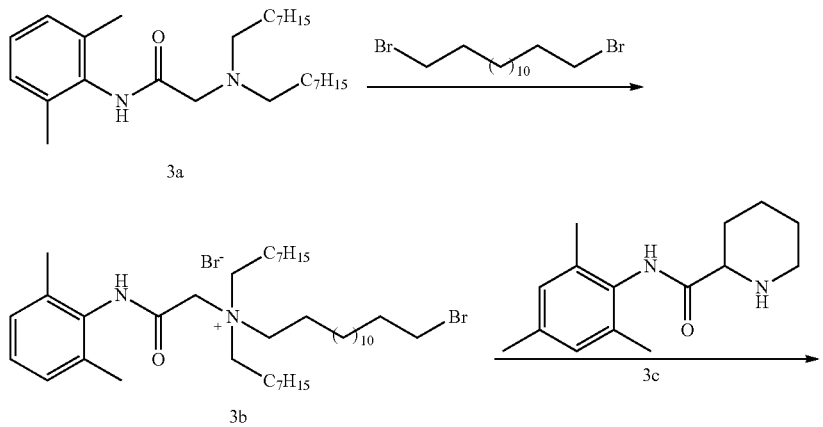

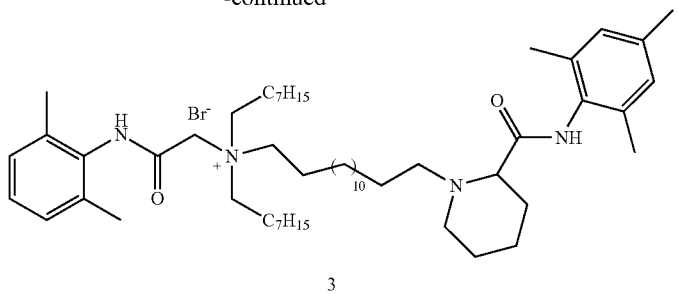

3

Compound 3a (500 mg, 1.2 mmol) and 1,14-dibromotetradecane (2 g, 6.0 mmol) were dissolved in acetonitrile (5 mL), and the mixture was heated to 70° C. and reacted for 24 h. The reaction was monitored by TLC (DCM:MeOH=20:1, Rf=0.3). A suitable amount of ethyl acetate was added, then the reaction solution solidified to produce white solids, and 0.9 g crude product was filtered out as white solid, which was purified by silica gel column chromatography, using eluent $CH_2Cl_2$:MeOH=20:1. The eluent was collected and concentrated to obtain 500 mg white powder solid (3b), with a yield of 54.1%, which was used in the next reaction.

Intermediates 3b (500 mg, 0.65 mmol) and 3c (0.18 g, 0.71 mmol) prepared above were dissolved in the solvent mixture of 30 mL ethanol and 5 mL methanol, to which was added DIPEA (0.17 g, 0.21 mL, 1.3 mmol). The mixture was allowed to react for 10 days at the temperature of 30° C. After completion of the reaction, the crude product was purified by silica gel column chromatography, using eluent $CH_2Cl_2$:MeOH=10:1. The eluate was collected and concentrated to obtain 400 mg white powder solid (3). Yield: 39.6%. $^1$H NMR (300 MHz, $CDCl_3$) δ (ppm): 10.24 (s, 1H), 8.39 (s, 1H), 7.05-6.87 (m, 5H), 4.38 (s, 2H), 3.60-3.50 (m, 4H), 3.30-3.05 (m, 3H), 2.45-2.32 (m, 4H), 2.26 (s, 3H), 2.17-2.14 (m, 12H), 2.05-1.83 (m, 8H), 1.55-1.23 (m, 48H), 1.02-0.83 (m, 6H). HRMS: m/z 858.4177 $[C_{56}H_{97}N_4O_2]^+$.

Example 4 Preparation of the Compound According to the Present Invention

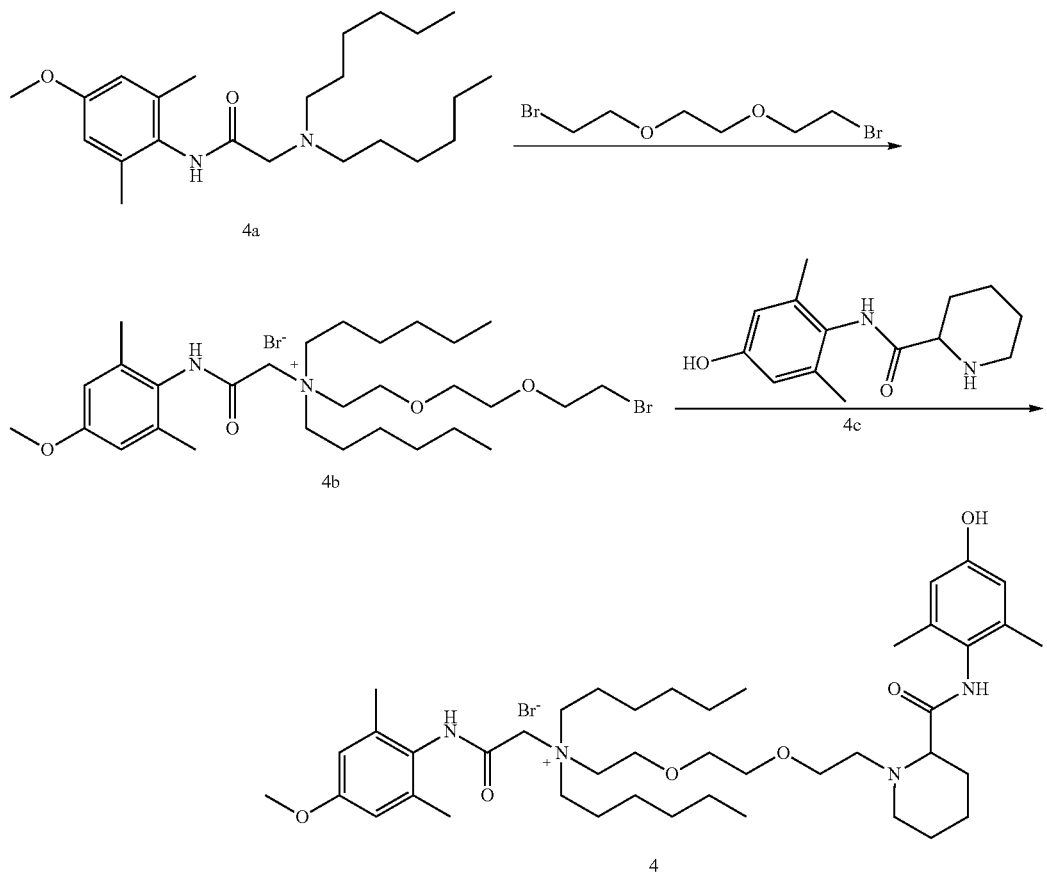

Compound 4a (1 g, 2.7 mmol) was dissolved in bromo-PEG3-alcohol (3 mL), and the mixture was heated to 75° C. and reacted for 40 h. The reaction was monitored by TLC (DCM:MeOH=10:1). A suitable amount of ethyl acetate was added to form a viscous syrupy substance. The supernatant was poured out, and the residual solid was dissolved, mixed with silica gel, and purified by silica gel column chromatography, with eluent $CH_2Cl_2$:MeOH=10:1. The eluent was collected and concentrated to obtain 1.6 g crude product. The resultant product was recrystallized in ethyl acetate and dichloromethane, to prepare 1.2 g off-white solid powder (4b), which was directly used in the next reaction.

Intermediates 4b (1.00 g, 1.54 mmol) and 4c (420 mg, 1.7 mmol) prepared above were dissolved in 10 mL ethanol, to which was added DIPEA (0.88 mL, 5.3 mmol). The mixture was heated to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 500 mg white solid (4). Yield: 39.7%. $^1$H NMR (300 MHz, CDCl$_3$) δ (ppm): 10.50 (s, 1H), 9.19 (s, 1H), 8.13 (s, 1H), 7.11-7.01 (m, 4H), 4.73 (s, 2H), 3.81-3.73 (m, 6H), 3.56-3.23 (s, 13H), 2.53-2.40 (m, 3H), 2.27 (s, 6H), 2.23 (s, 6H), 2.95-1.78 (m, 8H), 1.42-1.29 (s, 14H), 0.99-0.88 (m, 6H). HRMS: m/z 740.0623 $[C_{43}H_{71}N_4O_6]^+$.

Example 5 Preparation of the Compound According to the Present Invention

Compound 5a (5.0 g, 13.7 mmol) was dissolved in 10 mL of 1,8-dibromooctane, and the mixture was heated to 70° C. and reacted. The reaction was monitored by TLC (DCM:MeOH=10:1). After completion of the reaction, the solvent was evaporated, and the crude product was purified by silica gel column chromatography, using eluent $CH_2Cl_2$:MeOH=20:1. The eluent was collected and concentrated to obtain 5 g dark brown compound (5b), with a yield of 57.5%, which was used in the next reaction.

Intermediates 5b (1 g, 1.58 mmol) and 5c (0.40 g, 1.74 mmol) prepared above were dissolved in 15 mL ethanol, to which was added DIPEA (0.52 g, 3.15 mmol). The mixture was allowed to react for 13 days at the temperature of 30° C., and the reaction was detected by TLC (DCM:MeOH=10:1). After completion of the reaction, the solvent was evaporated, and the crude product was purified by silica gel column chromatography, using eluent $CH_2Cl_2$:MeOH=10:1. The eluate was collected and concentrated to obtain 600 mg white solid (5). Yield: 48.8%. $^1$H NMR (300 MHz, CDCl$_3$) δ (ppm): 9.81 (s, 1H), 8.69 (s, 1H), 7.06-6.90 (m, 5H), 4.64 (s, 2H), 3.81-3.76 (m, 4H), 3.41-3.22 (m, 11H), 3.07-2.95 (m, 1H), 2.65-2.42 (m, 4H), 2.15-1.95 (m, 12H), 1.80-1.60 (m, 10H), 1.60-1.12 (m, 14H), 1.01-0.88 (m, 6H). HRMS: m/z 708.0641 $[C_{43}H_{71}N_4O_4]^+$.

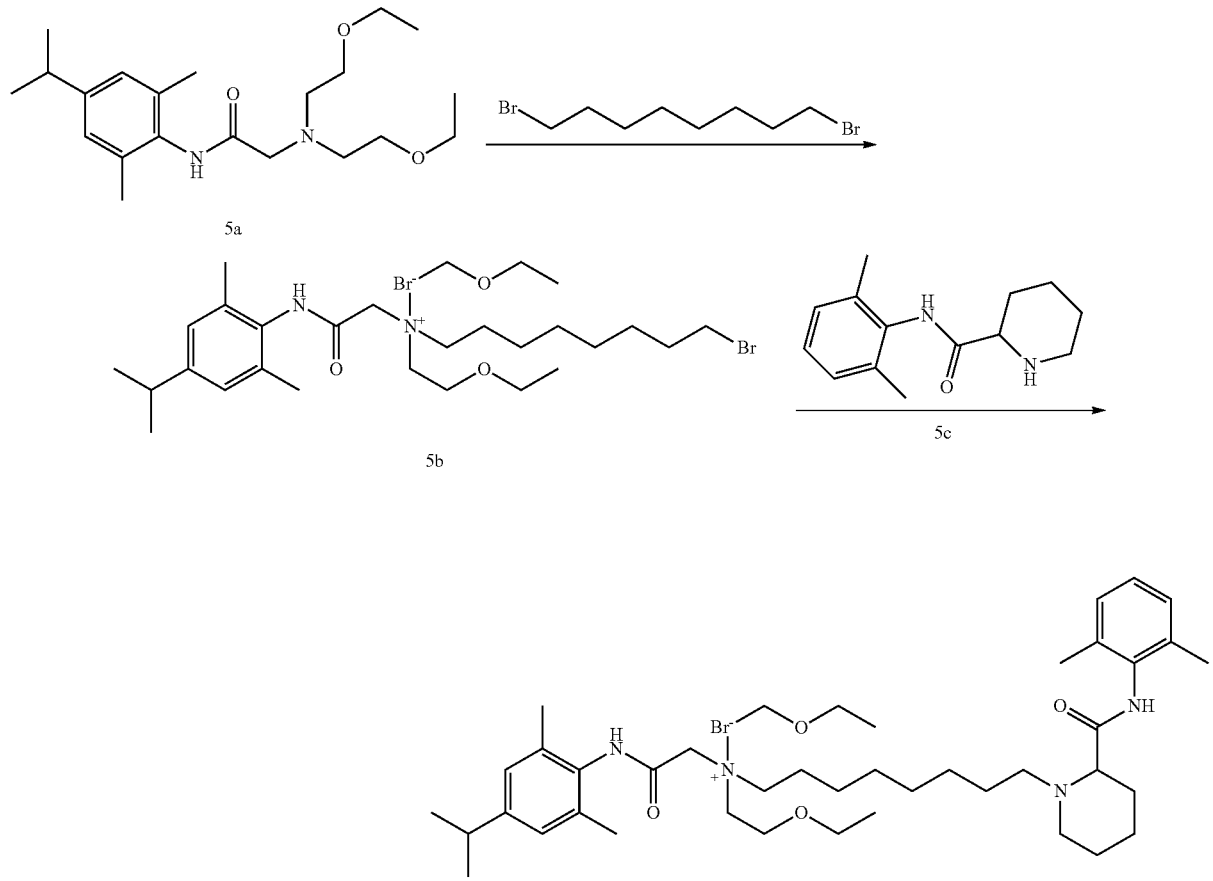

Example 6 Preparation of the Compound According to the Present Invention

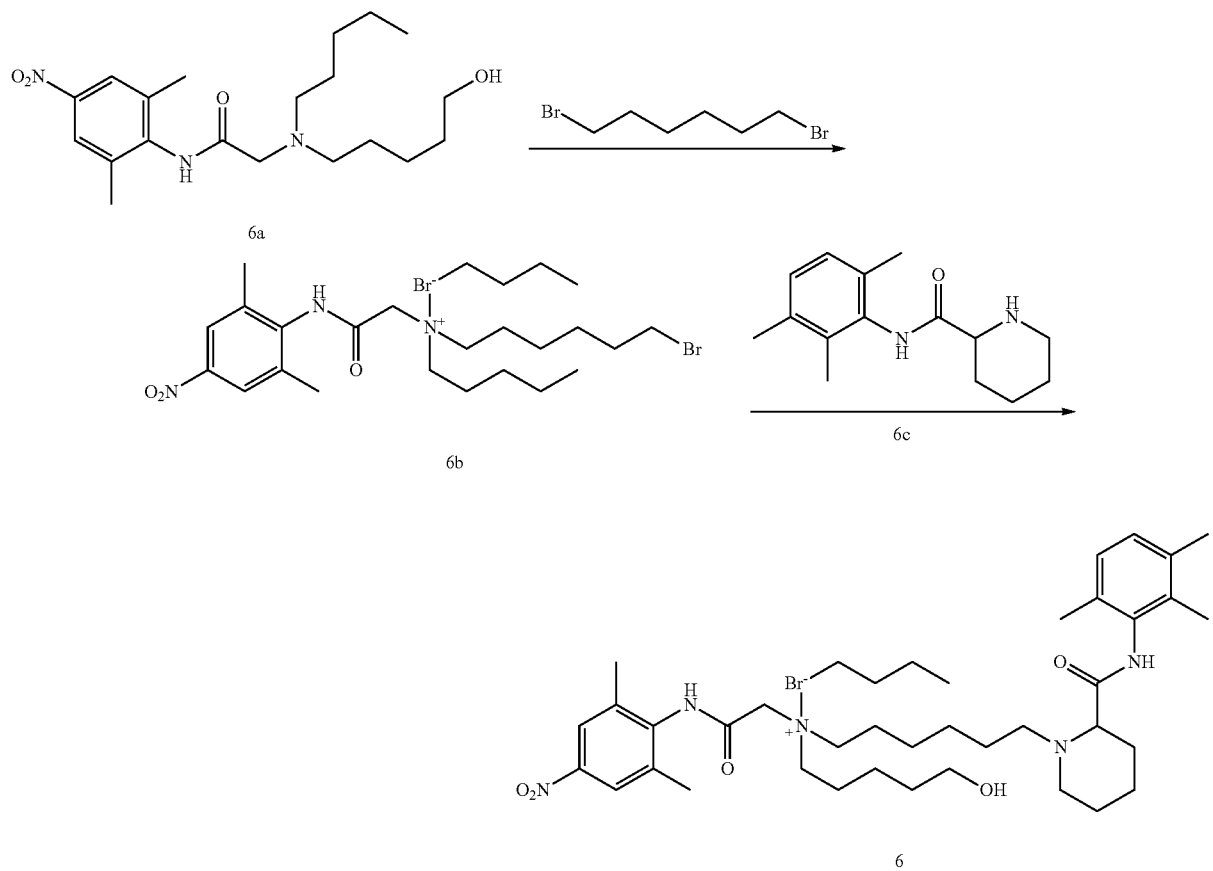

Compound 6a (2.0 g, 5.28 mmol) was dissolved in 1,6-dibromohexane (8 mL), and the mixture was heated to 75° C. and reacted for 30 h. The reaction was monitored by TLC (DCM:MeOH=10:1, Rf=0.3). A suitable amount of ethyl acetate was added to form a viscous syrupy substance. The supernatant was poured out, to obtain the residue of 3 g crude product, which was dissolved in 30 mL methanol and mixed with silica gel. After dry loading, the crude product was purified by silica gel column chromatography, with eluent $CH_2Cl_2$:MeOH=10:1. The eluate was collected and concentrated to obtain 1.5 g crude product. The resultant product was recrystallized in ethyl acetate and dichloromethane, to prepare 1.2 g off-white solid powder (6b) with a yield of 36.6%, which was used in the next reaction.

Intermediates 6b (1.00 g, 1.54 mmol) and 6c (0.44 g, 1.77 mmol) prepared above were dissolved in 10 mL ethanol, to which was added DIPEA (0.42 g, 0.53 mL, 3.22 mmol). The mixture was heated to 80° C. and kept for 50 hours. Then, the solvent was evaporated, and the crude product was purified by silica gel column chromatography, using eluent: $CH_2Cl_2$:MeOH=10:1. The eluate was collected and concentrated to obtain 400 mg white solid (6). Yield: 31.6%. $^1$H NMR (300 MHz, $CDCl_3$) δ (ppm): 10.35 (s, 1H), 9.89 (s, 1H), 7.84 (m, 3H), 7.11-7.01 (m, 2H), 4.77 (s, 2H), 3.51-3.45 (m, 3H), 3.28-3.19 (m, 6H), 2.71-2.57 (m, 4H), 2.28-2.07 (m, 15H), 2.02 (m, 1H), 1.90-1.63 (m, 12H), 1.60-1.27 (m, 13H), 0.95-0.88 (m, 3H). HRMS: m/z 709.0084 $[C_{41}H_{66}N_5O_5]^+$.

Example 7 Preparation of the Compound According to the Present Invention

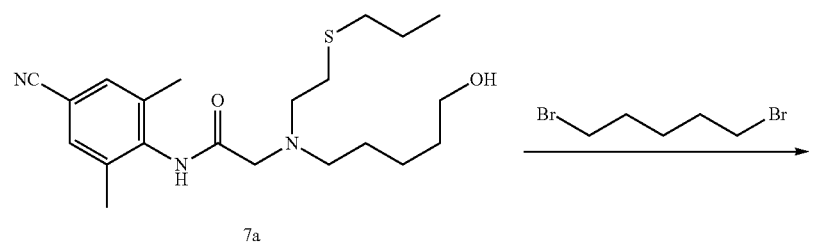

-continued

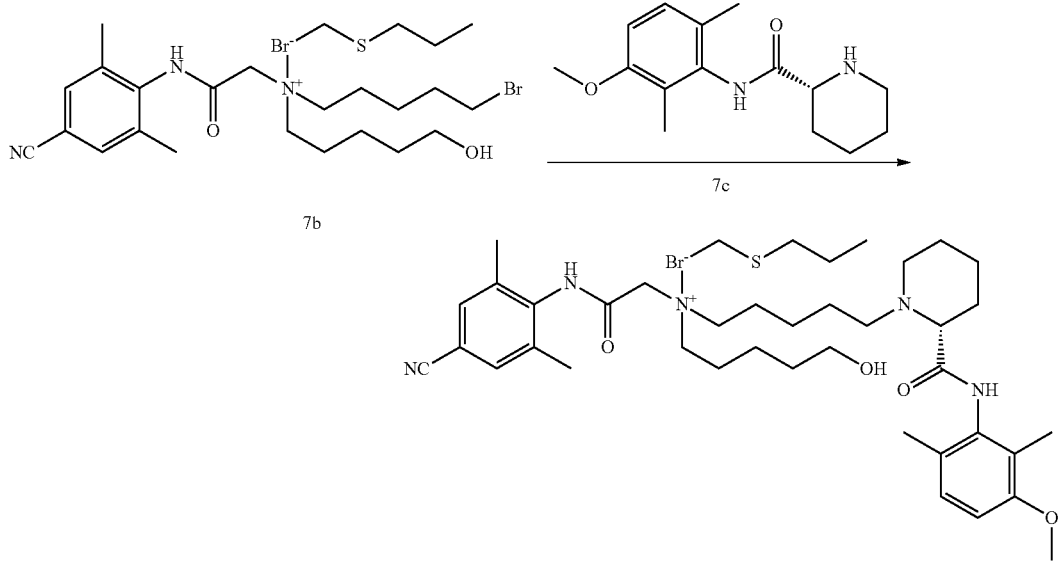

Compound 7a (2.0 g, 5.11 mmol) was dissolved in 1,5-dibromopentane (10 mL), and the mixture was heated to 75° C. and reacted for 50 h. The reaction was monitored by TLC (DCM:MeOH=10:1). A suitable amount of ethyl acetate was added to form a viscous syrupy substance. The supernatant was poured out, and the residue was dissolved and mixed with silica gel. After dry loading, the crude product was purified by silica gel column chromatography, with eluent $CH_2Cl_2$:MeOH=10:1. The eluent was collected and concentrated to obtain 2.0 g crude product. The crude product was recrystallized in ethyl acetate and dichloromethane, to prepare 1.4 g off-white solid powder (7b), which was used in the next reaction.

Intermediates 7b (1.00 g, 1.58 mmol) and 7c (431 mg, 1.74 mmol) prepared above were dissolved in 10 mL ethanol, to which was added DIPEA (0.52 mL, 3.16 mmol). The mixture was heated to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 450 mg white solid (7). Yield: 37.0%. $^1$H NMR (300 MHz, $CDCl_3$) δ (ppm): 9.58 (s, 1H), 8.13 (s, 1H), 7.11-7.01 (m, 4H), 4.85 (s, 2H), 3.77 (s, 3H), 3.65-3.42 (s, 5H), 3.31-3.24 (m, 4H), 2.86-2.79 (m, 2H), 2.43-2.18 (m, 9H), 2.15-2.08 (m, 9H), 2.17-1.96 (m, 4H), 1.76 (s, 8H), 1.60-1.42 (m, 12H). HRMS: $[C_{41}H_{64}N_5O_4S]^+$, 723.0535.

Example 8 Preparation of the Compound According to the Present Invention

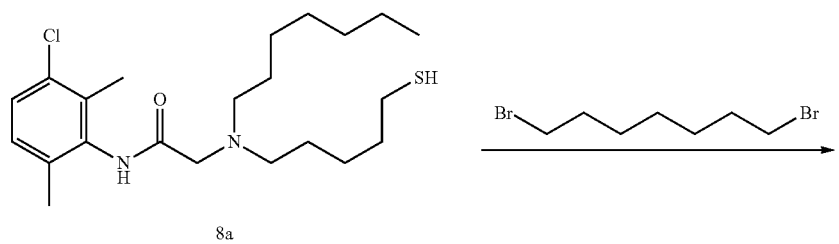

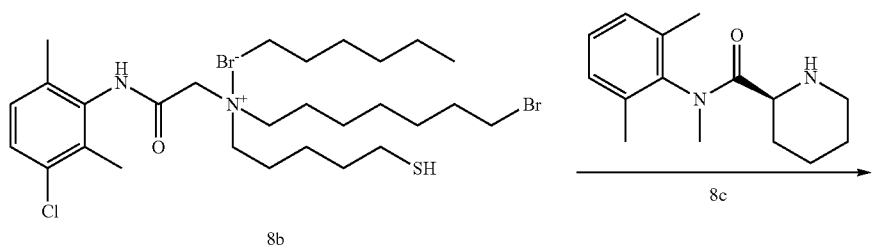

-continued

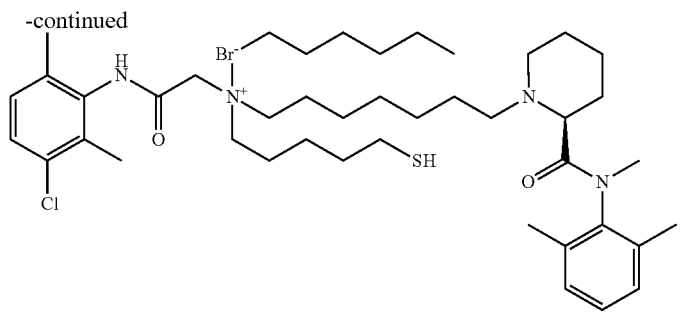

8

Compound 8a (2.0 g, 4.85 mmol) was dissolved in 1,7-dibromoheptane (4 mL), and the mixture was heated to 70° C. and reacted for 48 h. The reaction was monitored by TLC (DCM:MeOH=20:1, $R_f$=0.3). A suitable amount of ethyl acetate was added, then the reaction solution solidified to produce white solids, and 3.0 g crude product was filtered out as white solid, which was purified by silica gel column chromatography, using eluent $CH_2Cl_2$:MeOH=20:1. The eluent was collected and concentrated to obtain 1.6 g white powder solid (8b), with a yield of 49.3%, which was used in the next reaction.

Intermediates 8b (1.5 g, 2.24 mmol) and 8c (0.61 g, 2.47 mmol) prepared above were dissolved in the solvent mixture of 30 mL ethanol and 5 mL methanol, to which was added DIPEA (0.58 g, 0.74 mL, 4.48 mmol). The mixture was allowed to react for 12 days at the temperature of 30° C. After completion of the reaction, the crude product was purified by silica gel column chromatography, using eluent $CH_2Cl_2$:MeOH=10:1. The eluate was collected and concentrated to obtain 600 mg white powder solid (3), with a yield of 32.1%. $^1$H NMR (300 MHz, $CDCl_3$) δ (ppm): 10.02 (s, 1H), 9.89 (s, 1H), 7.23-6.87 (m, 5H), 4.48 (s, 2H), 3.60-3.50 (m, 3H), 3.45-3.33 (m, 6H), 2.63-2.40 (m, 6H), 2.17-2.14 (m, 12H), 1.93-1.75 (m, 11H), 1.49-1.31 (m, 22H), 0.92-0.83 (m, 3H). HRMS: m/z 756.5955 $[C_{44}H_{72}ClN_4O_2S]^+$.

Example 9 Preparation of the Compound According to the Present Invention

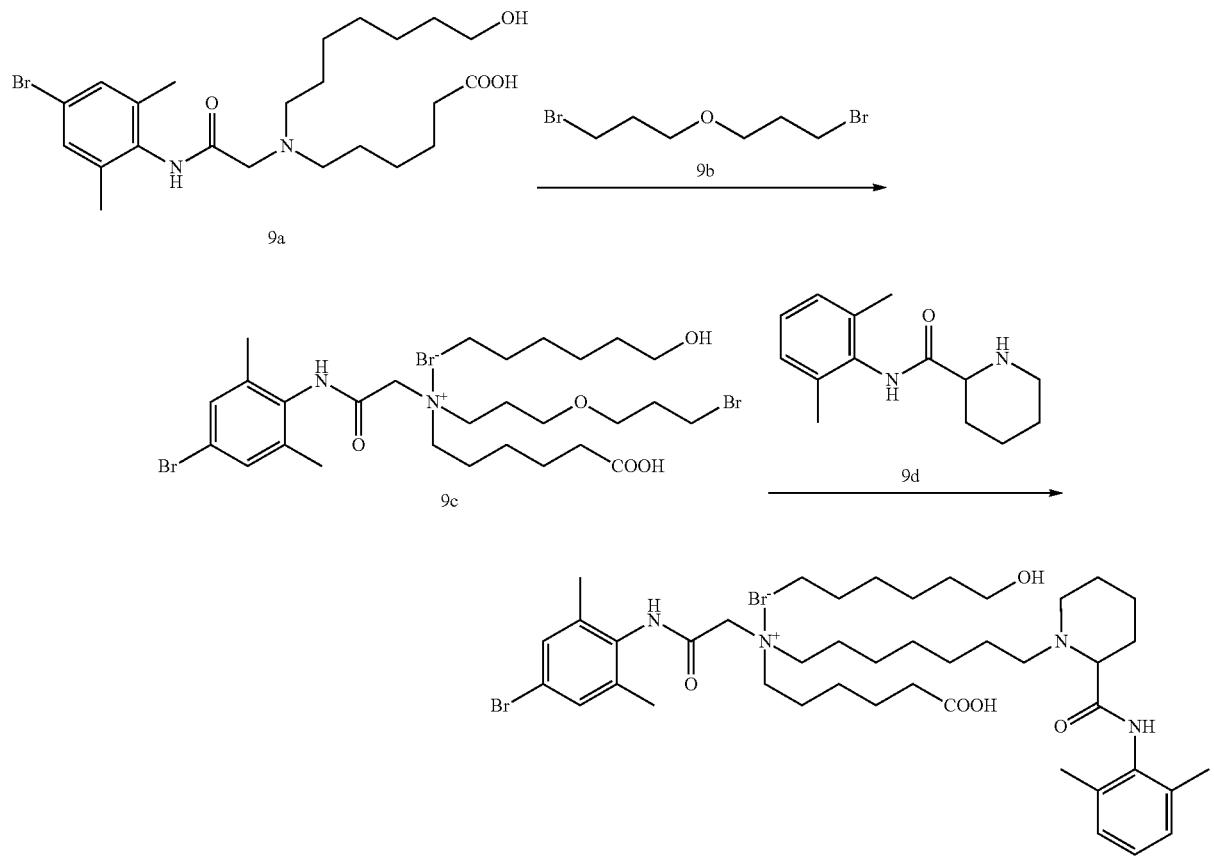

Compounds 9a (3.0 g, 6.2 mmol) and 9b (8 g, 31 mmol) was heated to 75° C. and reacted for 40 h. The reaction was monitored by TLC (DCM:MeOH=10:1). A suitable amount of ethyl acetate was added to form a viscous syrupy substance. The supernatant was poured out, and the residue of the crude product (4.5 g) was dissolved in 30 mL methanol and mixed with silica gel. After dry loading, the crude product was purified by silica gel column chromatography, with eluent CH$_2$Cl$_2$:MeOH=10:1. The eluent was collected and concentrated to obtain 2.5 g crude product. The crude product was recrystallized in ethyl acetate and dichloromethane, to prepare 2.0 g off-white solid powder (9c) with a yield of 43.4%, which was used in the next reaction.

Intermediates 9c (1.00 g, 1.35 mmol) and 9d (0.344 g, 1.48 mmol) prepared above were dissolved in 10 mL ethanol, to which was added DIPEA (0.35 g, 0.45 mL, 2.70 mmol). The mixture was heated to 80° C. and kept for 40 hours. Then, the solvent was evaporated, and the crude product was purified by silica gel column chromatography, using eluent CH$_2$Cl$_2$:MeOH=10:1. The eluate was collected and concentrated to obtain 400 mg white solid (9). Yield: 33.2%. $^1$H NMR (300 MHz, CDCl$_3$) δ (ppm): 10.05 (s, 1H), 7.84 (s, 1H), 7.11-7.01 (m, 5H), 4.15 (s, 2H), 3.60-3.35 (m, 7H), 3.25-3.18 (s, 8H), 2.45-2.21 (m, 8H), 2.14-2.03 (m, 12H), 1.91-1.56 (m, 12H), 1.46-1.23 (m, 14H). HRMS: m/z 830.9697 [C$_{44}$H$_{70}$BrN$_4$O$_6$]$^+$.

Example 10 Preparation of the Compound According to the Present Invention

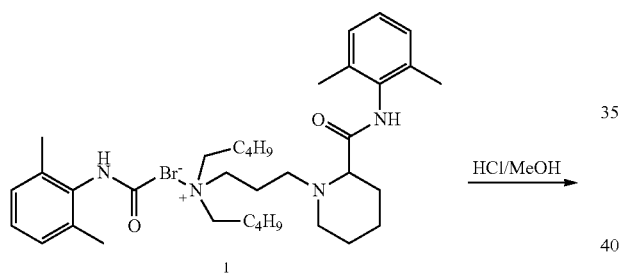

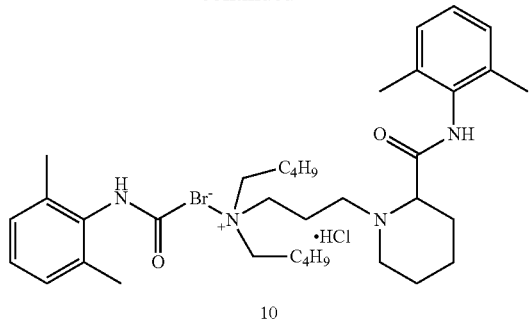

200 mg of the product obtained in Example 1 was dissolved in 10 mL of dichloromethane, to which was added dropwise the solution of 0.1 mol/L hydrochloric acid-methanol at equal molar concentration in an ice bath, and then the resultant solution was concentrated to dryness under reduced pressure. The residue was dried in vacuum to provide a pale yellow solid (10), with a yield of 97.5%. $^1$H NMR (300 MHz, CDCl$_3$) δ (ppm): 10.33 (s, 1H), 8.68 (s, 1H), 7.19-7.11 (m, 6H), 4.93 (s, 2H), 3.76-3.38 (m, 7H), 2.70-2.59 (m, 4H), 2.27-2.18 (m, 12H), 1.91-1.61 (m, 8H), 1.64-1.27 (m, 12H), 1.10-0.88 (m, 6H). HRMS: m/z 591.9047 [C$_{37}$H$_{59}$N$_4$O$_2$]$^+$.

Example 11 Preparation of the Compound According to the Present Invention

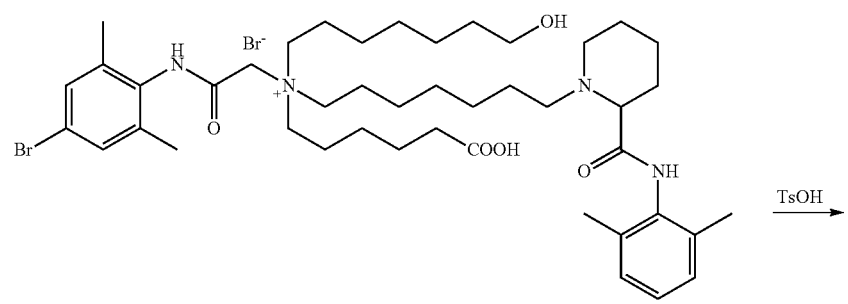

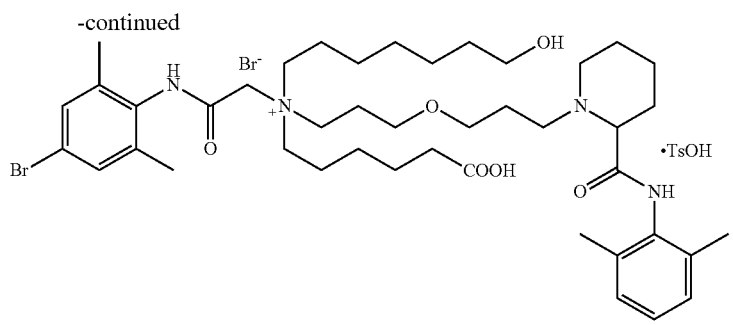

11

200 mg of the product obtained in Example 9 was dissolved in 10 mL of dichloromethane, to which was added 1 eq p-toluenesulfonic acid, and then the resultant solution was concentrated to dryness under reduced pressure. The residue was dried in vacuum to provide a pale yellow solid (11), with a yield of 92.5%.

$^1$H NMR (300 MHz, CDCl$_3$) δ (ppm): 10.03 (s, 1H), 8.92 (s, 1H), 7.13-7.02 (m, 5H), 4.19 (s, 2H), 3.62-3.37 (m, 7H), 3.27-3.19 (s, 8H), 2.48-2.23 (m, 8H), 2.17-2.06 (m, 12H), 1.94-1.58 (m, 12H), 1.46-1.24 (m, 14H). HRMS: m/z 830.9699 [C$_{44}$H$_{70}$BrN$_4$O$_6$]$^+$.

Example 12 Preparation of the Compound According to the Present Invention

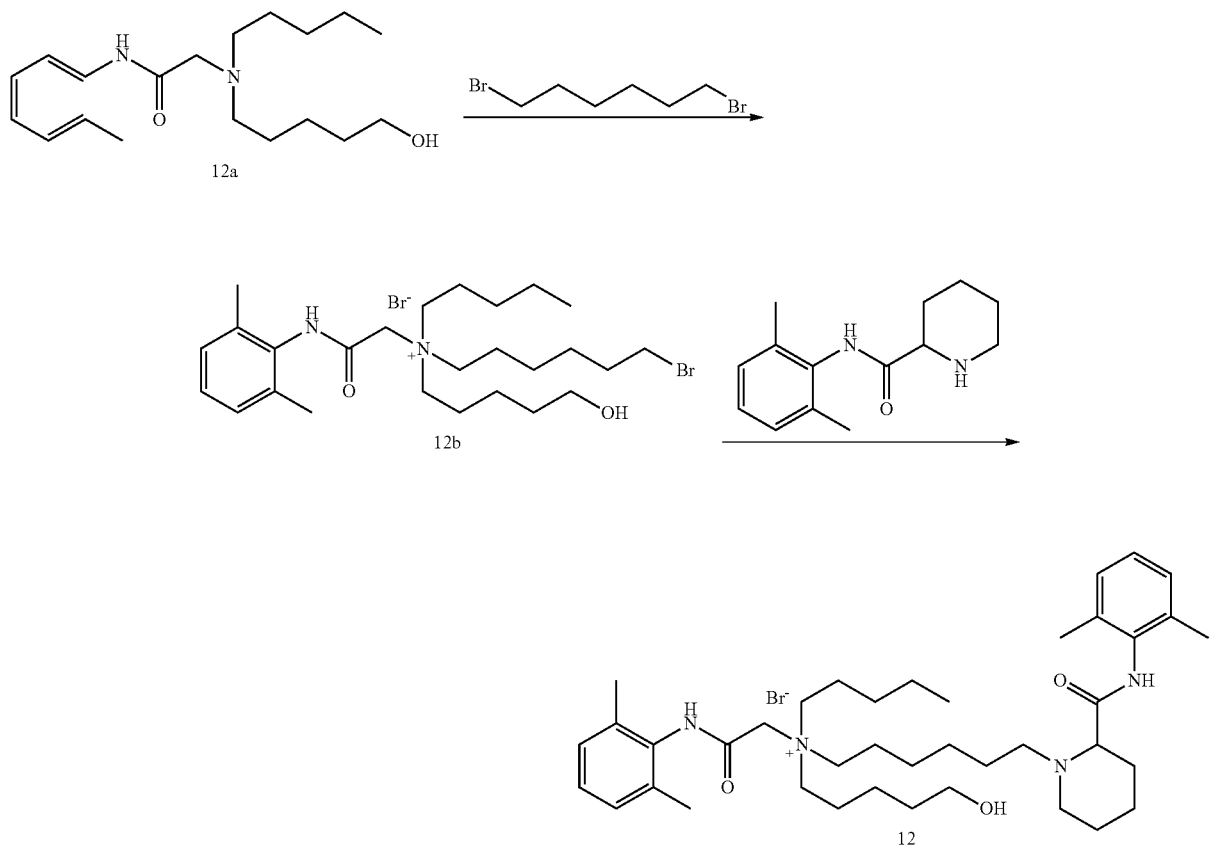

With reference to the method in Example 6, an off-white solid powder was obtained, with a yield of 35.2%.

$^1$H NMR (300 MHz, CDCl$_3$) δ (ppm): 10.30 (s, 1H), 9.89 (s, 1H), 7.33 (m, 6H), 4.72 (s, 1H), 4.25 (s, 2H), 3.67 (t, 2H), 3.45 (t, 1H), 3.26-3.18 (m, 6H), 2.51-2.37 (m, 4H), 2.13 (s, 12H), 2.02 (m, 2H), 1.90-1.63 (m, 6H), 1.60-1.27 (m, 18H), 0.95-0.88 (m, 3H). HRMS: m/z 649.9843 [C$_{40}$H$_{65}$N$_4$O$_3$]$^+$.

Example 13 Preparation of the Compound According to the Present Invention

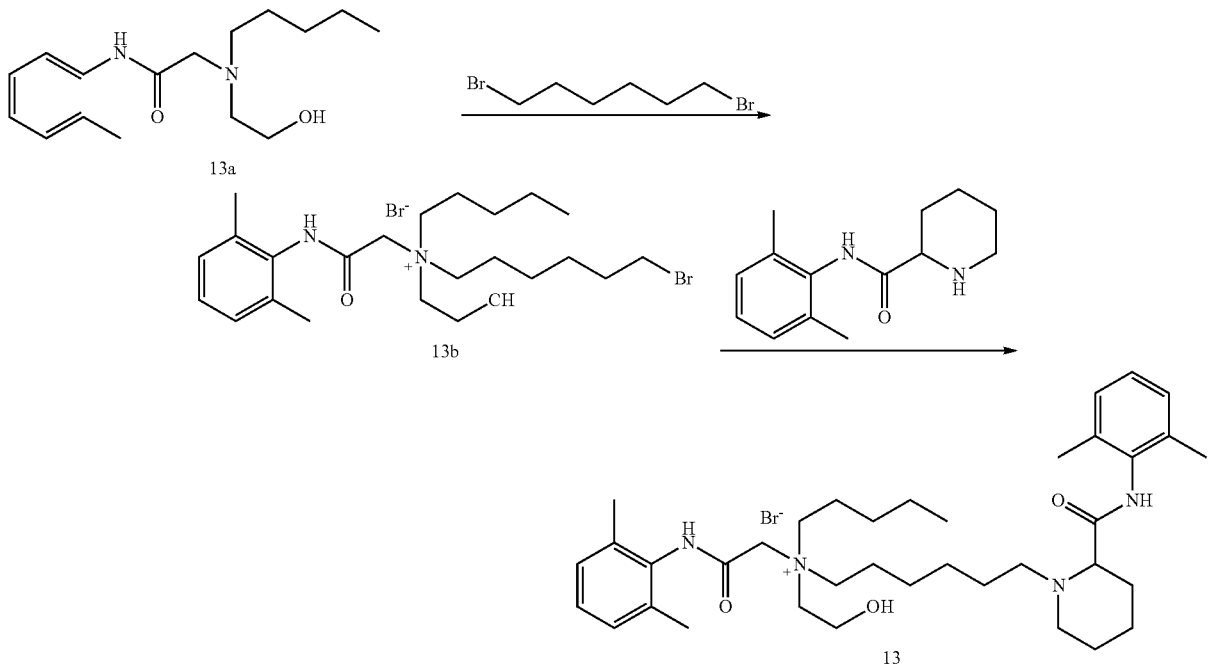

With reference to the method in Example 6, an off-white solid powder was obtained, with a yield of 37.0%.

$^1$H NMR (300 MHz, CDCl$_3$) δ (ppm): 10.28 (s, 1H), 9.99 (s, 1H), 7.30 (m, 6H), 4.31 (s, 1H), 4.24 (s, 2H), 3.95 (m, 2H), 3.40-3.46 (m, 3H), 3.24-3.16 (m, 4H), 2.47-2.41 (m, 4H), 2.12 (s, 12H), 1.90-1.63 (m, 6H), 1.57-1.28 (m, 14H), 0.88 (t, 3H). HRMS: m/z 607.9031 [C$_{37}$H$_{59}$N$_4$O$_3$]$^+$.

Example 14 Preparation of the Compound According to the Present Invention

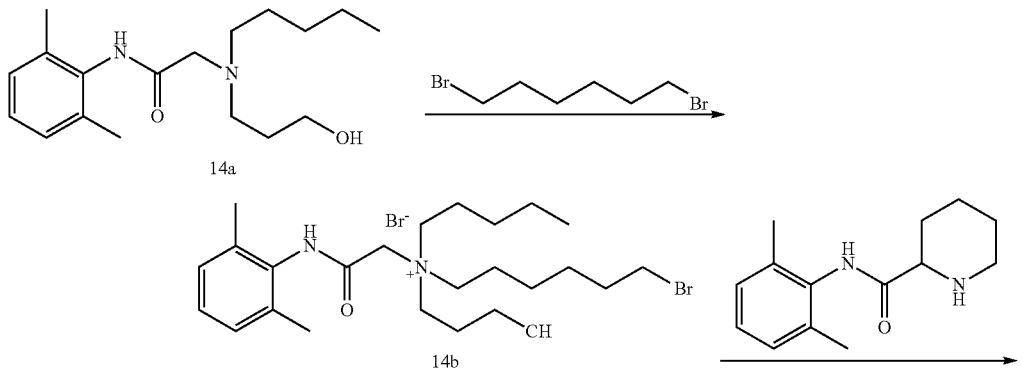

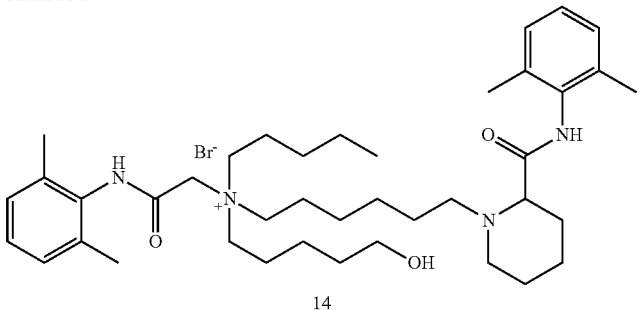

14

With reference to the method in Example 6, an off-white solid powder was obtained, with a yield of 38.9%.

$^1$H NMR (300 MHz, CDCl$_3$) δ (ppm): 10.07 (s, 1H), 9.73 (s, 1H), 7.11 (m, 6H), 4.38 (s, 1H), 4.18 (s, 2H), 3.42-3.52 (m, 3H), 3.26-3.14 (m, 6H), 2.47-2.41 (m, 4H), 2.15 (s, 12H), 1.93-1.68 (m, 8H), 1.55-1.27 (m, 14H), 0.86 (t, 3H). HRMS: m/z 621.9341 [C$_{38}$H$_{61}$N$_4$O$_3$]$^+$.

Example 15 Preparation of the Compound According to the Present Invention

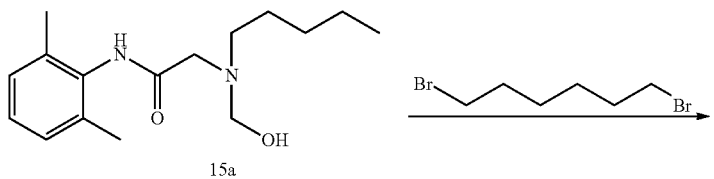

15a

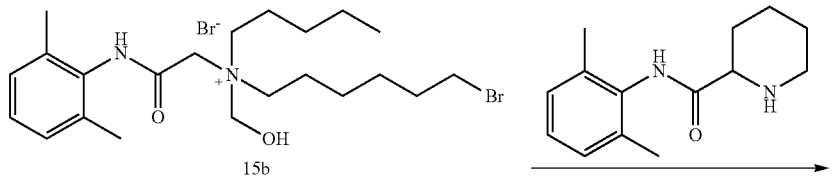

15b

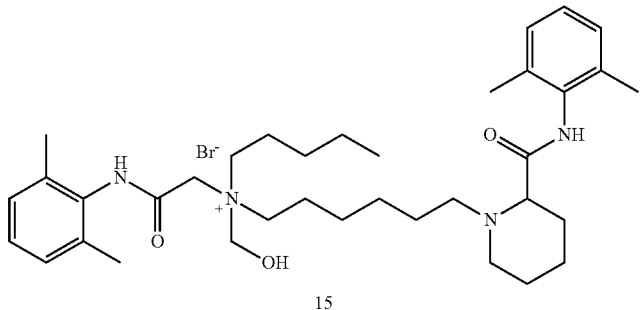

15

With reference to the method in Example 6, an off-white solid powder was obtained, with a yield of 33.2%.

$^1$H NMR (300 MHz, CDCl$_3$) δ (ppm): 10.28 (s, 1H), 9.98 (s, 1H), 7.32 (m, 6H), 5.47 (s, 2H), 4.23 (s, 2H), 4.12 (s, 1H), 3.40-3.44 (t, 1H), 3.24-3.17 (m, 4H), 2.43-2.38 (m, 4H), 2.12 (s, 12H), 1.90-1.63 (m, 6H), 1.57-1.28 (m, 14H), 0.88 (t, 3H). HRMS: m/z 593.8762 [C$_{36}$H$_{57}$N$_4$O$_3$]$^+$.

Example 16 Preparation of the Compound According to the Present Invention
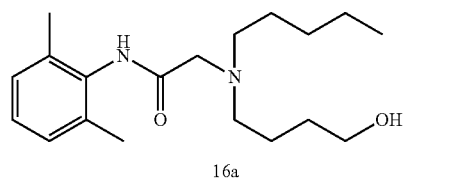 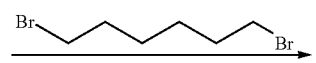
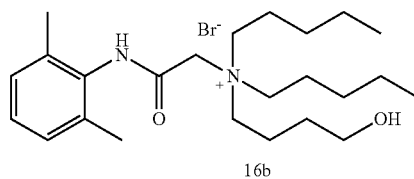 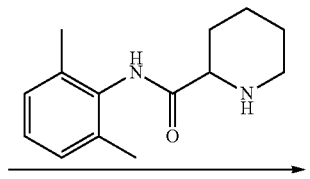
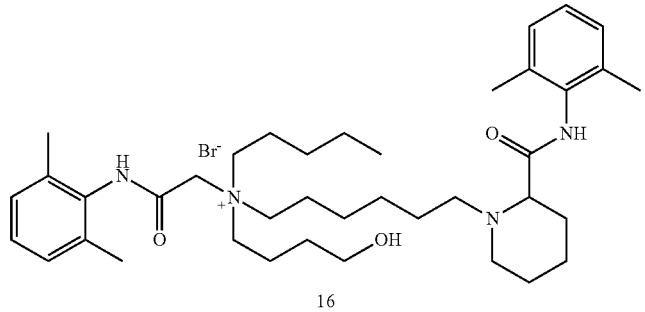
With reference to the method in Example 6, an off-white solid powder was obtained, with a yield of 40.2%.
$^1$H NMR (300 MHz, CDCl$_3$) δ (ppm): 10.08 (s, 1H), 9.89 (s, 1H), 7.06 (m, 6H), 4.18 (s, 2H), 4.12 (s, 1H), 3.52-3.45 (m, 3H), 3.26-3.18 (m, 6H), 2.53-2.39 (m, 4H), 2.16 (s, 12H), 2.05 (m, 2H), 1.90-1.72 (m, 6H), 1.61-1.28 (m, 16H), 0.92-0.87 (m, 3H). HRMS: m/z 635.9577 [C$_{39}$H$_{63}$N$_4$O$_3$]$^+$.
Example 17 Preparation of the Compound According to the Present Invention
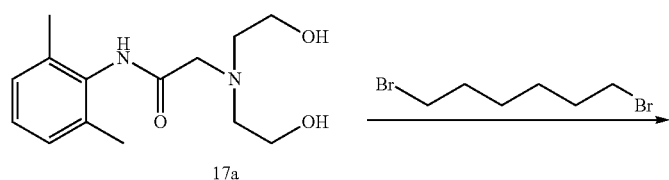 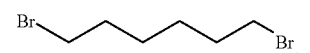
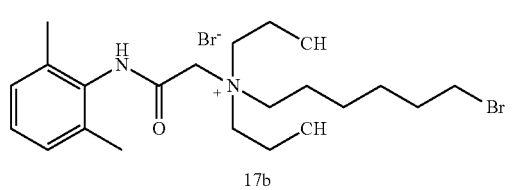 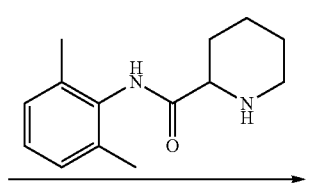

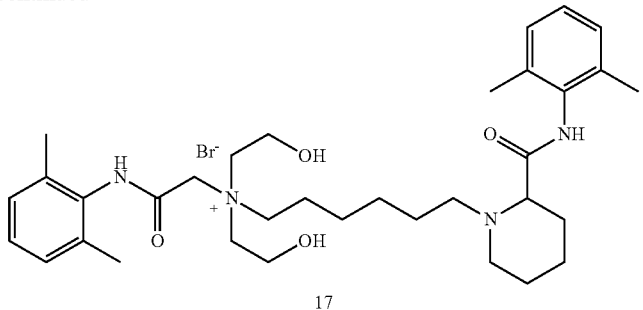
With reference to the method in Example 6, an off-white solid powder was obtained, with a yield of 36.1%.
$^1$H NMR (300 MHz, CDCl$_3$) δ (ppm): 10.11 (s, 1H), 9.88 (s, 1H), 7.05 (m, 6H), 4.28 (s, 2H), 4.15 (s, 2H), 3.97-3.84 (m, 4H), 3.51-3.42 (m, 5H), 3.26-3.11 (m, 2H), 2.47-2.32 (m, 4H), 2.16 (s, 12H), 1.92-1.72 (m, 4H), 1.63-1.28 (m, 10H). HRMS: m/z 581.8216 [C$_{34}$H$_{53}$N$_4$O$_4$]$^+$.
Example 18 Preparation of the Compound According to the Present Invention
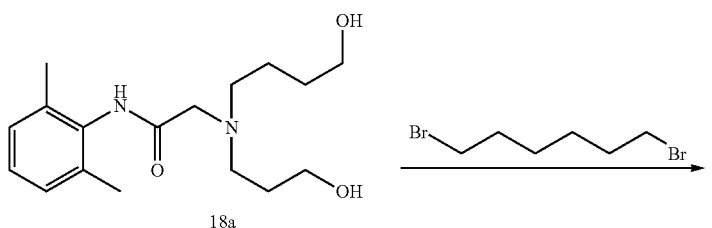
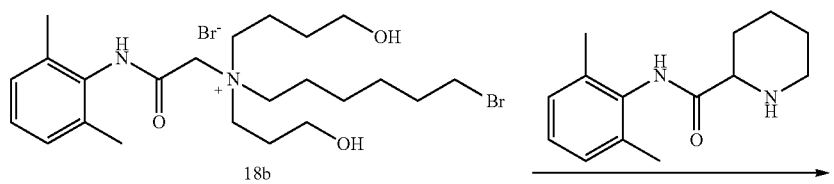
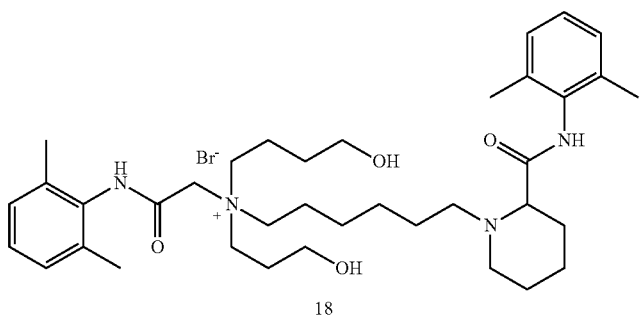

With reference to the method in Example 6, an off-white solid powder was obtained, with a yield of 36.1%.

$^1$H NMR (300 MHz, CDCl$_3$) δ (ppm): 9.96 (s, 1H), 9.72 (s, 1H), 7.02 (m, 6H), 4.28 (s, 1H), 4.18 (m, 2H), 4.14 (s, 1H), 3.51-3.42 (m, 5H), 3.21-3.11 (m, 6H), 2.47-2.30 (m, 4H), 2.15 (s, 12H), 1.97-1.71 (m, 8H), 1.66-1.26 (m, 12H). HRMS: m/z 623.9029 [C$_{37}$H$_{59}$N$_4$O$_4$]$^+$.

Example 19 Preparation of the Compound According to the Present Invention

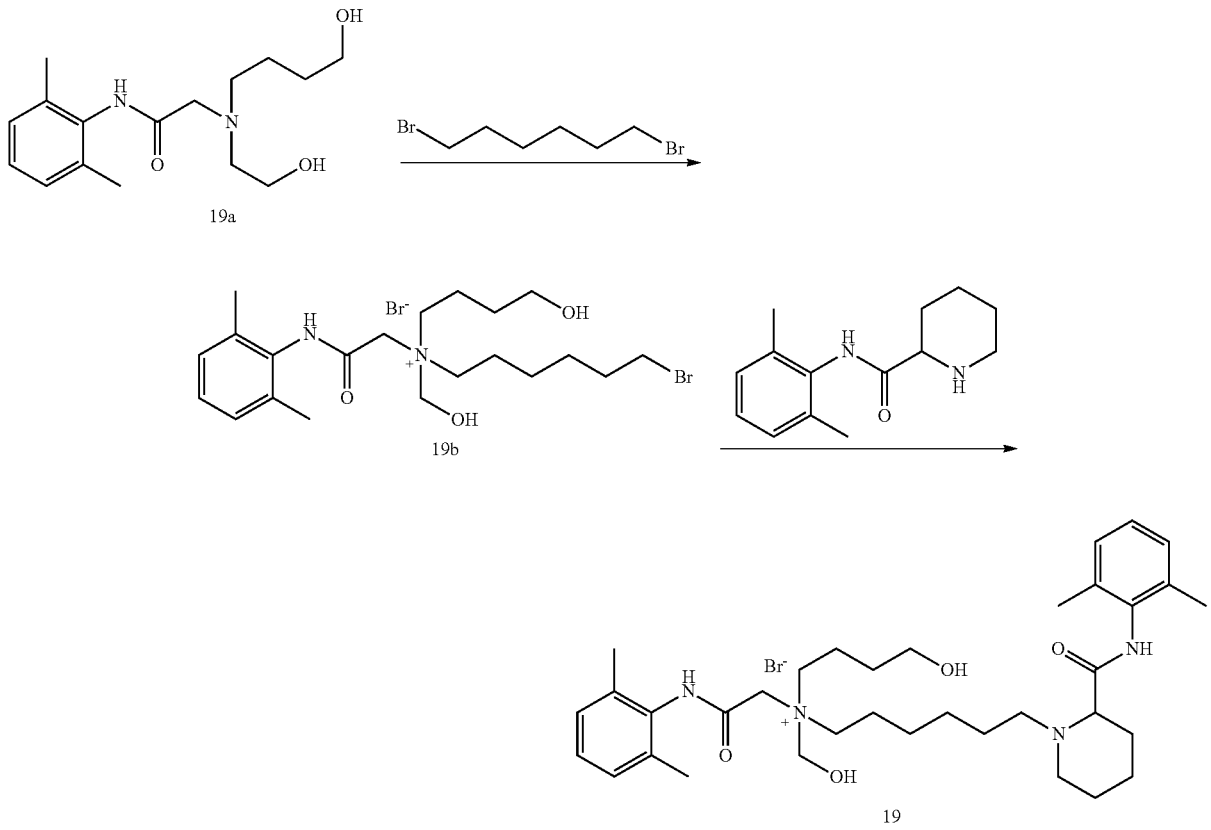

With reference to the method in Example 6, an off-white solid powder was obtained, with a yield of 42.2%.

$^1$H NMR (300 MHz, CDCl$_3$) δ (ppm): 10.02 (s, 1H), 9.87 (s, 1H), 7.03 (m, 6H), 5.48 (s, 2H), 4.18 (s, 2H), 4.15 (s, 2H), 3.52-3.45 (m, 3H), 3.26-3.18 (m, 4H), 2.47-2.39 (m, 4H), 2.16 (s, 12H), 1.92-1.73 (m, 6H), 1.57-1.28 (m, 12H). HRMS: m/z 675.7533 [C$_{35}$H$_{55}$N$_4$O$_4$]$^+$.

Example 20 Preparation of the Compound According to the Present Invention

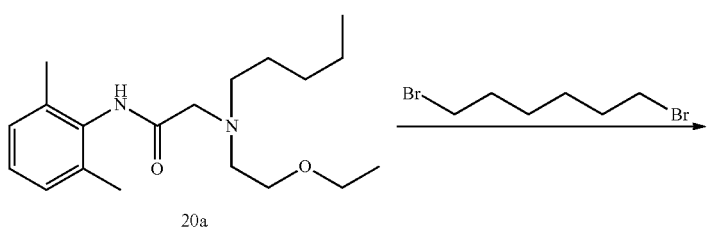

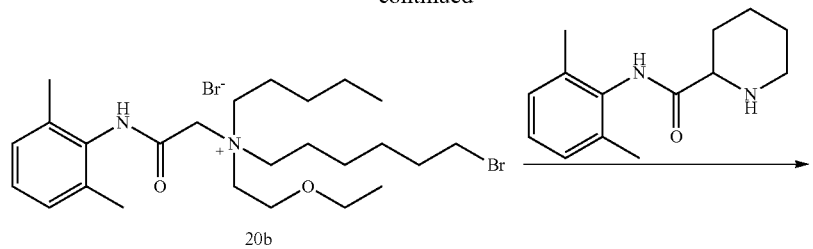
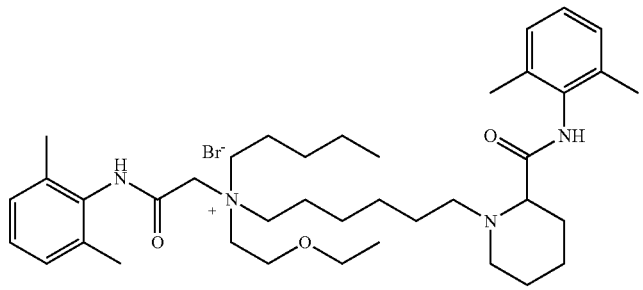
With reference to the method in Example 5, an off-white solid powder was obtained, with a yield of 33.6%.
$^1$H NMR (300 MHz, CDCl$_3$) δ (ppm): 10.01 (s, 1H), 9.88 (s, 1H), 7.08-6.98 (m, 6H), 4.25 (s, 2H), 3.81 (t, 2H), 3.51-3.28 (m, 5H), 3.21-2.99 (m, 4H), 2.52-2.41 (m, 4H), 2.13-1.98 (m, 12H), 1.85-1.65 (m, 6H), 1.53-1.14 (m, 14H), 1.04 (t, 3H), 0.87 (t, 3H). HRMS: m/z 635.9579 [C$_{39}$H$_{63}$N$_4$O$_3$]$^+$.
Example 21 Preparation of the Compound According to the Present Invention
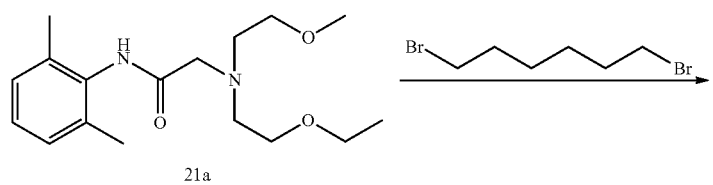
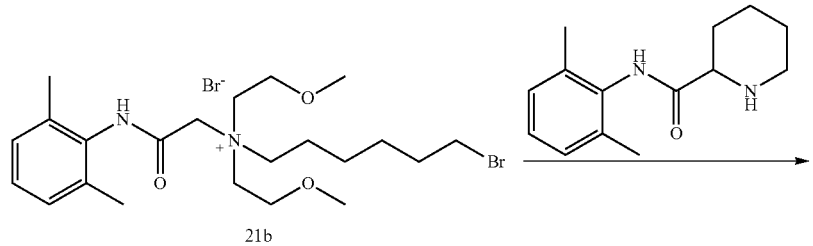
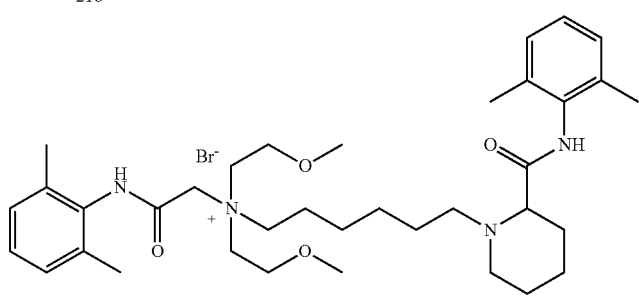

With reference to the method in Example 5, a white solid powder was obtained, with a yield of 28.5%.

$^1$H NMR (300 MHz, CDCl$_3$) δ (ppm): 10.08 (s, 1H), 9.75 (s, 1H), 7.06-6.93 (m, 6H), 4.53 (s, 2H), 3.84-3.78 (m, 4H), 3.42-3.28 (m, 5H), 3.05-2.96 (m, 8H), 2.72-2.49 (m, 4H), 2.16-1.90 (m, 12H), 1.80-1.63 (m, 4H), 1.53-1.12 (m, 10H). HRMS: m/z 689.7804 [C$_{36}$H$_{57}$N$_4$O$_4$]$^+$.

Example 22 Preparation of the Compound According to the Present Invention

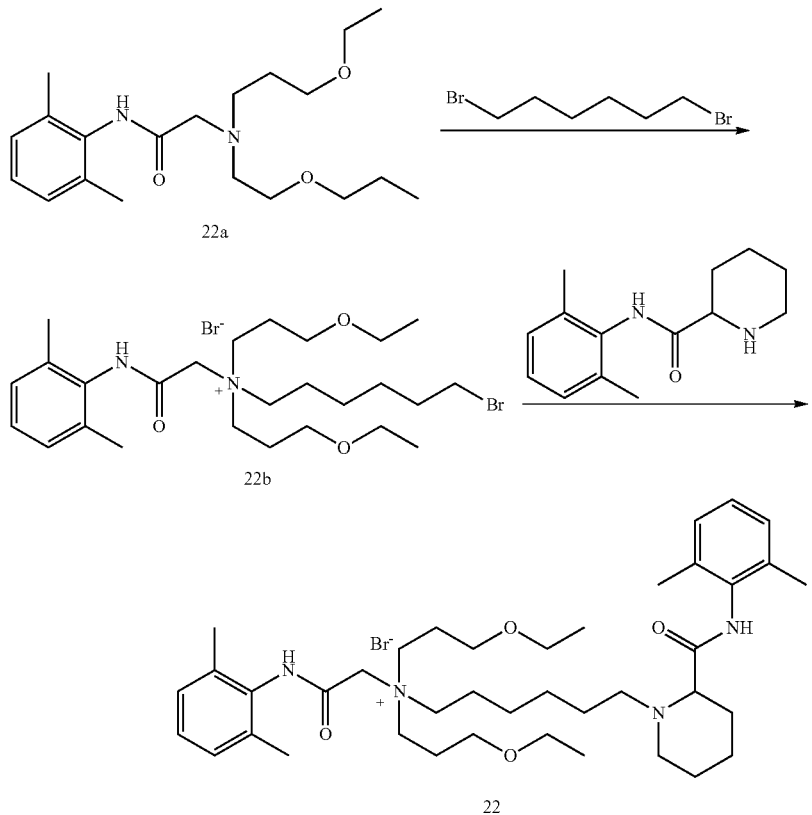

With reference to the method in Example 5, a white solid powder was obtained, with a yield of 30.2%.

$^1$H NMR (300 MHz, CDCl$_3$) δ (ppm): 9.92 (s, 1H), 8.76 (s, 1H), 7.06-6.90 (m, 6H), 4.53 (s, 2H), 3.41-3.22 (m, 9H), 3.07-2.95 (m, 6H), 2.66-2.42 (m, 4H), 2.16-1.92 (m, 12H), 1.80-1.63 (m, 8H), 1.53-1.12 (m, 10H), 1.05-0.89 (m, 6H). HRMS: m/z 665.9831 [C$_{40}$H$_{65}$N$_4$O$_4$]$^+$.

Example 23 Preparation of the Compound According to the Present Invention

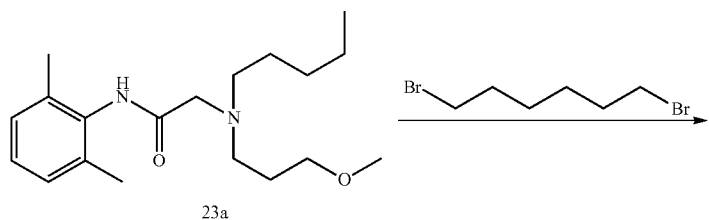

-continued
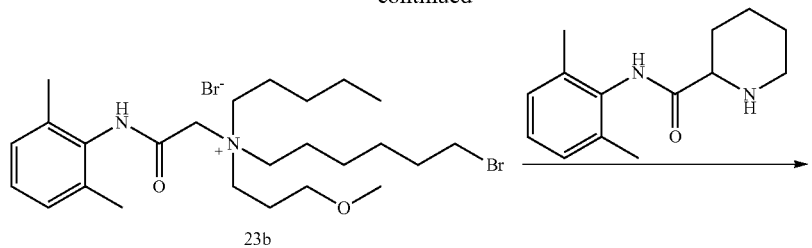
23b
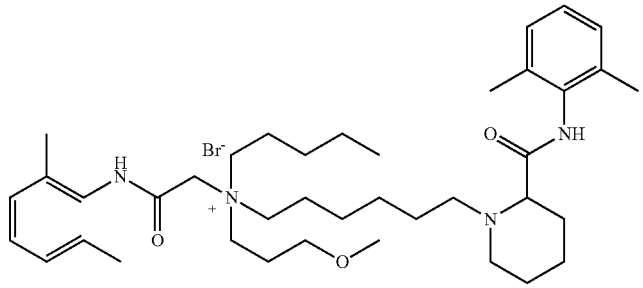
23
With reference to the method in Example 5, an off-white solid powder was obtained, with a yield of 35.2%.
$^1$H NMR (300 MHz, CDCl$_3$) δ (ppm): 10.02 (s, 1H), 9.65 (s, 1H), 7.08-6.98 (m, 6H), 4.25 (s, 2H), 3.50-3.33 (m, 3H), 3.26-3.08 (m, 9H), 2.48-2.36 (m, 4H), 2.16-2.05 (m, 12H), 1.85-1.65 (m, 8H), 1.52-1.17 (m, 14H), 0.88 (t, 3H). HRMS: m/z 635.9571 [C$_{39}$H$_{63}$N$_4$O$_3$]$^+$.
Example 24 Preparation of the Compound According to the Present Invention
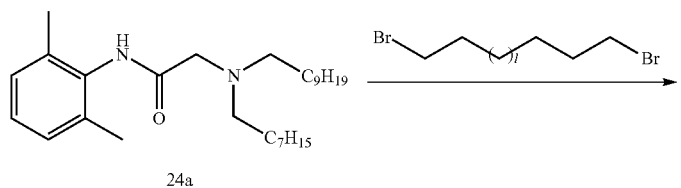
24a
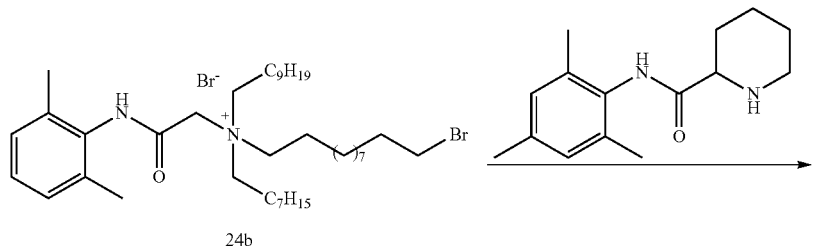
24b
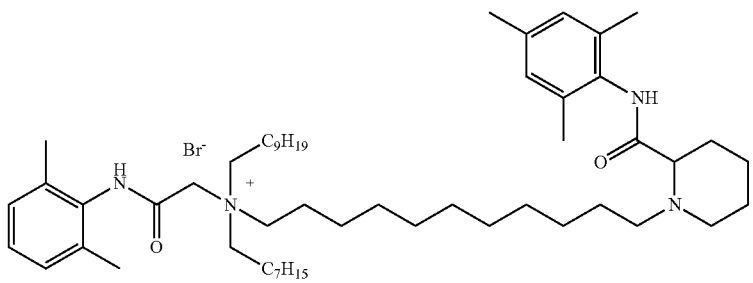
24

With reference to the method in Example 3, a white solid powder was obtained, with a yield of 43.2%.

$^1$H NMR (300 MHz, CDCl$_3$) δ (ppm): 10.04 (s, 1H), 9.39 (s, 1H), 7.05-6.88 (m, 5H), 4.38 (s, 2H), 3.65-3.54 (m, 4H), 3.33-3.09 (m, 3H), 2.45-2.32 (m, 4H), 2.29 (s, 3H), 2.18-2.15 (m, 12H), 2.05-1.83 (m, 8H), 1.48-1.20 (m, 44H), 1.01-0.83 (m, 6H). HRMS: m/z 830.3031 [C$_{54}$H$_{93}$N$_4$O$_2$]$^+$.

Example 25 Preparation of the Compound According to the Present Invention

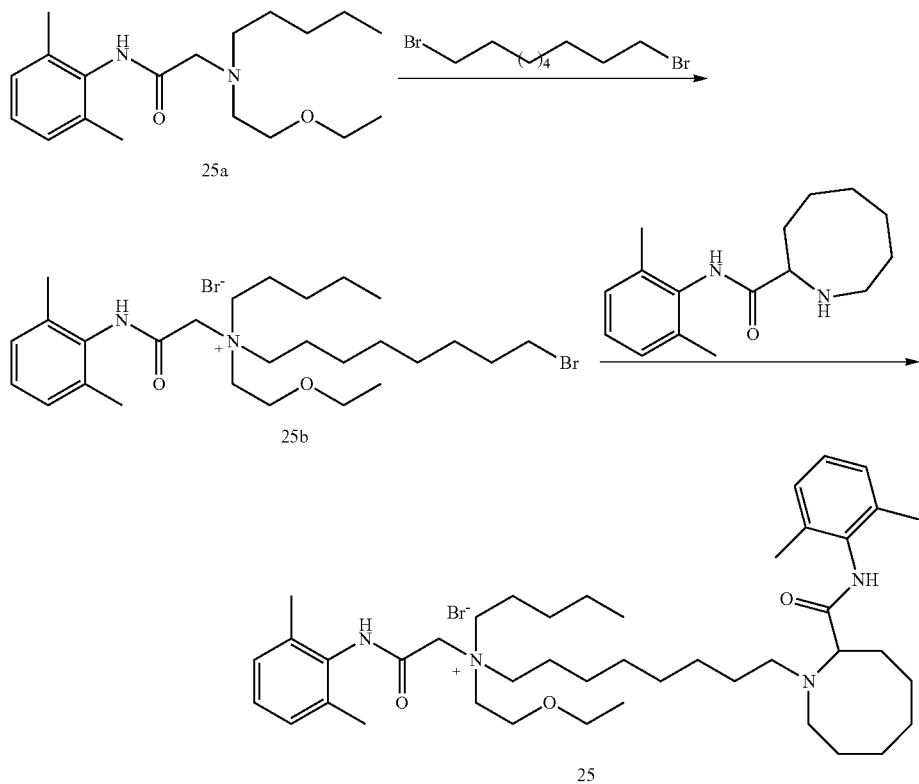

With reference to the method in Example 5, an off-white solid powder was obtained, with a yield of 30.1%.

$^1$H NMR (300 MHz, CDCl$_3$) δ (ppm): 10.01 (s, 1H), 9.88 (s, 1H), 7.08-6.98 (m, 6H), 4.25 (s, 2H), 3.81 (t, 2H), 3.65 (t, 1H), 3.51-3.42 (m, 4H), 3.31-3.13 (m, 4H), 2.52-2.21 (m, 4H), 2.14-2.02 (m, 12H), 1.85-1.49 (m, 6H), 1.43-1.14 (m, 22H), 1.05 (t, 3H), 0.88 (t, 3H). HRMS: m/z 692.0656 [C$_{43}$H$_{71}$N$_4$O$_3$]$^+$.

Example 26 Preparation of the Compound According to the Present Invention

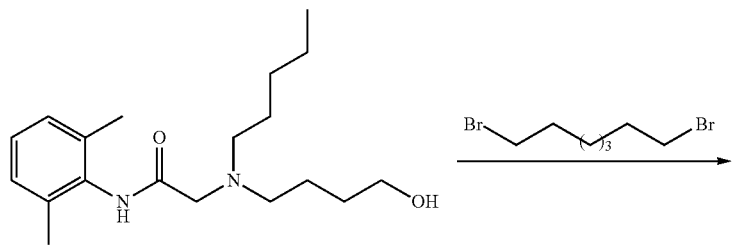

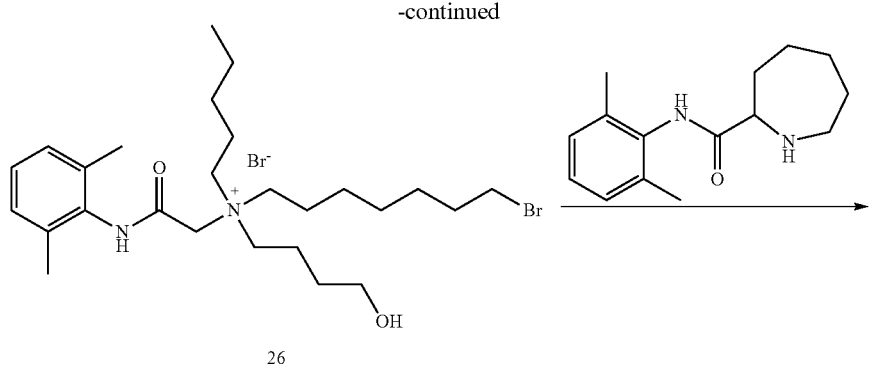
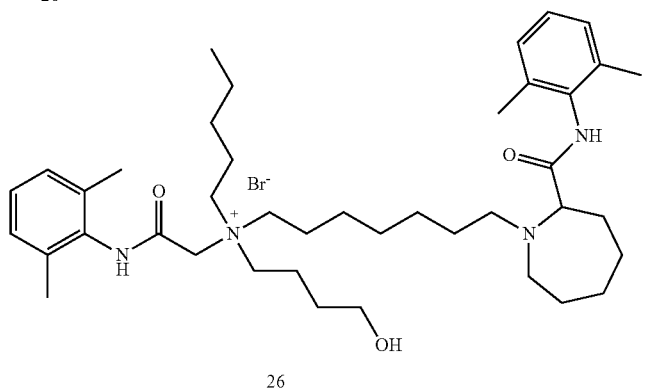
With reference to the method in Example 6, an off-white solid powder was obtained, with a yield of 38.2%.
$^1$H NMR (300 MHz, CDCl$_3$) δ (ppm): 9.75 (s, 1H), 7.98 (s, 1H), 7.05 (m, 6H), 4.21 (s, 2H), 4.12 (s, 1H), 3.63 (t, 1H), 3.52-3.45 (m, 2H), 3.26-3.18 (m, 6H), 2.53-2.39 (m, 4H), 2.16 (s, 12H), 1.90-1.72 (m, 10H), 1.61-1.28 (m, 18H), 0.92-0.87 (m, 3H). HRMS: m/z 664.0112 [C$_{41}$H$_{67}$N$_4$O$_3$]$^+$.
Example 27 Preparation of the Compound According to the Present Invention
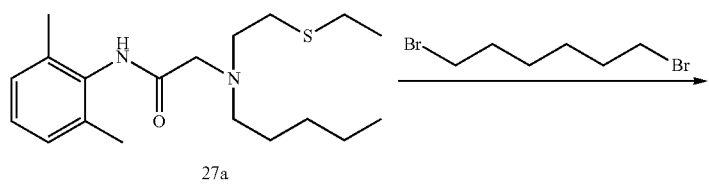
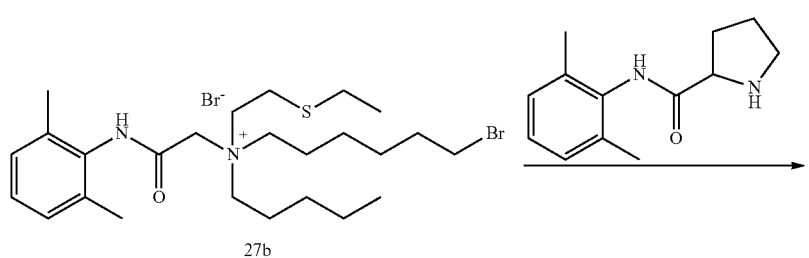

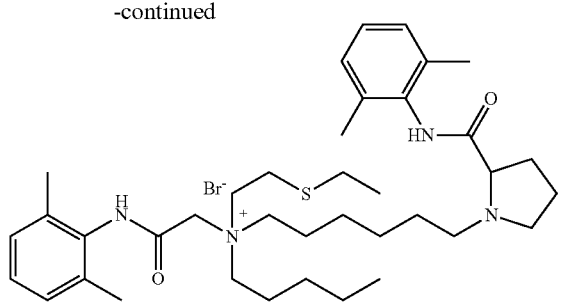
27
With reference to the method in Example 7, an off-white solid powder was obtained, with a yield of 35.8%.
$^1$H NMR (300 MHz, CDCl$_3$) δ (ppm): 9.76 (s, 1H), 8.29 (s, 1H), 7.18-7.01 (m, 6H), 4.85 (s, 2H), 3.61 (t, 2H), 3.45 (t, 1H), 3.31-3.24 (m, 4H), 2.86 (t, 2H), 2.43-2.18 (m, 6H), 2.15-2.10 (m, 12H), 2.05-1.76 (m, 8H), 1.60-1.22 (m, 10H), 1.15 (t, 3H), 0.86 (t, 3H). HRMS: m/z 637.9918 [C$_{38}$H$_{61}$N$_4$O$_2$S]$^+$.
Example 28 Preparation of the Compound According to the Present Invention
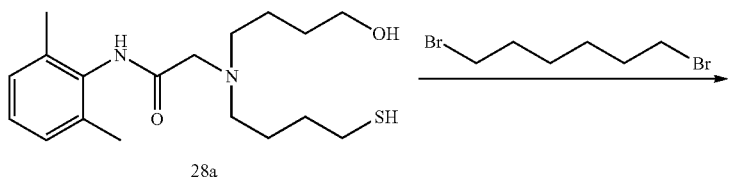
28a
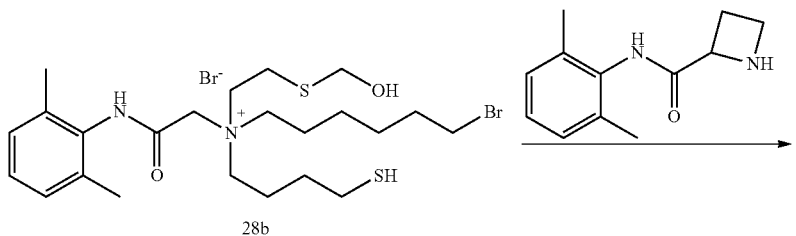
28b
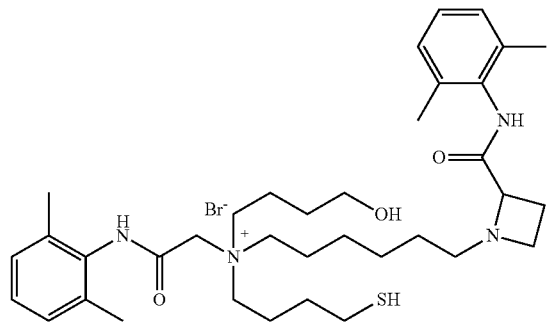
28

With reference to the method in Example 8, an off-white solid powder was obtained, with a yield of 35.8%.
$^1$H NMR (300 MHz, CDCl$_3$) δ (ppm): 10.02 (s, 1H), 9.89 (s, 1H), 7.23-6.87 (m, 6H), 4.33-4.14 (m, 4H), 3.60-3.49 (m, 4H), 3.33-3.28 (m, 6H), 2.63-2.39 (m, 6H), 2.15-2.11 (m, 12H), 1.93-1.75 (m, 6H), 1.49-1.31 (m, 4H), 1.30-1.15 (m, 7H). HRMS: [C$_{36}$H$_{57}$ClN$_4$O$_3$S]$^+$, 625.9327.
Example 29 Preparation of the Compound According to the Present Invention
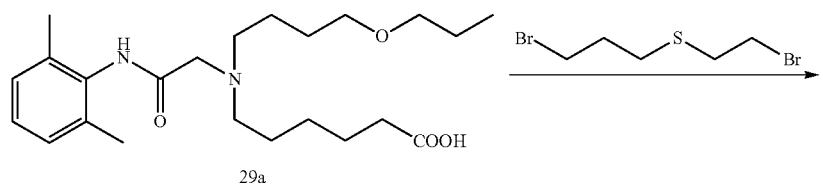
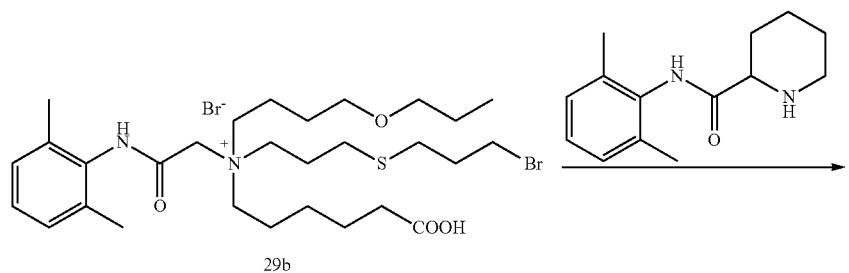
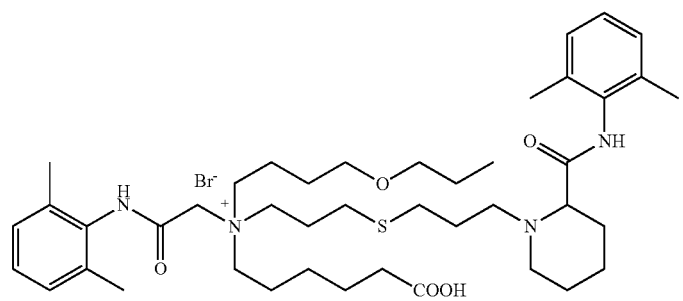

With reference to the method in Example 2, an off-white solid powder was obtained, with a yield of 35.8%.

$^{1}$H NMR (300 MHz, CDCl$_3$) δ (ppm): 11.88 (s, 1H), 9.79 (s, 1H), 8.78 (s, 1H), 7.09-6.98 (m, 6H), 4.25 (s, 2H), 3.52-3.40 (m, 5H), 3.27-3.21 (m, 4H), 2.54-2.36 (m, 8H), 2.22-2.07 (s, 16H), 1.89-1.74 (m, 6H), 1.60-1.40 (m, 10H), 1.40-1.20 (m, 6H), 0.98 (t, 3H). HRMS: m/z 754.1078 [C$_{43}$H$_{69}$N$_4$O$_5$]$^+$.

Example 30 Preparation of the Compound According to the Present Invention

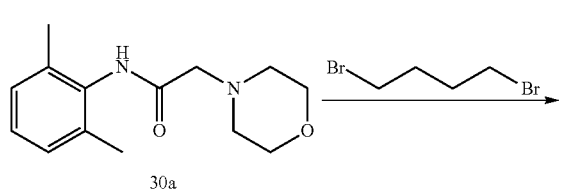

30a

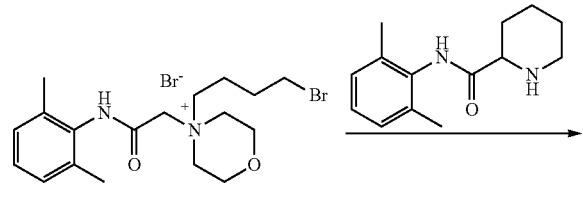

30b

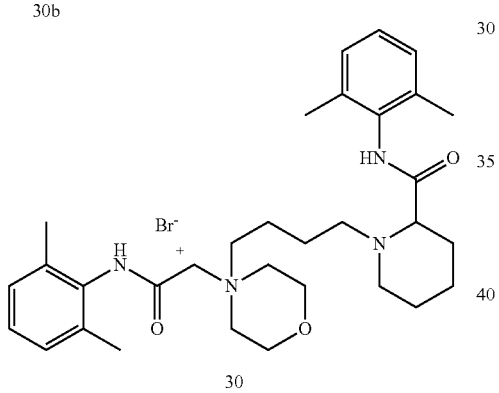

30

With reference to the method in Example 1, an off-white solid powder was obtained, with a yield of 36.3%.

$^{1}$H NMR (300 MHz, CDCl$_3$) δ (ppm): 10.35 (s, 1H), 9.70 (s, 1H), 7.11-7.02 (m, 6H), 4.26 (s, 2H), 3.88-3.67 (m, 4H), 3.68-3.45 (m, 5H), 2.71-2.57 (m, 6H), 2.28-2.17 (m, 12H), 1.90-1.63 (m, 4H), 1.60-1.27 (m, 6H). HRMS: m/z 535.7521 [C$_{32}$H$_{47}$N$_4$O$_3$]$^+$.

Example 31 Preparation of the Compound According to the Present Invention

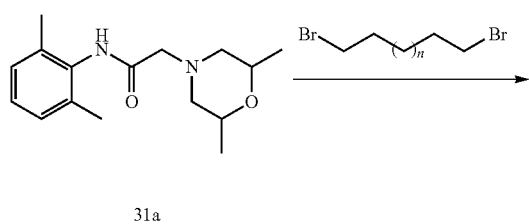

31a

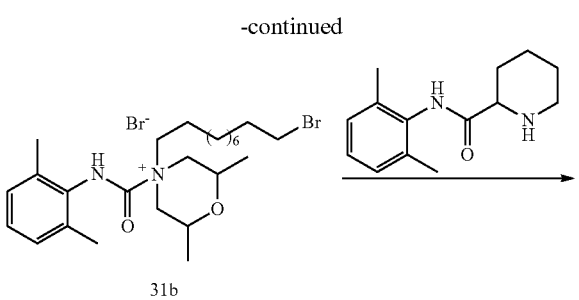

31b

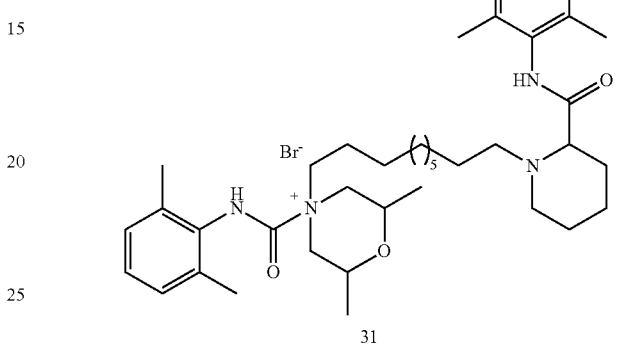

31

With reference to the method in Example 1, an off-white solid powder was obtained, with a yield of 34.2%.

$^{1}$H NMR (300 MHz, CDCl$_3$) δ (ppm): 9.72 (s, 1H), 8.60 (s, 1H), 7.07-7.02 (m, 6H), 4.18 (s, 2H), 4.02 (m, 2H), 3.54-3.33 (m, 7H), 2.52-2.38 (m, 4H), 2.18-2.06 (m, 12H), 1.90-1.63 (m, 4H), 1.60-1.27 (m, 18H), 1.12-1.03 (m, 6H). HRMS: m/z 647.9683 [C$_{40}$H$_{63}$N$_4$O$_3$]$^+$.

Example 32 Preparation of the Compound According to the Present Invention

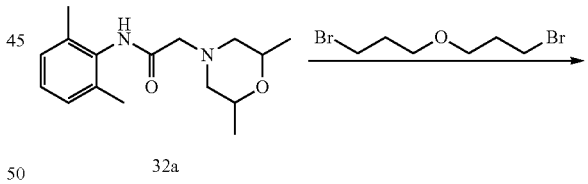

32a

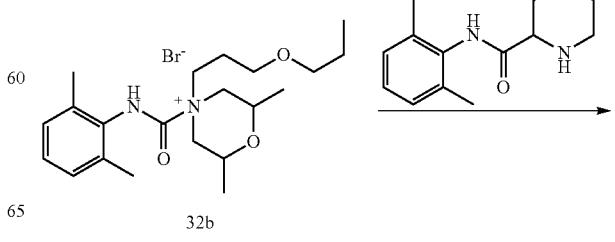

32b

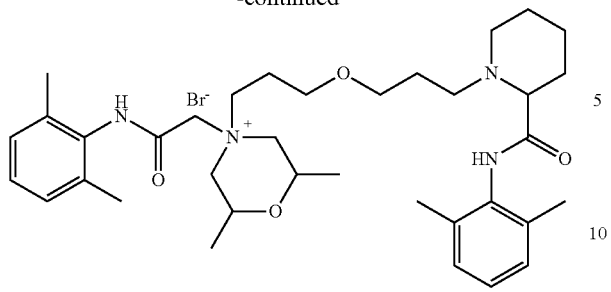

32

With reference to the method in Example 2, an off-white solid powder was obtained, with a yield of 28.5%.

$^1$H NMR (300 MHz, CDCl$_3$) δ (ppm): 10.02 (s, 1H), 9.35 (s, 1H), 7.11-7.01 (m, 6H), 4.20 (s, 2H), 4.03 (m, 2H), 3.51-3.35 (m, 11H), 2.45-2.39 (m, 4H), 2.15-2.11 (m, 12H), 1.99-1.72 (m, 4H), 1.57-1.41 (m, 6H), 1.18-1.13 (m, 6H). HRMS: m/z 607.8599 [C$_{36}$H$_{55}$N$_4$O$_4$]$^+$.

Example 33 Preparation of the Compound According to the Present Invention

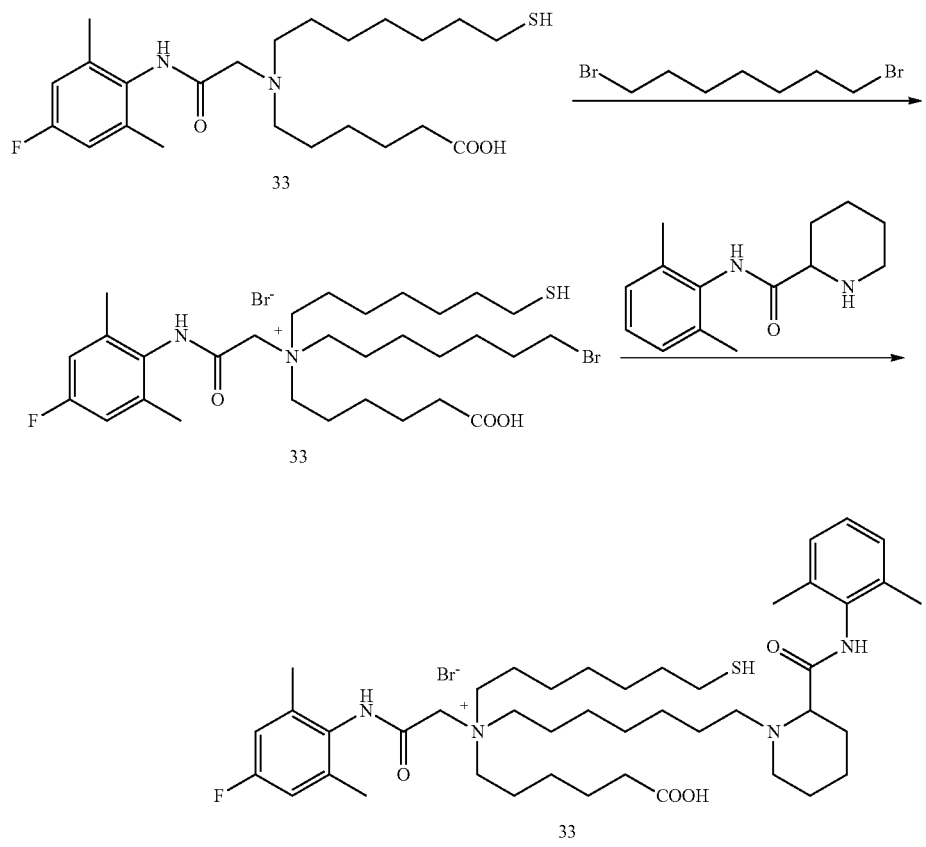

With reference to the method in Example 3, an off-white solid powder was obtained, with a yield of 39.1%.

$^1$H NMR (300 MHz, CDCl$_3$) δ (ppm): 11.87 (s, 1H), 10.02 (s, 1H), 9.69 (s, 1H), 7.04 (s, 3H), 6.91-6.85 (m, 2H), 4.27 (s, 2H), 3.51-3.29 (m, 7H), 2.66-2.45 (m, 6H), 2.31-2.18 (m, 2H), 2.12 (d, 12H), 1.98-1.63 (m, 12H), 1.60-1.27 (m, 21H). HRMS: m/z 770.1255 [C$_{44}$H$_{70}$FN$_4$O$_4$S]$^+$.

Example 34 Preparation of the Compound According to the Present Invention

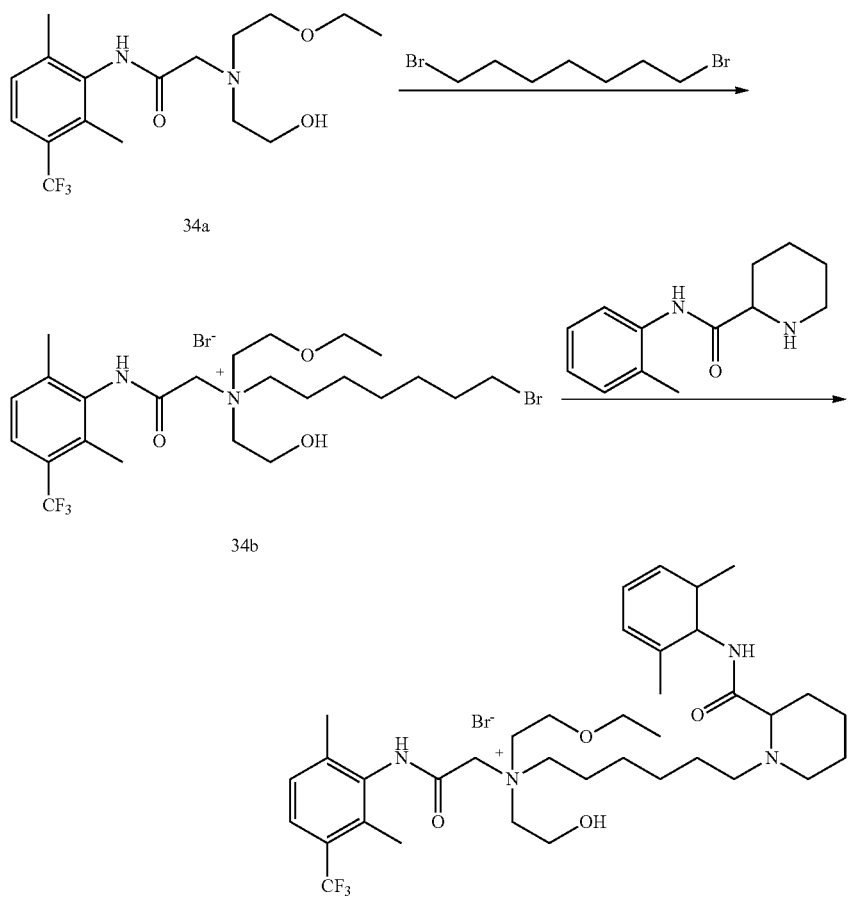

With reference to the method in Example 5, an off-white solid powder was obtained, with a yield of 33.4%.

$^1$H NMR (300 MHz, CDCl$_3$) δ (ppm): 10.06 (s, 1H), 9.77 (s, 1H), 7.18-7.01 (m, 3H), 6.85-6.74 (m, 2H), 4.24 (s, 1H), 3.97 (t, 2H), 3.81 (t, 2H), 3.58-3.16 (m, 11H), 2.43-2.18 (m, 4H), 2.15-2.10 (m, 12H), 2.05-1.76 (m, 4H), 1.61-1.29 (m, 10H), 1.05 (t, 3H). HRMS: m/z 677.8732 [C$_{37}$H$_{56}$F$_3$N$_4$O$_4$]$^+$.

According to the Preparative Method of the Above Examples, the Following Compounds 35 to 76 (Corresponding to Example 35 to Example 76) were Also Prepared

| Structure | Molecular and molecular weight in MS |
|---|---|
| 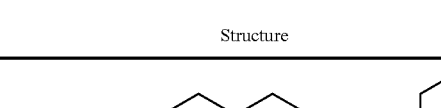 35 | HRMS: [C$_{38}$H$_{61}$N$_4$O$_4$]$^+$: 637.9292 |

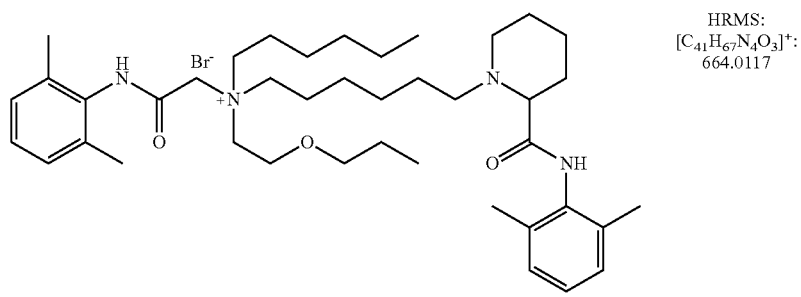
HRMS:
[C₄₁H₆₇N₄O₃]⁺:
664.0117
37
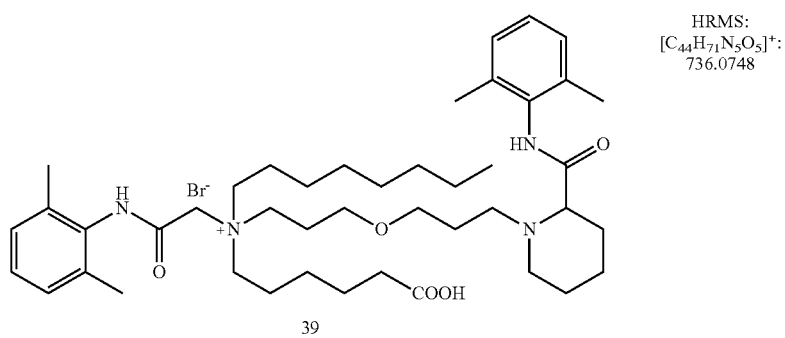
HRMS:
[C₄₄H₇₁N₅O₅]⁺:
736.0748
39
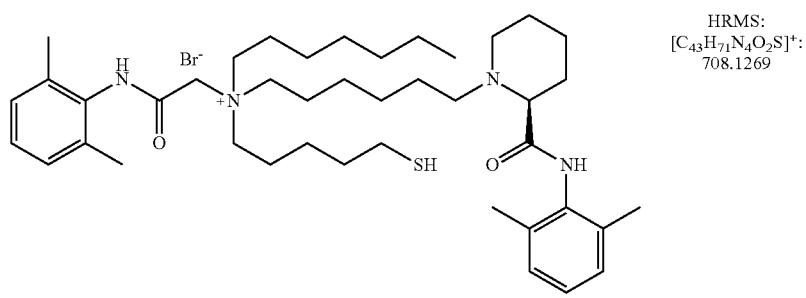
HRMS:
[C₄₃H₇₁N₄O₂S]⁺:
708.1269
41
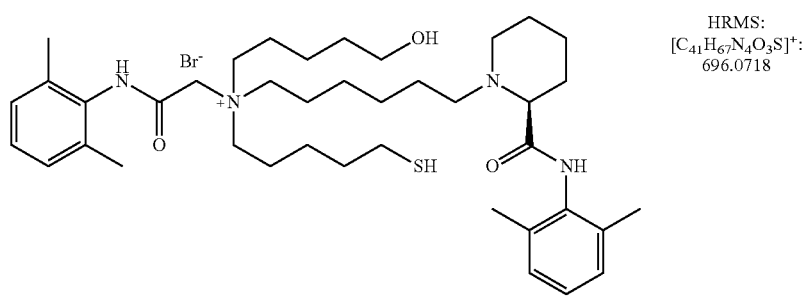
HRMS:
[C₄₁H₆₇N₄O₃S]⁺:
696.0718
43

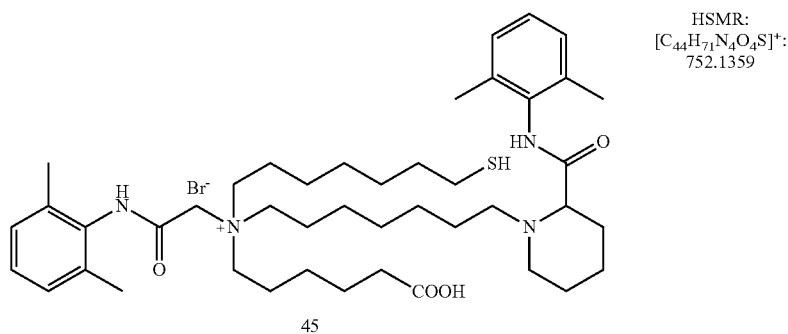
HSMR: [C$_{44}$H$_{71}$N$_4$O$_4$S]$^+$: 752.1359
45
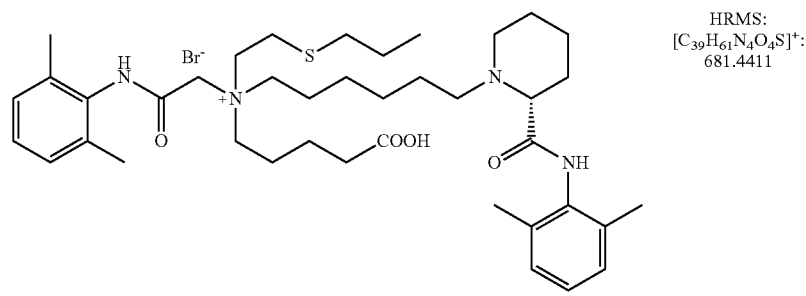
HRMS: [C$_{39}$H$_{61}$N$_4$O$_4$S]$^+$: 681.4411
47
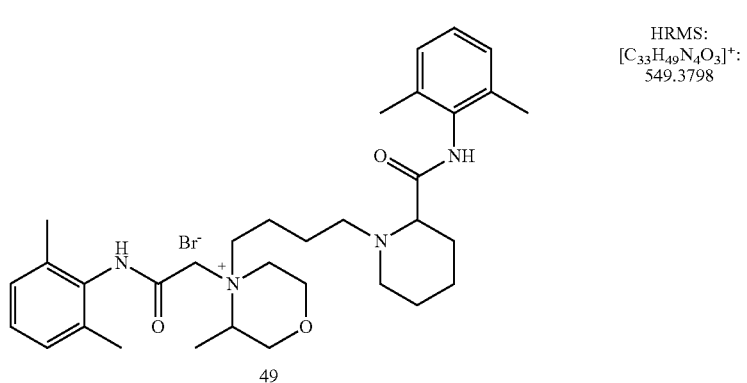
HRMS: [C$_{33}$H$_{49}$N$_4$O$_3$]$^+$: 549.3798
49
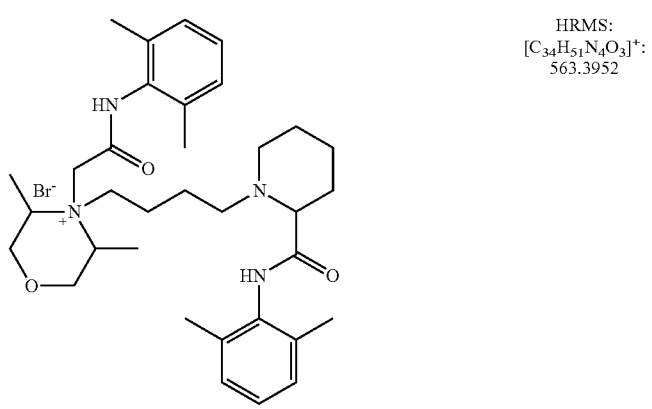
HRMS: [C$_{34}$H$_{51}$N$_4$O$_3$]$^+$: 563.3952
51

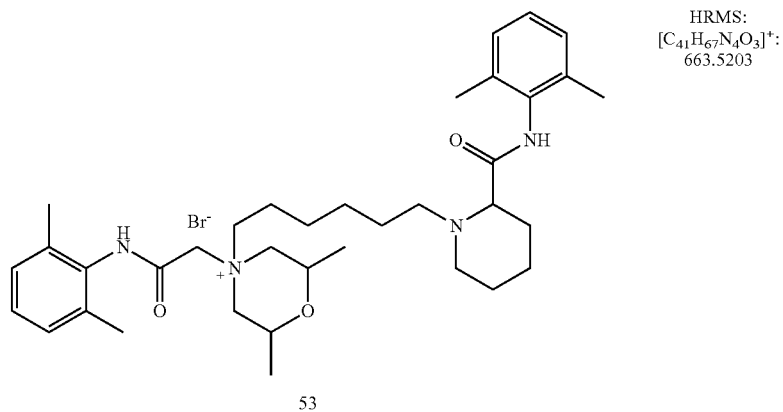
HRMS:
$[C_{41}H_{67}N_4O_3]^+$:
663.5203
53
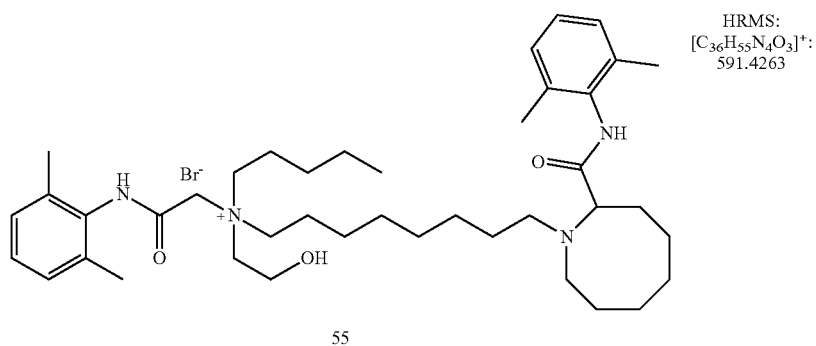
HRMS:
$[C_{36}H_{55}N_4O_3]^+$:
591.4263
55
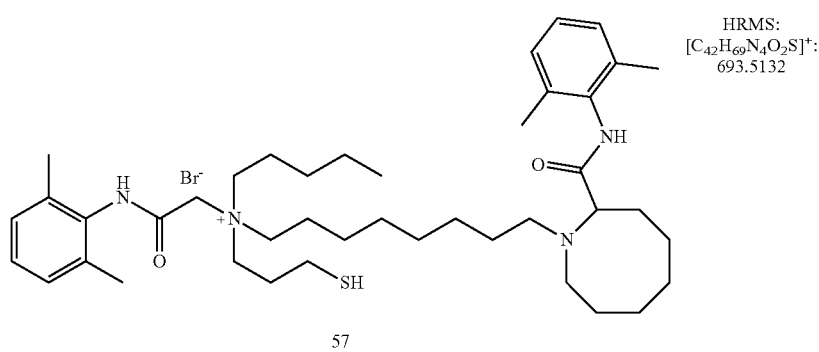
HRMS:
$[C_{42}H_{69}N_4O_2S]^+$:
693.5132
57
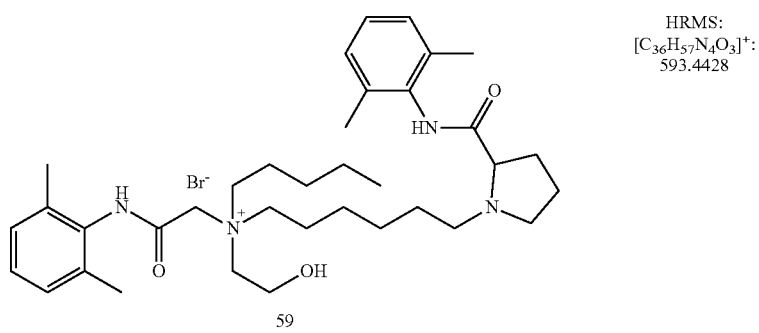
HRMS:
$[C_{36}H_{57}N_4O_3]^+$:
593.4428
59

-continued
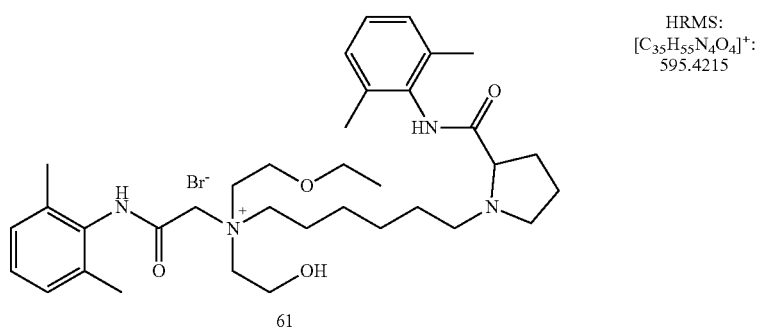
HRMS:
$[C_{35}H_{55}N_4O_4]^+$:
595.4215
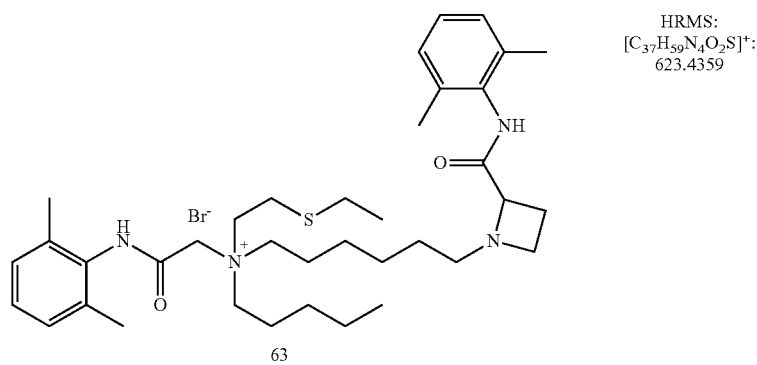
HRMS:
$[C_{37}H_{59}N_4O_2S]^+$:
623.4359
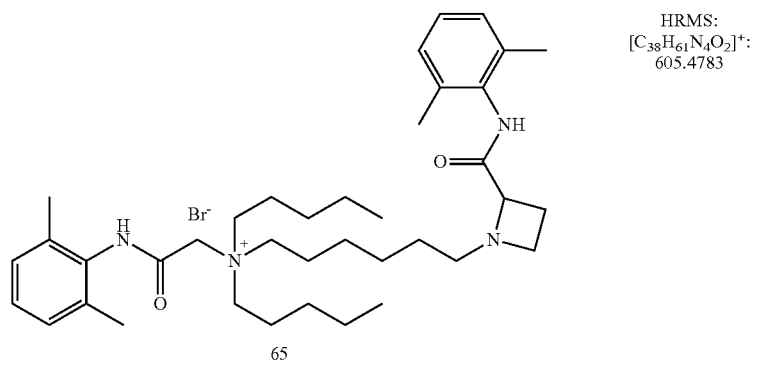
HRMS:
$[C_{38}H_{61}N_4O_2]^+$:
605.4783
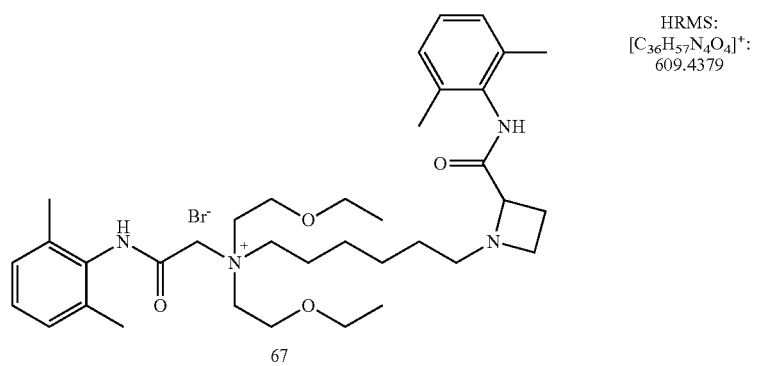
HRMS:
$[C_{36}H_{57}N_4O_4]^+$:
609.4379

-continued
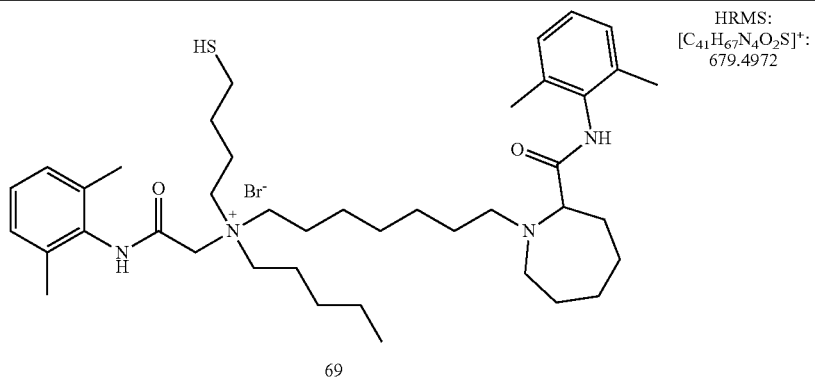
69
HRMS:
$[C_{41}H_{67}N_4O_2S]^+$:
679.4972
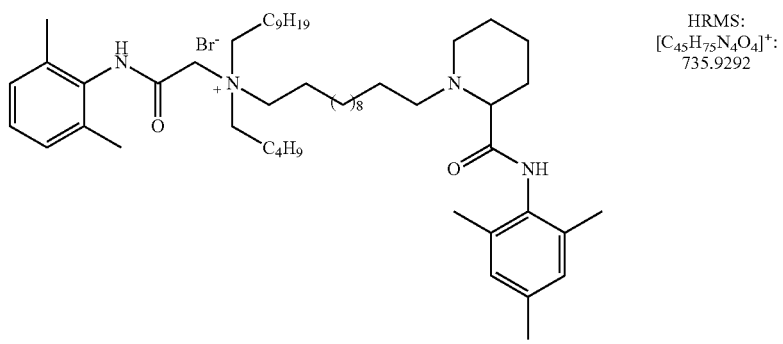
71
HRMS:
$[C_{45}H_{75}N_4O_4]^+$:
735.9292
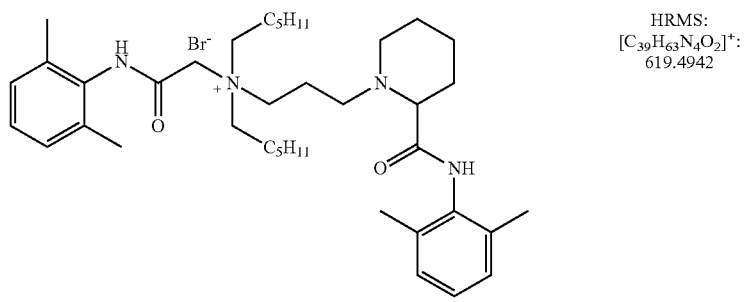
73
HRMS:
$[C_{39}H_{63}N_4O_2]^+$:
619.4942

-continued
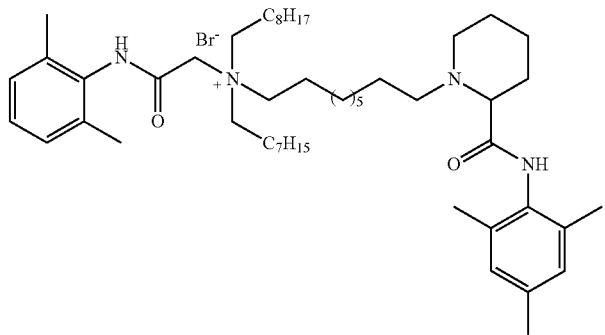
75
HRMS:
$[C_{51}H_{69}N_4O_4]^+$:
693.9292
| Structure | Molecular formula and molecular weight in MS |
|---|---|
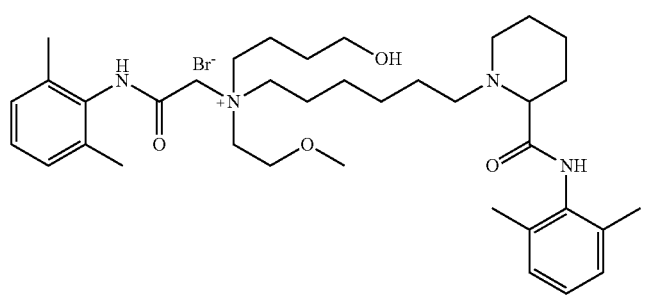
36
HRMS:
$[C_{37}H_{59}N_4O_4]^+$:
623.9021
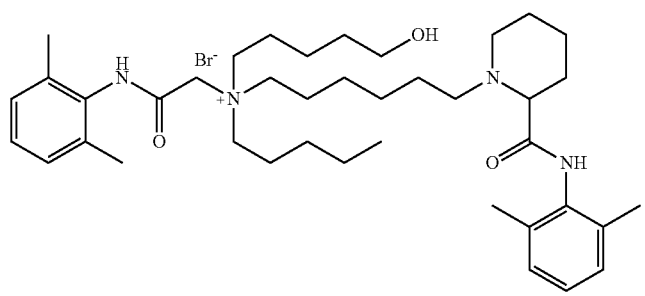
38
HRMS:
$[C_{39}H_{63}N_4O_4]^+$:
651.9566
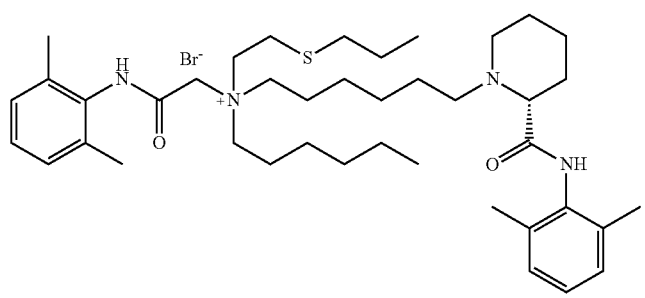
40
HRMS:
$[C_{40}H_{65}N_4O_2]^+$:
666.0441

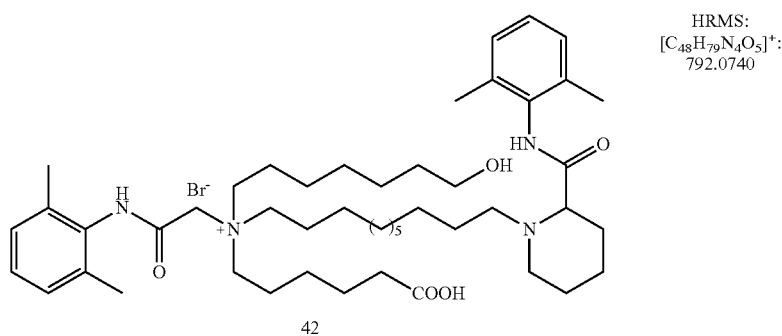
HRMS:
[C₄₈H₇₉N₄O₅]⁺:
792.0740
42
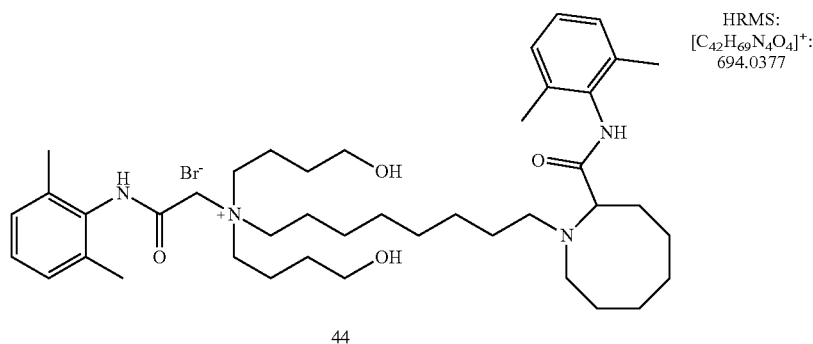
HRMS:
[C₄₂H₆₉N₄O₄]⁺:
694.0377
44
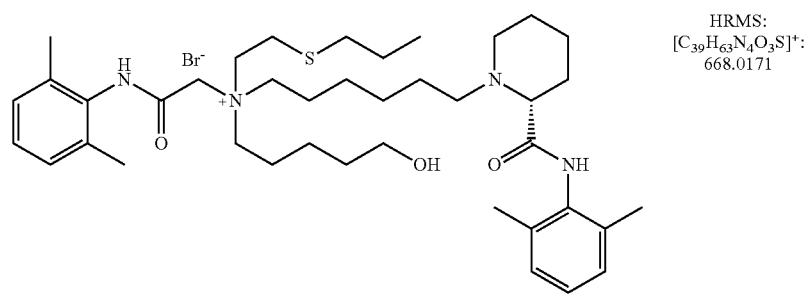
HRMS:
[C₃₉H₆₃N₄O₃S]⁺:
668.0171
46
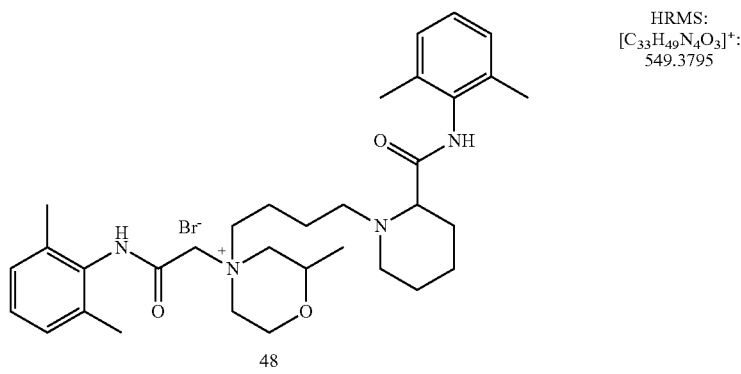
HRMS:
[C₃₃H₄₉N₄O₃]⁺:
549.3795
48

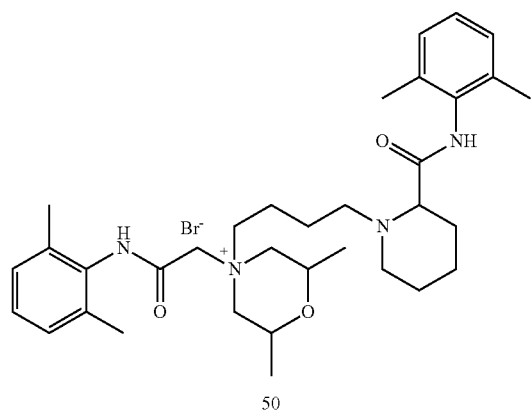
HRMS: $[C_{34}H_{51}N_4O_3]^+$: 563.3959
50
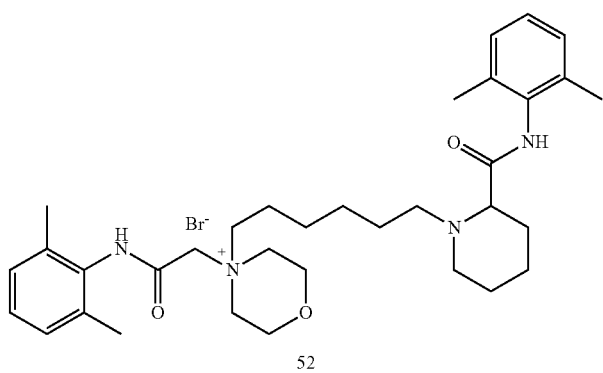
HRMS: $[C_{34}H_{51}N_4O_3]^+$: 563.3953
52
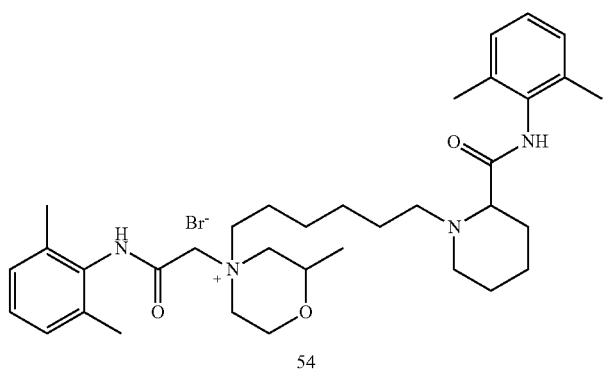
HRMS: $[C_{35}H_{53}N_4O_3]^+$: 577.4116
54
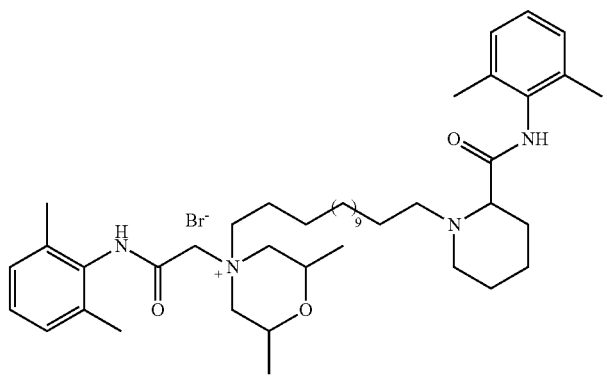
HRMS: $[C_{43}H_{69}N_4O_3]^+$: 689.4112
56

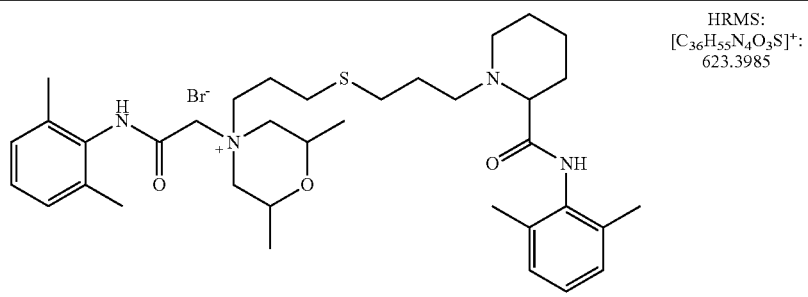
58
HRMS:
$[C_{36}H_{55}N_4O_3S]^+$:
623.3985
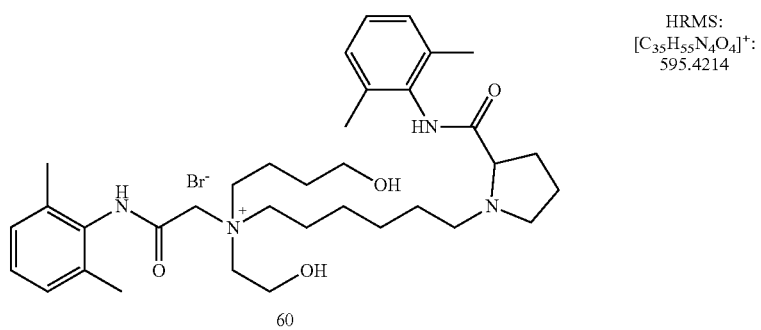
60
HRMS:
$[C_{35}H_{55}N_4O_4]^+$:
595.4214
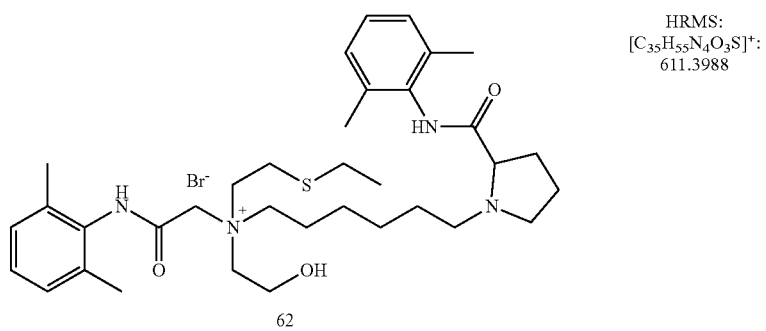
62
HRMS:
$[C_{35}H_{55}N_4O_3S]^+$:
611.3988
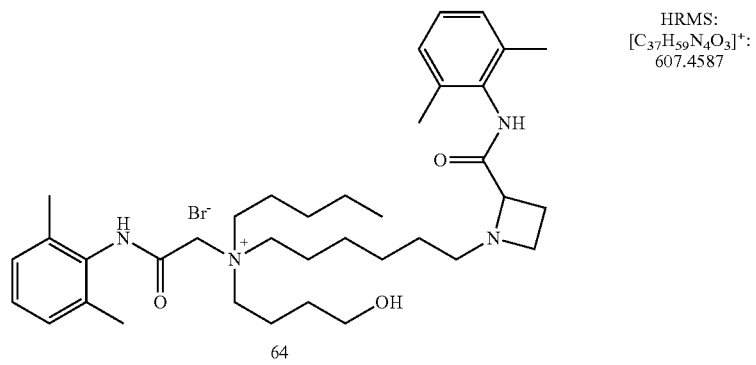
64
HRMS:
$[C_{37}H_{59}N_4O_3]^+$:
607.4587

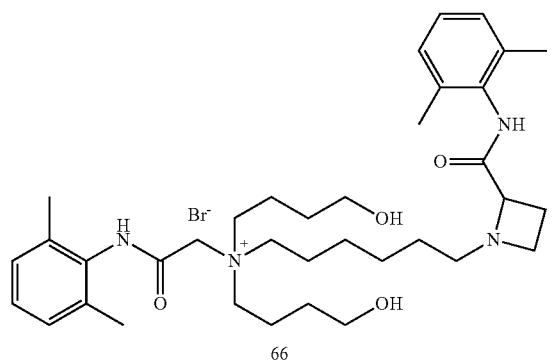
HRMS:
[C₃₆H₅₇N₄O₄]⁺:
609.4377
66
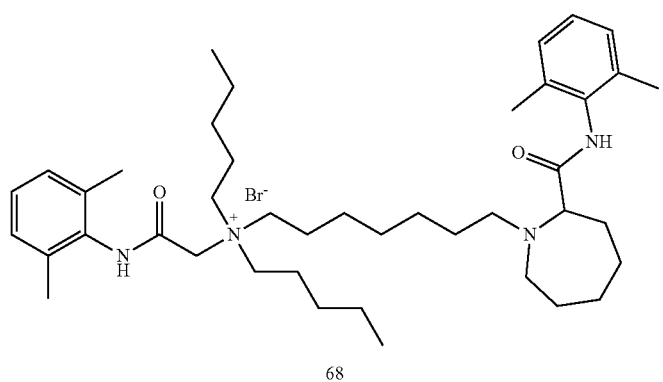
HRMS:
[C₄₂H₆₉N₄O₂]⁺:
661.5411
68
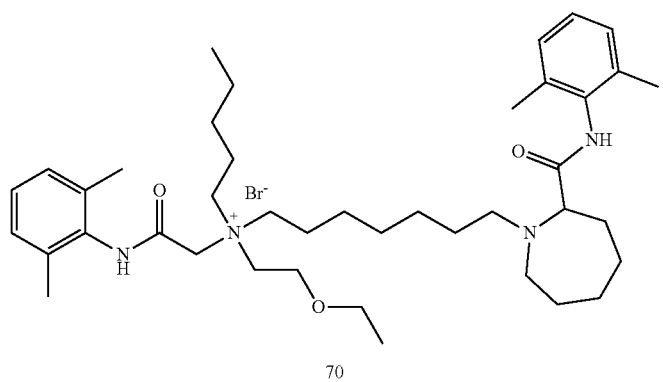
HRMS:
[C₄₁H₆₇N₄O₃]⁺:
663.5213
70
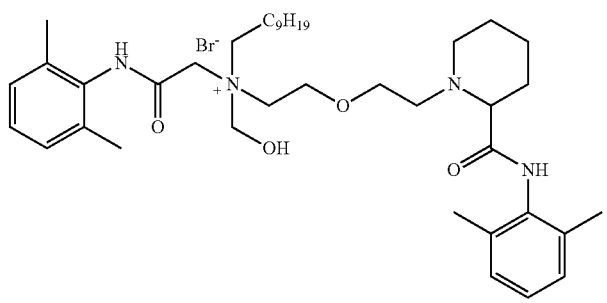
HRMS:
[C₃₉H₆₃N₄O₄]⁺:
651.4840
72

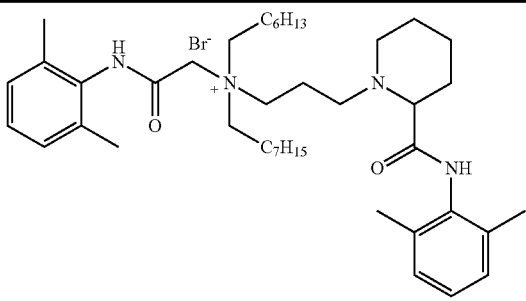

74

HRMS:
$[C_{42}H_{69}N_4O_2]^+$:
661.5418

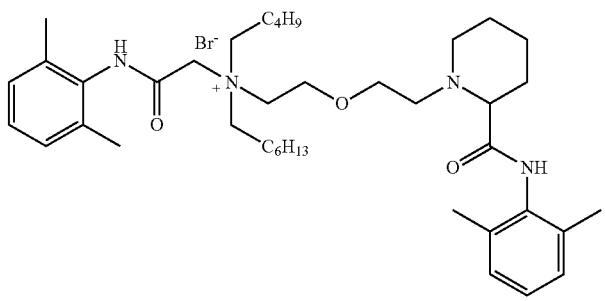

76

HRMS:
$[C_{40}H_{65}N_4O_{43}]^+$:
649.5055

In the following, the beneficial effects of the compound of the present invention are illustrated by experimental examples.

Experimental Example 1. Study on the Local Anesthetic Effect of the Compound of the Present Invention Selected compounds 1-76 prepared in Examples, lidocaine (the positive control group), and levobupivacaine (the positive control group) were respectively assigned SD rats weighing 250-300 g (half male and half female), and the rats were fully adapted to the experimental environment, 8 rats for each group.

Dosage: for lidocaine group, lidocaine was formulated with distilled water into a solution at the concentration of 2% o (74 mmol/L); for levobupivacaine group, levobupivacaine was formulated with distilled water into a solution at the concentration of 0.7500 (22 mmol/L); the compound of the present invention was formulated with distilled water into a solution at the concentration of mmol/mL.

The injection volume for each rat was 0.5 mL, which was guided by a nerve locator and injected near the rat's sciatic nerve. Using von Frey stimulator, the rats were stimulated the soles of the feet in the injected side, to observe the effect of local anesthesia. Meanwhile, Postural Extensor Thrust (PET) was used to evaluate the motor function of the rat: the rat was lifted vertically and the hindlimb in the injected side pedaled on the platform of the electronic balance. At this time, the muscle strength of the rat's hindlimb was displayed by the value on the balance caused by pedal. When the limb was completely paralyzed, the reading was the limb's own weight, about 20 g. If the measured value was more than half of the difference between the baseline and the limb weight, the motor function was regarded as recovery, and if the value was less than or equal to this difference, the motor function was regarded as loss.

TABLE 1

Local anesthetic effect of the compound according to the present invention

| Test drug | Local anesthesia onset time | Duration of sensory block | Duration of motor block |
|---|---|---|---|
| Example 1 product | 3 min | 32 h | 21 h |
| Example 2 product | 4 min | 44 h | 33 h |
| Example 3 product | 4 min | 35 h | 24 h |
| Example 4 product | 7 min | 23 h | 13 h |
| Example 5 product | 4 min | 26 h | 15 h |
| Example 6 product | 1 min | 34 h | 29 h |
| Example 7 product | 5 min | 26 h | 16 h |
| Example 8 product | 4 min | 43 h | 18 h |
| Example 9 product | 4 min | 34 h | 15 h |
| Example 10 product | 3 min | 25 h | 19 h |
| Example 11 product | 5 min | 34 h | 16 h |
| Example 12 product | 5 min | 42 h | 11 h |
| Example 13 product | 4 min | 55 h | 14 h |
| Example 14 product | 5 min | 41 h | 13 h |
| Example 15 product | 5 min | 44 h | 16 h |
| Example 16 product | 5 min | 60 h | 17 h |
| Example 17 product | 5 min | 37 h | 18 h |
| Example 18 product | 2 min | 38 h | 16 h |
| Example 19 product | 5 min | 39 h | 10 h |
| Example 20 product | 5 min | 54 h | 14 h |
| Example 21 product | 5 min | 47 h | 13 h |
| Example 22 product | 3 min | 47 h | 15 h |
| Example 23 product | 5 min | 54 h | 14 h |
| Example 24 product | 4 min | 54 h | 11 h |
| Example 25 product | 5 min | 44 h | 12 h |
| Example 26 product | 5 min | 45 h | 16 h |
| Example 27 product | 3 min | 37 h | 15 h |
| Example 28 product | 2 min | 39 h | 14 h |
| Example 29 product | 5 min | 50 h | 15 h |
| Example 31 product | 5 min | 45 h | 19 h |
| Example 32 product | 2 min | 46 h | 17 h |
| Example 33 product | 5 min | 49 h | 16 h |
| Example 34 product | 5 min | 45 h | 9 h |
| Example 35 product | 2 min | 54 h | 13 h |
| Example 36 product | 5 min | 52 h | 21 h |

TABLE 1-continued

Local anesthetic effect of the compound according to the present invention

| Test drug | Local anesthesia onset time | Duration of sensory block | Duration of motor block |
|---|---|---|---|
| Example 37 product | 1 min | 45 h | 17 h |
| Example 38 product | 1 min | 43 h | 19 h |
| Example 39 product | 3 min | 61 h | 19 h |
| Example 40 product | 2 min | 53 h | 13 h |
| Example 41 product | 2 min | 46 h | 11 h |
| Example 42 product | 5 min | 56 h | 11 h |
| Example 43 product | 5 min | 59 h | 12 h |
| Example 44 product | 5 min | 69 h | 16 h |
| Example 45 product | 3 min | 58 h | 20 h |
| Example 46 product | 5 min | 49 h | 14 h |
| Example 47 product | 3 min | 65 h | 17 h |
| Example 48 product | 5 min | 57 h | 15 h |
| Example 49 product | 4 min | 45 h | 20 h |
| Example 50 product | 5 min | 56 h | 13 h |
| Example 51 product | 5 min | 44 h | 19 h |
| Example 52 product | 2 min | 56 h | 15 h |
| Example 53 product | 5 min | 59 h | 16 h |
| Example 54 product | 5 min | 66 h | 15 h |
| Example 55 product | 1 min | 55 h | 16 h |
| Example 56 product | 1 min | 54 h | 18 h |
| Example 57 product | 5 min | 69 h | 13 h |
| Example 58 product | 3 min | 57 h | 16 h |
| Example 59 product | 1 min | 54 h | 15 h |
| Example 60 product | 1 min | 54 h | 20 h |
| Example 61 product | 3 min | 61 h | 11 h |
| Example 62 product | 5 min | 51 h | 21 h |
| Example 63 product | 3 min | 64 h | 14 h |
| Example 64 product | 3 min | 67 h | 13 h |
| Example 65 product | 5 min | 59 h | 19 h |
| Example 66 product | 1 min | 60 h | 10 h |
| Example 67 product | 1 min | 67 h | 14 h |
| Example 68 product | 1 min | 79 h | 21 h |
| Example 69 product | 1 min | 62 h | 10 h |
| Example 70 product | 2 min | 53 h | 17 h |
| Example 71 product | 1 min | 60 h | 19 h |
| Example 72 product | 1 min | 65 h | 10 h |
| Example 73 product | 3 min | 51 h | 20 h |
| Example 74 product | 1 min | 72 h | 17 h |
| Example 75 product | 1 min | 61 h | 14 h |
| Example 76 product | 3 min | 59 h | 14 h |
| 0.75% levobupivacaine hydrochloride | 1 min | 2.5 h | 2.5 h |
| 2% lidocaine hydrochloride | 1 min | 1 h | 1 h |

Experimental results showed that the compound of the present invention could produce local anesthesia lasting more than 24 h, and the block time of the sensory nerve was significantly longer than that of the motor nerve, and the difference time is greater than or equal to 5 h, wherein most of the compounds have a time difference of greater than or equal to 10 h.

Experimental Example 2. Local Anesthetic Effect of the Compound According to the Present Invention by Subcutaneous Infiltration After the back of SD rat weighing 250-300 g (half female and half male) was shaved and disinfected, a circle with a diameter of about 1.5 cm was drawn on the side of the exposed back, and the circle is divided into 6 equal parts. 0.5 mL solution containing a drug was subcutaneously injected into the skin of the center: using saline as the solvent, 0.75% bupivacaine hydrochloride (22 mmol/L), 2% lidocaine hydrochloride (74 mmol/L), the concentration of compounds 1-76 according to the present invention being 6 mmol/L, 10 rats for each group. Among the Von Frey fiber yarns, the one with a strength of 100 g was bound to the needle for local skin stimulation. One minute After the drug was injected, the above method was used to stimulate in 6 divisions. If no back skin contraction behavior was observed in the same aliquot after three consecutive stimulations, the drug was considered to have positive effect. If back skin contraction was observed, the local anesthetic effect was considered as loss. If four or more areas in 6 aliquots showed positive local anesthesia, the local anesthesia of the drug was considered as effective, while if less than 4 areas in 6 aliquots showed positive, the local anesthesia was considered as failure. Each compound was tested with 10 rats.

TABLE 2

Local anesthetic effect of the compound according the present invention by subcutaneous infiltration.

| Test drug | Local anesthesia onset time (median) | Duration of local anesthesia (median) |
|---|---|---|
| Example 1 product | 1 min | 25 h |
| Example 2 product | 2 min | 44 h |
| Example 3 product | 1 min | 38 h |
| Example 4 product | 1 min | 35 h |
| Example 5 product | 1 min | 56 h |
| Example 6 product | 3 min | 43 h |
| Example 7 product | 1 min | 56 h |
| Example 8 product | 1 min | 43 h |
| Example 9 product | 2 min | 38 h |
| Example 10 product | 1 min | 56 h |
| Example 11 product | 2 min | 39 h |
| Example 12 product | 3 min | 66 h |
| Example 13 product | 4 min | 53 h |
| Example 14 product | 2 min | 75 h |
| Example 15 product | 4 min | 73 h |
| Example 16 product | 2 min | 54 h |
| Example 17 product | 2 min | 56 h |
| Example 18 product | 1 min | 49 h |
| Example 19 product | 1 min | 62 h |
| Example 20 product | 3 min | 47 h |
| Example 21 product | 1 min | 64 h |
| Example 22 product | 2 min | 63 h |
| Example 23 product | 2 min | 83 h |
| Example 24 product | 2 min | 89 h |
| Example 25 product | 3 min | 82 h |
| Example 26 product | 3 min | 92 h |
| Example 27 product | 3 min | 71 h |
| Example 28 product | 3 min | 83 h |
| Example 29 product | 2 min | 73 h |
| Example 31 product | 1 min | 62 h |
| Example 32 product | 2 min | 56 h |
| Example 33 product | 1 min | 89 h |
| Example 34 product | 1 min | 76 h |
| Example 35 product | 2 min | 92 h |
| Example 36 product | 1 min | 81 h |
| Example 37 product | 1 min | 64 h |
| Example 38 product | 3 min | 66 h |
| Example 39 product | 2 min | 89 h |
| Example 40 product | 3 min | 76 h |
| Example 41 product | 3 min | 85 h |
| Example 42 product | 2 min | 73 h |
| Example 43 product | 2 min | 93 h |
| Example 44 product | 2 min | 51 h |
| Example 45 product | 1 min | 89 h |
| Example 46 product | 1 min | 76 h |
| Example 47 product | 1 min | 92 h |
| Example 48 product | 2 min | 73 h |
| Example 49 product | 1 min | 62 h |
| Example 50 product | 2 min | 56 h |
| Example 51 product | 1 min | 89 h |
| Example 52 product | 3 min | 85 h |
| Example 53 product | 1 min | 80 h |
| Example 54 product | 2 min | 69 h |
| Example 55 product | 3 min | 74 h |
| Example 56 product | 1 min | 101 h |
| Example 57 product | 1 min | 85 h |

TABLE 2-continued

Local anesthetic effect of the compound according the present invention by subcutaneous infiltration.

| Test drug | Local anesthesia onset time (median) | Duration of local anesthesia (median) |
|---|---|---|
| Example 58 product | 2 min | 71 h |
| Example 59 product | 1 min | 72 h |
| Example 60 product | 2 min | 66 h |
| Example 61 product | 1 min | 86 h |
| Example 62 product | 1 min | 88 h |
| Example 63 product | 1 min | 79 h |
| Example 64 product | 1 min | 69 h |
| Example 65 product | 1 min | 68 h |
| Example 66 product | 1 min | 87 h |
| Example 67 product | 1 min | 58 h |
| Example 68 product | 3 min | 73 h |
| Example 69 product | 1 min | 80 h |
| Example 70 product | 4 min | 75 h |
| Example 71 product | 1 min | 808 h |
| Example 72 product | 1 min | 72 h |
| Example 73 product | 2 min | 59 h |
| Example 74 product | 1 min | 56 h |
| Example 75 product | 1 min | 58 h |
| Example 76 product | 2 min | 64 h |
| 0.75% levobupivacaine Hydrochloride | 1 min | 7 h |
| 2% lidocaine hydrochloride | 1 min | 4 h |

Experimental results showed that this class of drugs could produce local anesthesia lasting more than 24 hours in the subcutaneous infiltration model of rat, wherein most compounds could produce local anesthesia for more than 40 hours.

Experimental Example 3. Evaluation of Neuropathological Damage of the Compound According to the Present Invention Selected compounds 1-76 prepared in Examples, lidocaine (the positive control group), and levobupivacaine (the positive control group) were respectively assigned SD rats weighing 250-300 g (half male and half female), and the rats were fully adapted to the experimental environment, 8 rats for each group.

Dosage: for lidocaine group, lidocaine was formulated with distilled water into a solution at the concentration of 2% (74 mmol/L); for levobupivacaine group, levobupivacaine was formulated with distilled water into a solution at the concentration of 0.75% (22 mmol/L); the compound of the present invention was formulated with distilled water into a solution at the concentration of mmol/mL.

The injection volume for each rat was 0.5 mL, which was injected near the rat's sciatic nerve. On day 7 and day 14 after injection near the sciatic nerve, the experimental rats were euthanized by injecting bupivacaine into the heart under isoflurane anesthesia. About 1.5 cm sciatic nerve was collected at the injection site, stored in 10% formaldehyde solution for 48 hours, stained with HE, and cut into slices with 5 m thickness.

Dosage: for lidocaine group, lidocaine was formulated with distilled water into a solution at the concentration of 2% (74 mmol/L); for levobupivacaine group, levobupivacaine was formulated with distilled water into a solution at the concentration of 0.75% (22 mmol/L); the compound of the present invention was formulated with distilled water into a solution at the concentration of 6 mmol/mL.

The injection volume for each rat was 0.5 mL, which was injected under the skin of the back of the rat. On day 7 and day 14 after subcutaneous injection, the experimental rats were euthanized by injecting bupivacaine into the heart under isoflurane anesthesia. The skin tissue at the injection site was collected, stored in 10% formaldehyde solution for 48 hours, stained with HE, and cut into slices with 5 m thickness.

The evaluation of neuropathological damage showed that compared with the lidocaine positive control group and the levobupivacaine positive control group, compounds of Examples did not show significant differences in the aspects of nerve injury, vascular proliferation, demyelination, muscle inflammation, and connective tissue inflammation, and thus had good safety.

In summary, the present invention provided a new class of quaternary ammonium compounds with novel structures, as well as the preparative method and the use thereof. The compound had a fast onset of action and a long-time local anesthetic effect (more than 24 hours, and the local anesthesia time of most compounds exceeding 40 hours) after a single administration. The compound was selective for nerve block (the block time of sensory nerve was longer than that of motor nerve, and the difference time was greater than or equal to 5 hours, moreover, the difference time of most compounds was more than 10 hours), and had both long-acting and selective local anesthetic effect, that significantly reduced the side effects of QX314, QX314 composition, and the quaternary ammonium compound with surfactant structure characteristics, with better safety. That is, the compound of the present invention and its pharmaceutically acceptable salts could be used to prepare safe drugs with long-acting and selective local anesthesia, which had the advantages of long-time local anesthetic action, good nerve-selectivity

The invention claimed is:

1. A compound of formula I, or a pharmaceutically acceptable salt thereof, or a stereoisomer thereof, or a solvate thereof,

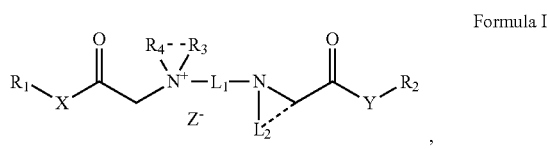

Formula I wherein,
each of X and Y is independently selected from O and $NR_{10}$, wherein $R_{10}$ is selected from H, deuterium, and $C_1$-$C_4$ alkyl;
$Z^-$ is a pharmaceutically acceptable anion;
$R_1$ is selected from $n_1$ $R_{11}$-substituted aryls; and
$R_2$ is selected from $n_1'$ $R_{11}'$-substituted aryls;
wherein,
$n_1$ and $n_1'$ are each independently selected from an integer of 0 to 5, and $R_{11}$ and $R_{11}'$ are each independently selected from deuterium, $C_1$-$C_4$ alkyl, $C_1$-$C_4$ alkoxy, halogen, nitro, cyano, hydroxyl, carboxyl, and amino;
when the dotted line between $R_3$ and $R_4$ in Formula I is none, $R_3$ is selected from substituted $C_1$-$C_{10}$ alkyl and unsubstituted $C_5$-$C_{10}$ alkyl, and $R_4$ is a substituted or unsubstituted $C_1$-$C_{10}$ alkyl, wherein said substituted $C_1$-$C_{10}$ alkyl or said substituted $C_1$-$C_4$ alkoxy is substituted with one or more substituent selected from deuterium, $C_1$-$C_4$ alkoxy substituted with hydroxyl, unsubstituted $C_1$-$C_4$ alkoxy, halogen, nitro, cyano, hydroxyl, carboxy, amino, ester, $C_1$-$C_6$ alkylthio, and mercapto;

when the dotted line between $R_3$ and $R_4$ in formula I is a bond, $R_3$ and $R_4$ are independently selected from $C_1$-$C_4$ alkylenes that are unsubstituted or substituted with one or more substituent selected from $C_1$-$C_3$ alkyls, the main chain of each of the $C_1$-$C_4$ alkylenes contains 0 to 4 heteroatoms selected from O, S, and $NR_{12}$, wherein said $R_{12}$ is selected from hydrogen, deuterium, and $C_1$-$C_4$ alkyls;

$L_1$ is selected from $C_1$-$C_{14}$ alkylenes that are unsubstituted or substituted with one or more substituent selected from deuterium, $C_1$-$C_4$ alkyls, $C_1$-$C_4$ alkoxys, and halogen; wherein the main chain of each of the $C_1$-$C_{14}$ alkylenes contains 0 to 4 heteroatoms selected from O, S, and $NR_{12}$, wherein said $R_{12}$ is selected from the group hydrogen, deuterium, $C_1$-$C_4$ alkyls, and $C_1$-$C_4$ alkoxys; and the dotted line connected to $L_2$ is a bond, and $L_2$ is selected from $C_1$-$C_8$ alkylenes that are unsubstituted or substituted with one or more substituent selected from deuterium, $C_1$-$C_4$ alkyls, $C_1$-$C_4$ alkoxys, and halogen.

2. The compound according to claim 1, or a pharmaceutically acceptable salt thereof, or a stereoisomer thereof, or a solvate thereof, wherein:

each of X and Y is independently selected from NH and $NCH_3$;

$Z^-$ is $Br^-$, $Cl^-$, or sulfonate;

$R_1$ is selected from $n_1$ $R_{11}$-substituted aryls;

$R_2$ is selected from $n_1'$ $R_{11}'$-substituted aryls;

wherein, each of $n_1$ and $n_1'$ is independently selected from an integer of 0 to 5, and each of $R_{11}$ and $R_{11}'$ is independently selected from deuterium, $C_1$-$C_4$ alkyl, $C_1$-$C_4$ alkoxy, halogen, nitro, cyano, and hydroxyl;

when the dotted line between $R_3$ and $R_4$ in Formula I is none, $R_3$ is selected from substituted $C_1$-$C_{10}$ alkyl and unsubstituted $C_5$-$C_{10}$ alkyl, and $R_4$ is a substituted or unsubstituted $C_1$-$C_{10}$ alkyl, wherein said substituted $C_1$-$C_{10}$ alkyl or said substituted $C_1$-$C_4$ alkoxy is substituted with one or more substituent selected from deuterium, $C_1$-$C_4$ alkoxy substituted with hydroxyl, unsubstituted $C_1$-$C_4$ alkoxy, hydroxyl, carboxy, $C_2$-$C_5$ alkylthio, and mercapto;

when the dotted line between $R_3$ and $R_4$ in formula I is a bond, $R_3$ and $R_4$ are independently selected from $C_1$-$C_4$ alkylenes, wherein the main chain of each of the $C_1$-$C_4$ alkylenes contains 0 to 2 heteroatoms, and the heteroatom is O;

$L_1$ is selected from $C_3$-$C_{14}$ alkylenes that are unsubstituted or substituted with one or more alkyl, and the main chain of each of the $C_3$-$C_{14}$ alkylenes contains 0-2 heteroatoms is selected from O and S; and the dotted line connected to $L_2$ is a bond, and $L_2$ is selected from $C_1$-$C_6$ alkylenes.

3. The compound according to claim 1, or a pharmaceutically acceptable salt thereof, or a stereoisomer thereof, or a solvate thereof, wherein:

each of X and Y is independently selected from NH or $NCH_3$;

$Z^-$ is $Br^-$, $Cl^-$, or sulfonate;

$R_1$ is selected from $n_1$ $R_{11}$-substituted aryls;

$R_2$ is selected from $n_1'$ $R_{11}'$-substituted aryls;

wherein, each of $n_1$ and $n_1'$ is 2 or 3, $R_{11}$ and $R_{11}'$ are independently selected from methyl, propyl, methoxy, hydroxy, nitro, cyano, and halogen;

when the dotted line between $R_3$ and $R_4$ in Formula I is none, $R_3$ is selected from substituted $C_1$-$C_8$ alkyl or unsubstituted $C_5$-$C_{10}$ alkyl, and $R_4$ is selected from substituted or unsubstituted $C_1$-$C_{10}$ alkyl, and the substituted $C_1$-$C_8$ alkyl or the substituted $C_1$-$C_{10}$ alkyl is substituted with one or more substituent selected from deuterium, $C_1$-$C_3$ alkoxy substituted with hydroxyl, unsubstituted $C_1$-$C_3$ alkoxy, hydroxyl, carboxy, $C_2$-$C_5$ alkylthio, and mercapto;

when the dotted line between $R_3$ and $R_4$ in formula I is a bond, $R_3$ and $R_4$ are independently selected from $C_2$-$C_3$ alkylenes that are substituted with $C_1$ alkyl or unsubstituted and the main chain of each of the $C_2$-$C_3$ alkylenes contains no heteroatom or one heteroatom, and the heteroatom is O;

$L_1$ is selected from unsubstituted $C_3$-$C_{14}$ alkylenes; wherein the main chain of each of the $C_3$-$C_{14}$ alkylenes contains 0 to 2 heteroatoms selected from O and S; and the dotted line connected to $L_2$ is a bond, and $L_2$ is selected from unsubstituted $C_1$-$C_6$ alkylenes.

4. The compound according to claim 1, or a pharmaceutically acceptable salt thereof, or a stereoisomer thereof, or a solvate thereof, wherein:

each of X and Y is NH;

$Z^-$ is $Br^-$;

$R_1$ is selected from $n_1$ $R_{11}$-substituted aryls;

$R_2$ is selected from $n_1'$ $R_{11}'$-substituted aryls;

wherein, each of $n_1$ and $n_1'$ is 2 or 3, and $R_{11}$ and $R_{11}'$ are methyl;

when the dotted line between $R_3$ and $R_4$ in Formula I is none, $R_3$ is selected from unsubstituted $C_5$-$C_{10}$ alkyl, and $C_1$-$C_8$ alkyl substituted with deuterium, unsubstituted $C_1$-$C_3$ alkoxy, $C_1$-$C_3$ alkoxy with hydroxyl, hydroxyl, carboxy, $C_2$-$C_3$ alkylthio, and mercapto;

when the dotted line between $R_3$ and $R_4$ in formula I is a bond, $R_3$ and $R_4$ are independently selected from unsubstituted $C_2$-$C_3$ alkylenes, the main chain of the $C_2$-$C_3$ alkylenes contains one oxygen atom;

$L_1$ is selected from unsubstituted $C_3$-$C_{14}$ alkylenes; wherein the main chain of each of the unsubstituted $C_3$-$C_{14}$ alkylenes contains one heteroatom selected from O and S; and the dotted line connected to $L_2$ is a bond, and $L_2$ is selected from unsubstituted $C_2$-$C_6$ alkylenes.

5. The compound according to claim 1, or a pharmaceutically acceptable salt thereof, or a stereoisomer thereof, or a solvate thereof, wherein said compound is of formula II:

Formula II

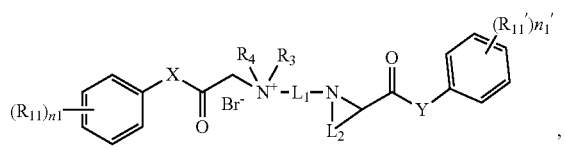

wherein, each of X and Y is independently selected from NH and $NCH_3$;

each of $n_1$ and $n_1'$ is independently 2 or 3, $R_{11}$ and $R_{11}'$ are independently selected from methyl, propyl, methoxy, hydroxy, nitro, cyano, and halogen;

R₃ is selected from substituted $C_1$-$C_8$ alkyl or unsubstituted $C_5$-$C_{10}$ alkyl; R₄ is selected from substituted or unsubstituted $C_1$-$C_{10}$ alkyl; the substituted $C_1$-$C_8$ alkyl and the substituted $C_1$-$C_{10}$ alkyl are substituted with one or more substituent selected from deuterium, $C_1$-$C_3$ alkoxy substituted with hydroxyl, unsubstituted $C_1$-$C_3$ alkoxy, hydroxyl, carboxy, $C_2$-$C_5$ alkylthio, and mercapto; and $L_1$ is selected from unsubstituted $C_3$-$C_{14}$ alkylenes; wherein the main chain of each of the unsubstituted $C_3$-$C_{14}$ alkylenes contains 0, 1 or 2 heteroatoms selected from O and S; and $L_2$ is selected from unsubstituted $C_2$-$C_6$ alkylenes.

6. The compound according to claim 5, or a pharmaceutically acceptable salt thereof, or a stereoisomer thereof, or a solvate thereof, wherein said compound is of formula III:

Formula III

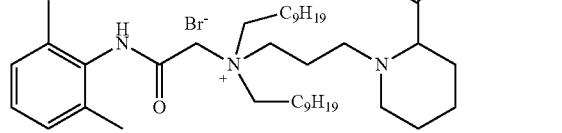

wherein,
R₃ is selected from $C_1$-$C_5$ alkyl substituted with hydroxyl;
R₄ is selected from substituted or unsubstituted $C_1$-$C_5$ alkyl;

$L_1$ is selected from unsubstituted $C_3$-$C_6$ alkylenes; and
$L_2$ is selected from unsubstituted $C_4$ alkylenes.

7. The compound according to claim 1, or a pharmaceutically acceptable salt thereof, or a stereoisomer thereof, or a solvate thereof, characterized in that said compound is as shown in formula IV:

Formula IV

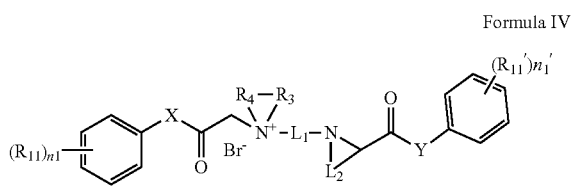

wherein,
each of X and Y is NH;
each of $n_1$ and $n_1'$ is 2 or 3;
$R_{11}$ and $R_{11}'$ are methyl;
R₃ and R₄ are independently selected from $C_2$-$C_3$ alkylenes that are unsubstituted or substituted with $C_1$ alkyl and each of the $C_2$-$C_3$ alkylenes has a main chain containing one oxygen atom;
$L_1$ is selected from unsubstituted $C_3$-$C_{14}$ alkylenes, each having a main chain containing 0 or 1 heteroatom selected from O and S; and
$L_2$ is selected from unsubstituted $C_2$-$C_6$ alkylenes.

8. The compound according to claim 1, or a pharmaceutically acceptable salt thereof, or a stereoisomer thereof, or a solvate thereof, wherein the compound is one of the followings:

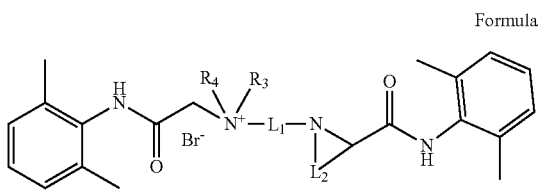

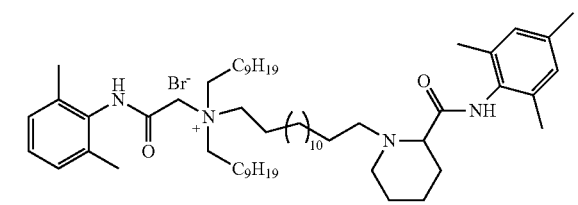

1

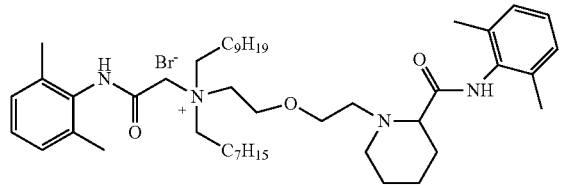

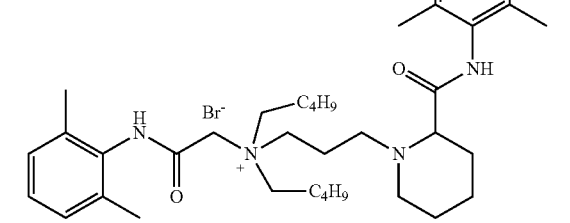

2

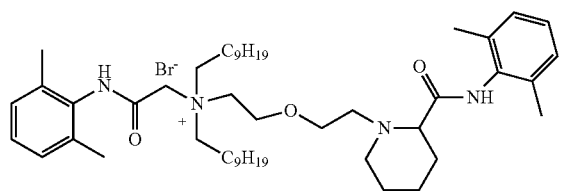

3

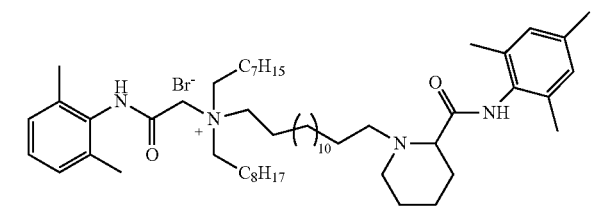

-continued
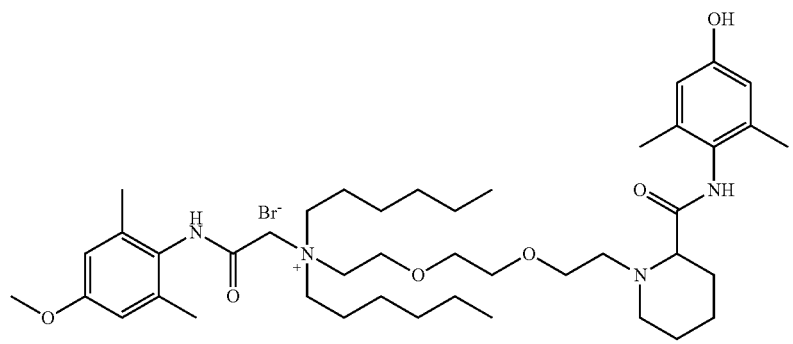
4
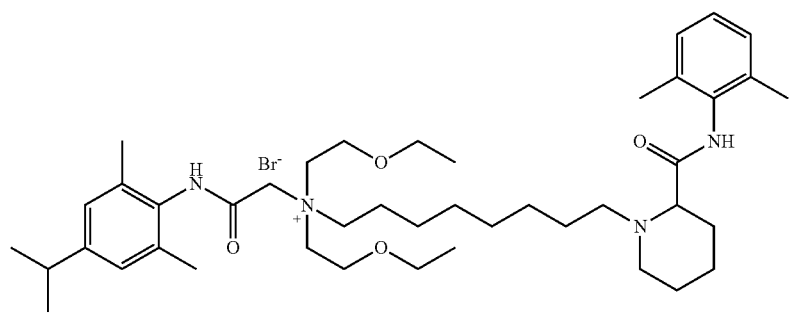
5
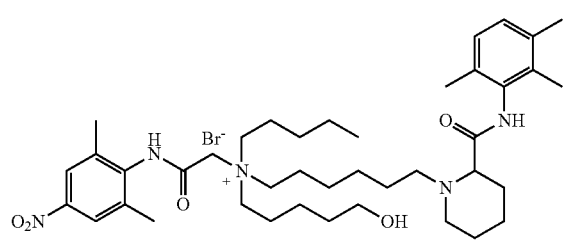
6
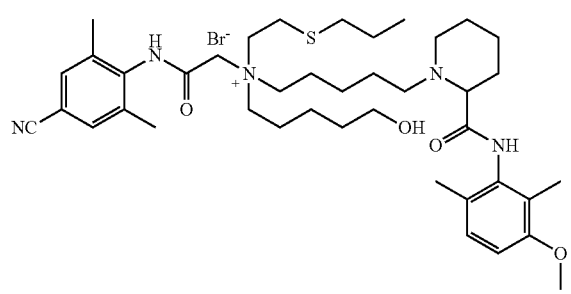
7
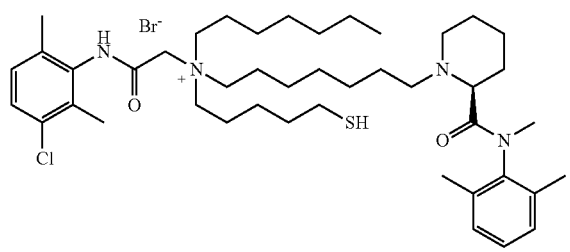
8
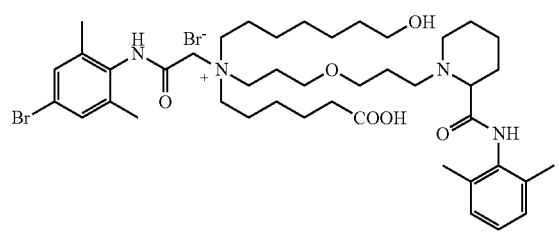
9
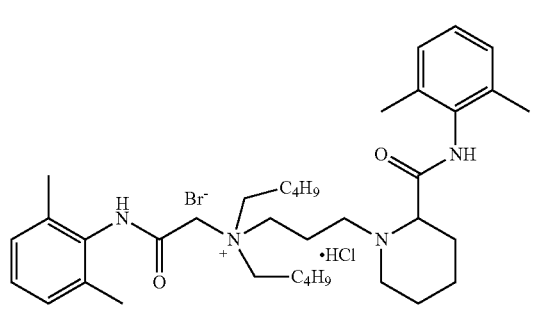
10
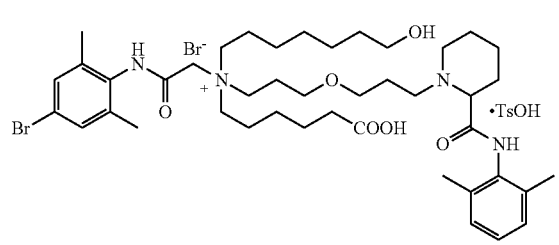
11

-continued
12
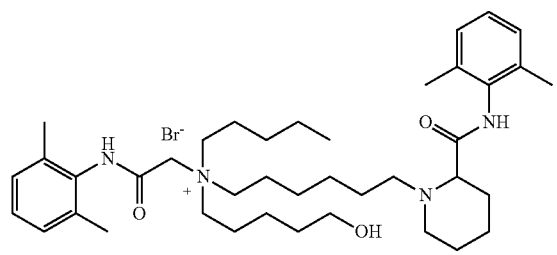
13
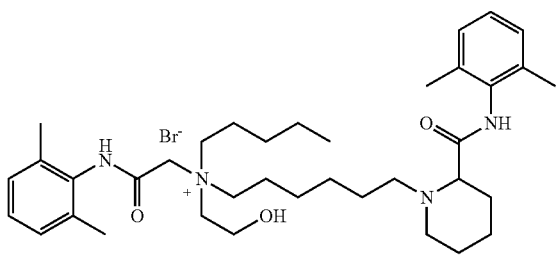
14
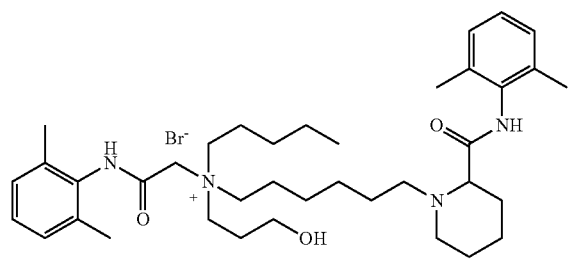
15
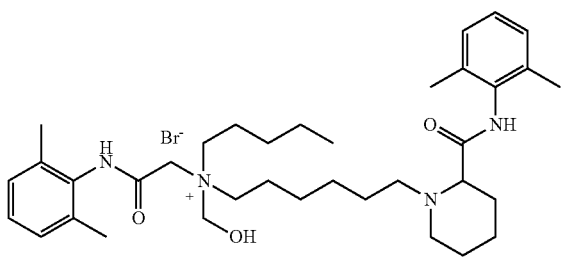
16
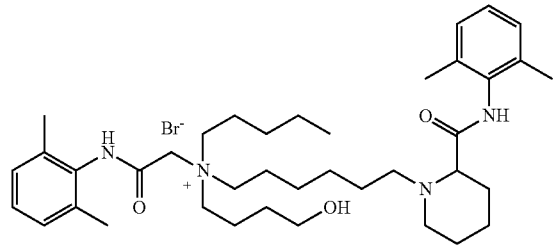
17
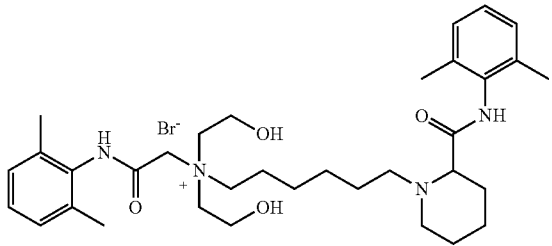
18
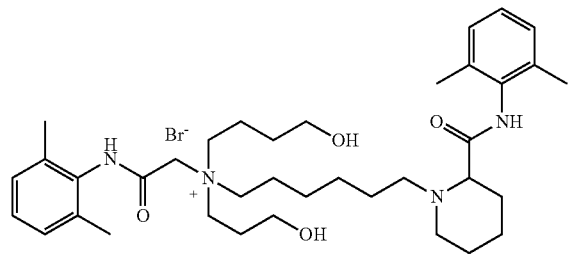
19
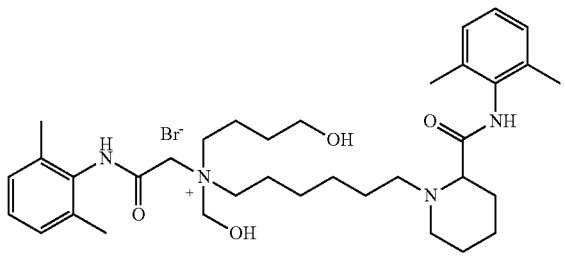
20
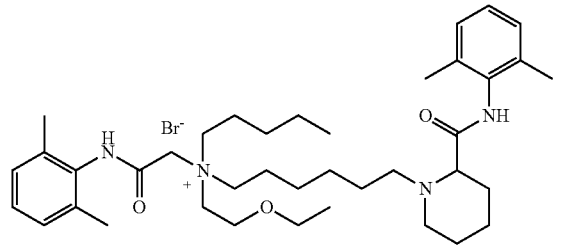
21
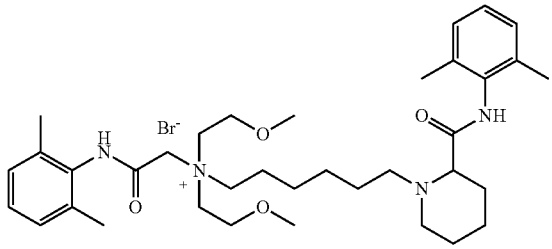
22
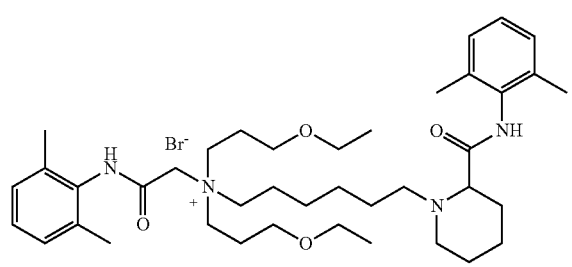
23
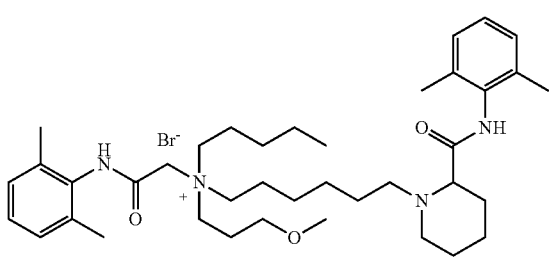

-continued
24
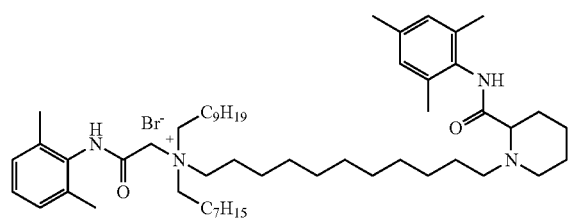
25
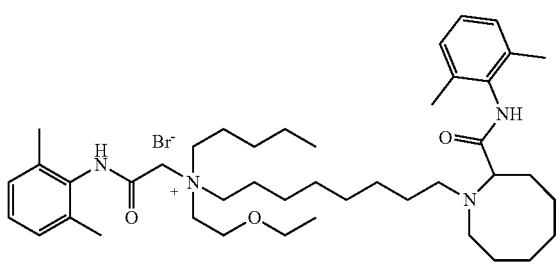
26
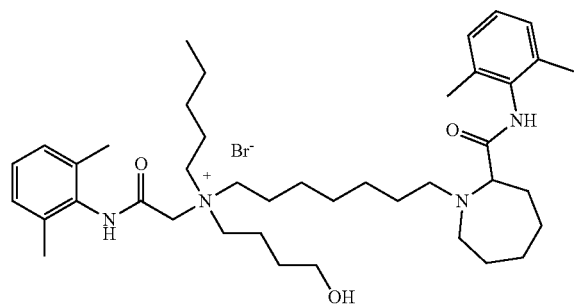
27
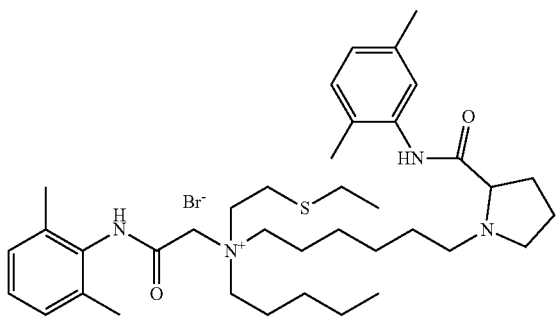
28
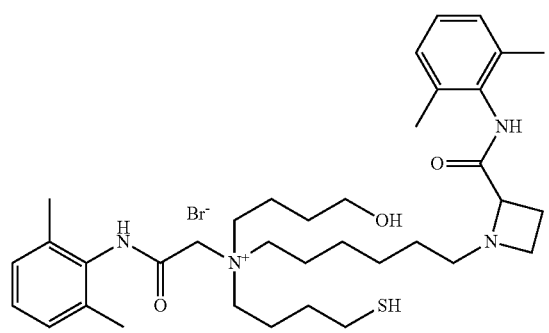
29
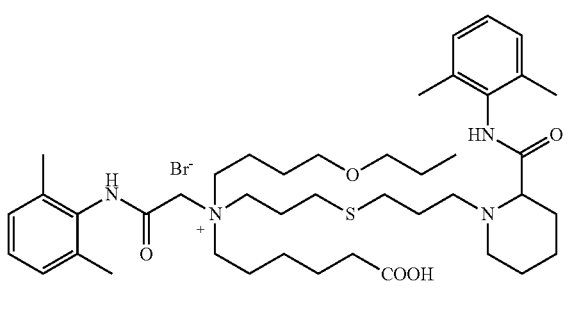
30
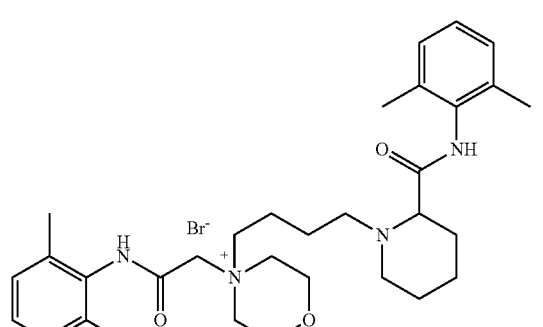
31
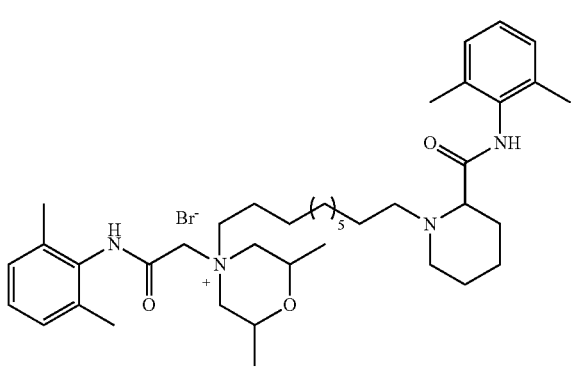
32
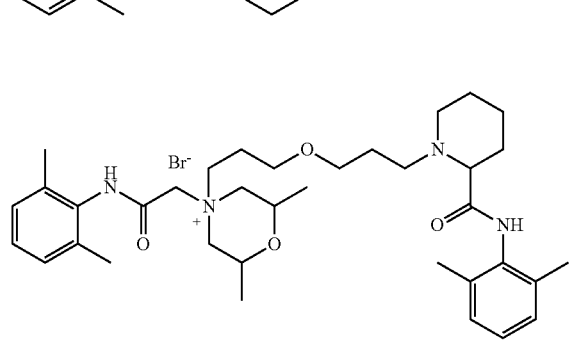
35
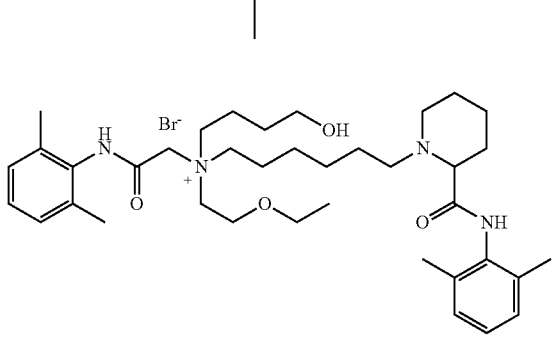

36
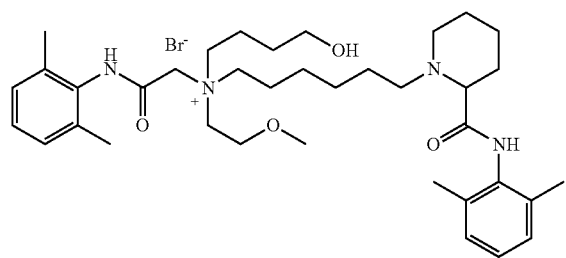
37
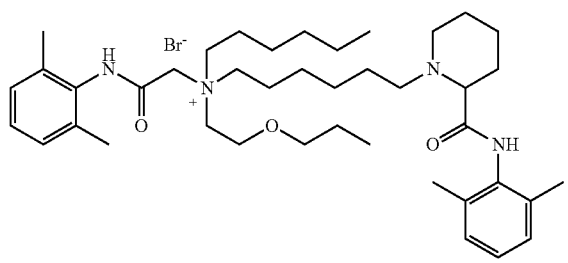
38
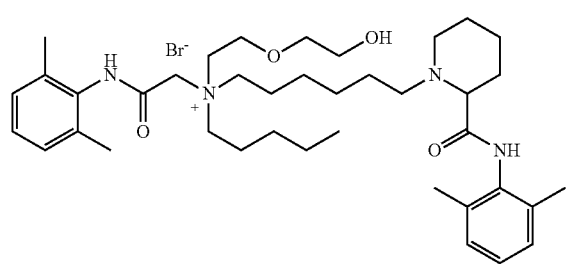
39
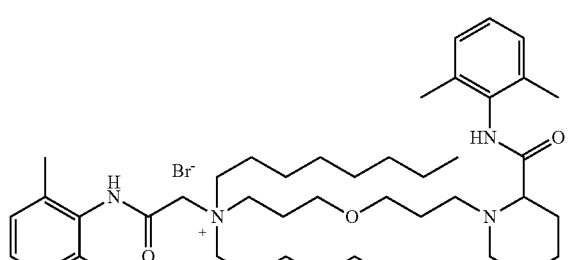
40
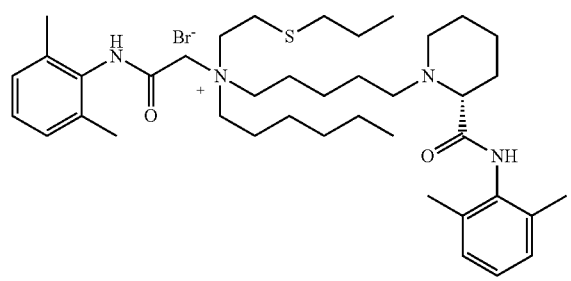
41
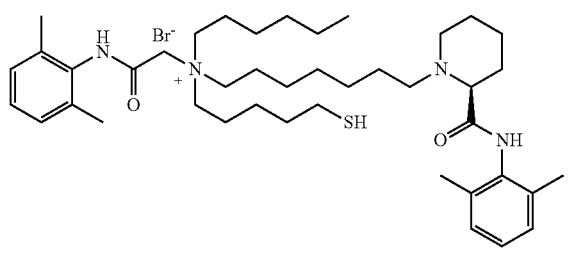
42
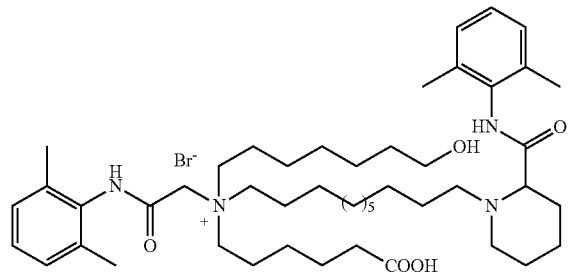
43
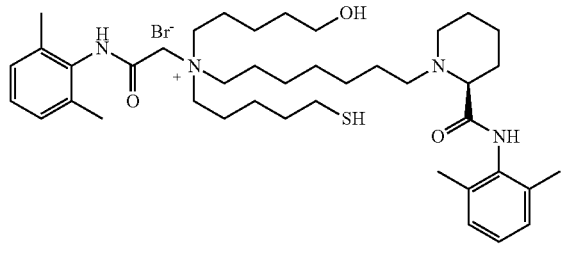
44
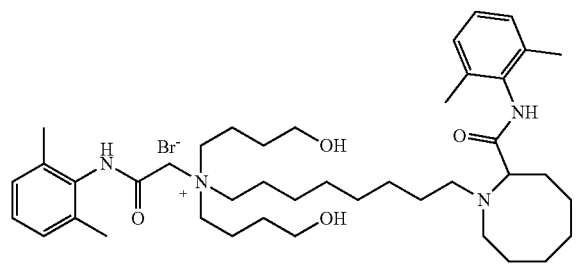
45
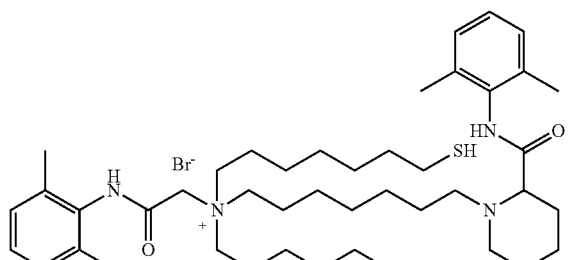

-continued
46
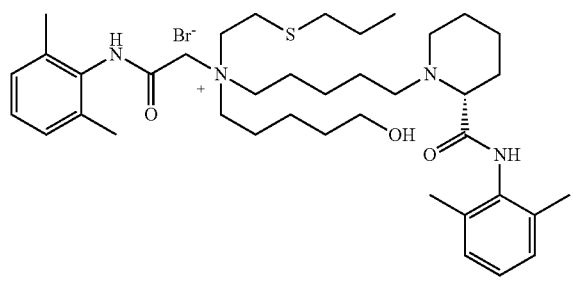
47
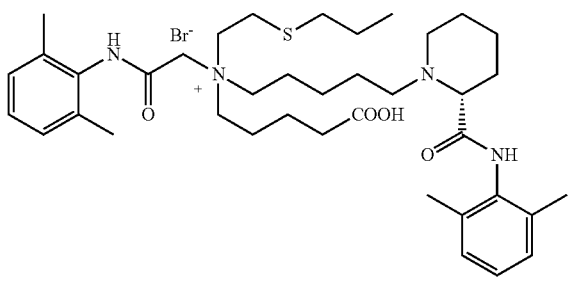
48
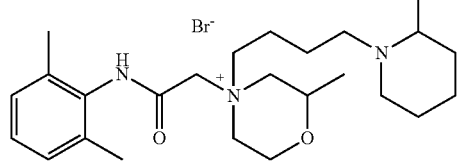
49
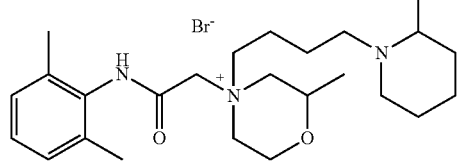
50
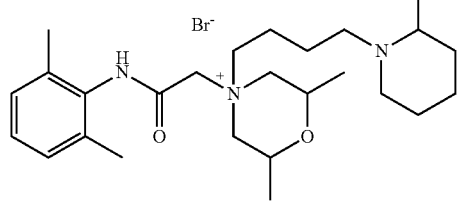
51
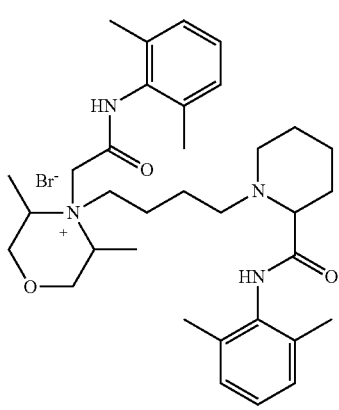
52
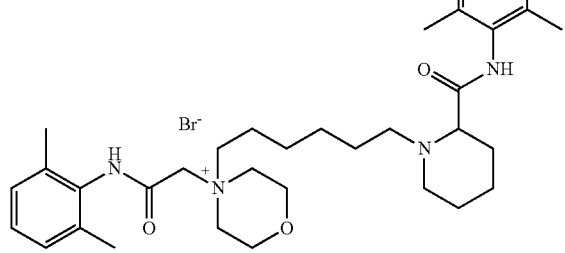
53
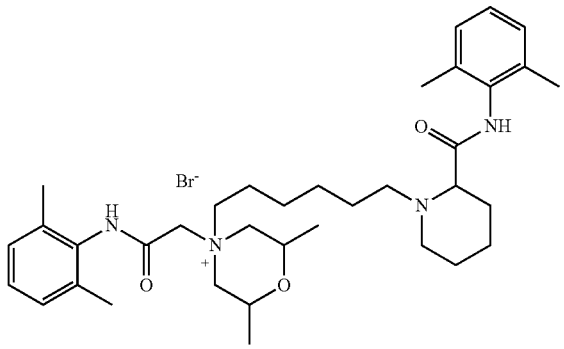

-continued
54
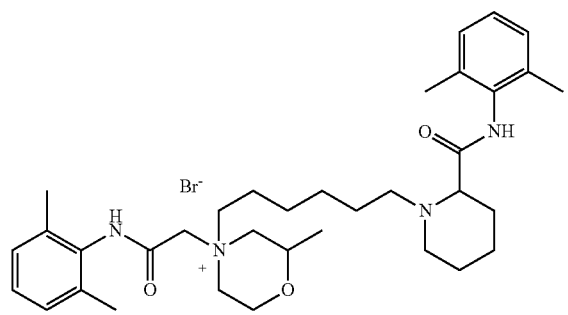
55
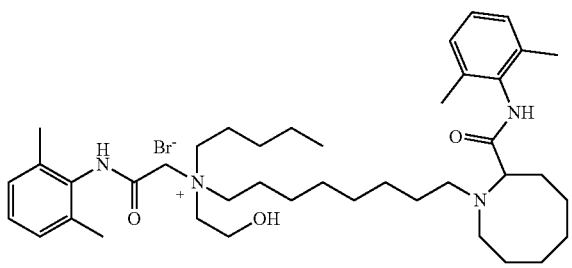
56
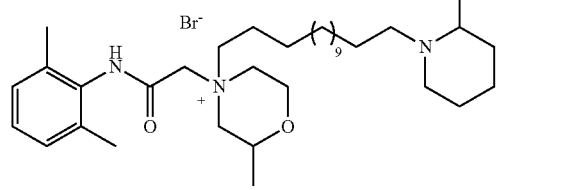
57
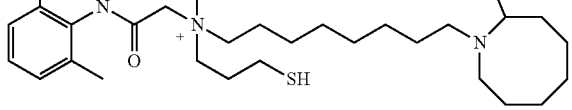
58
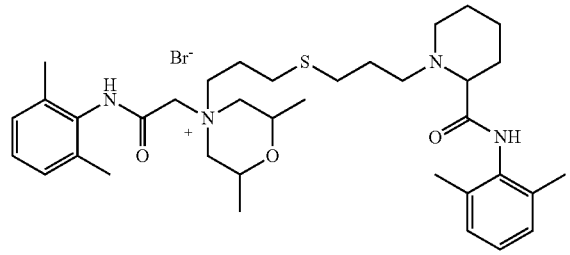
59
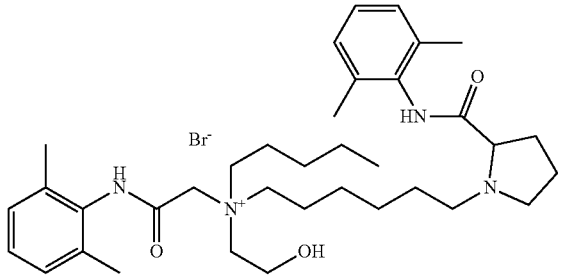
60
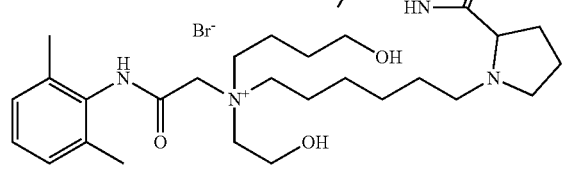
61
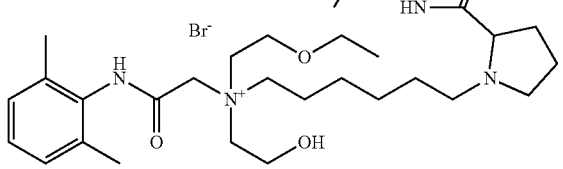
62
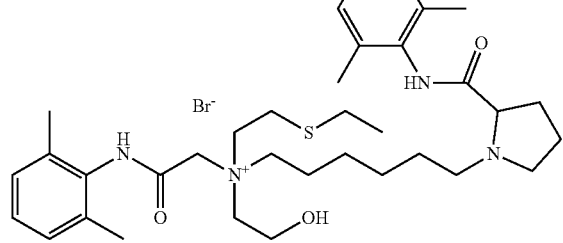
63
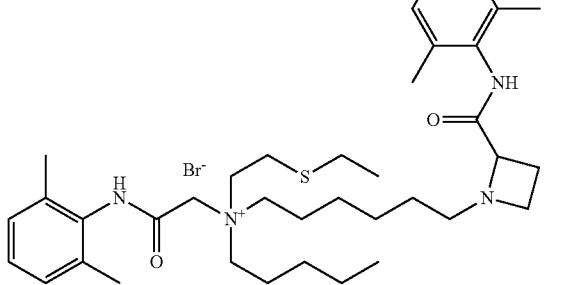

-continued
64
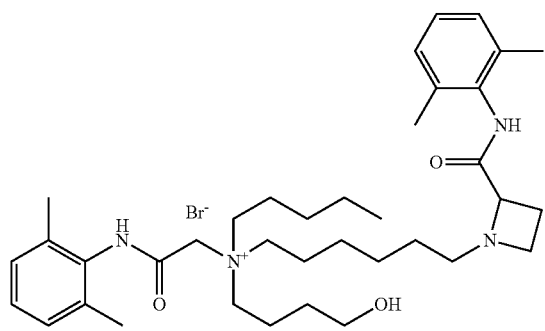
65
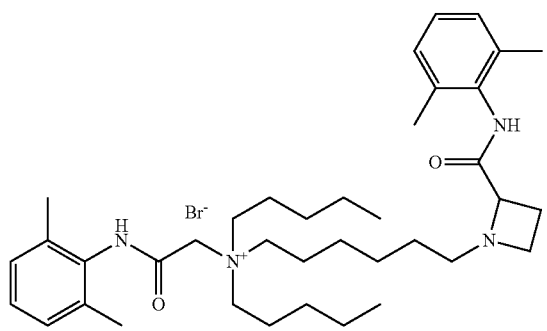
66
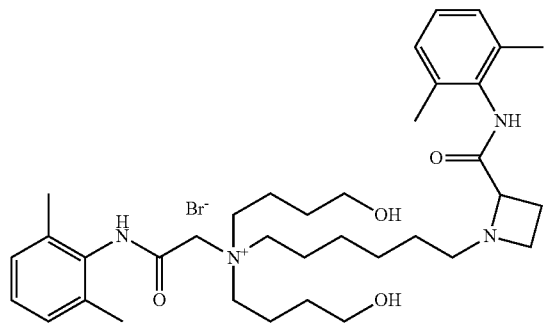
67
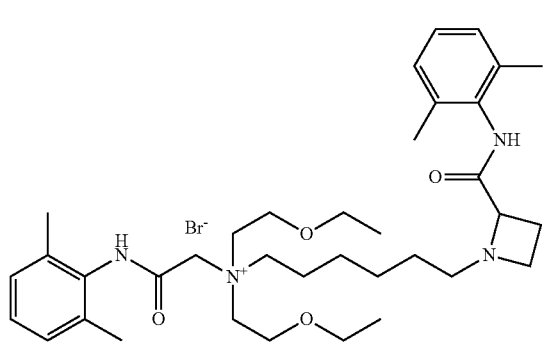
68
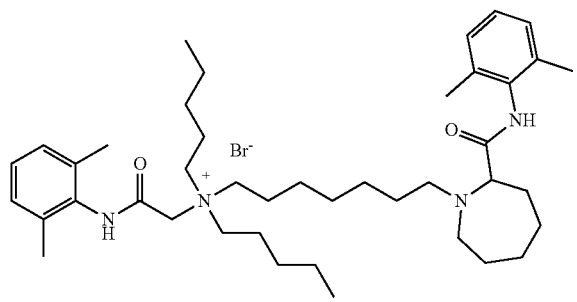
69
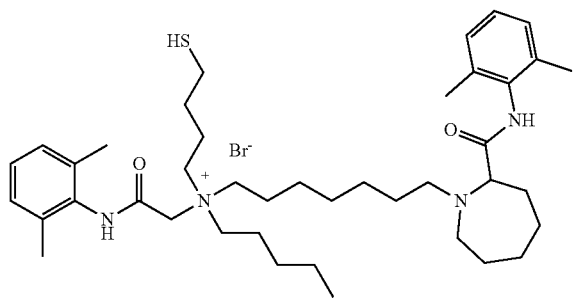
70
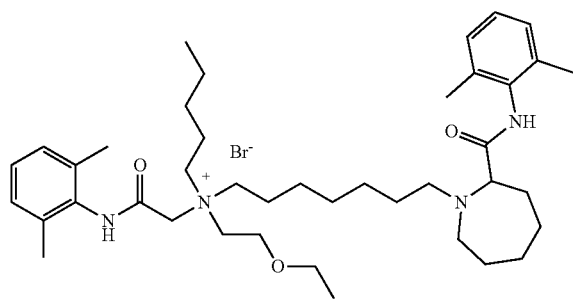
71
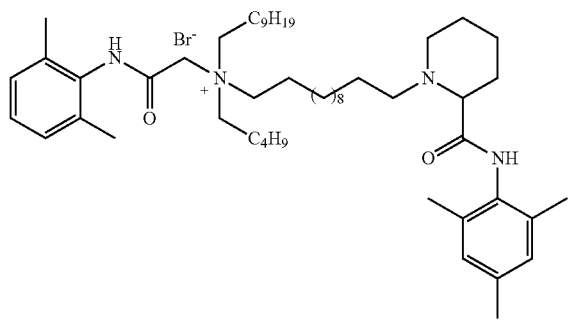
73
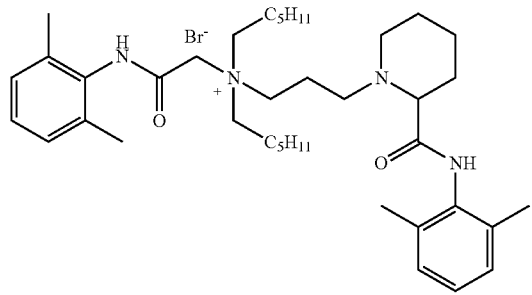
74
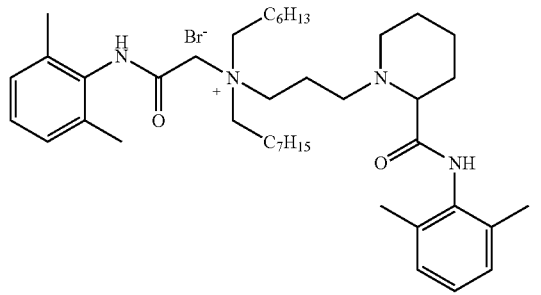

75

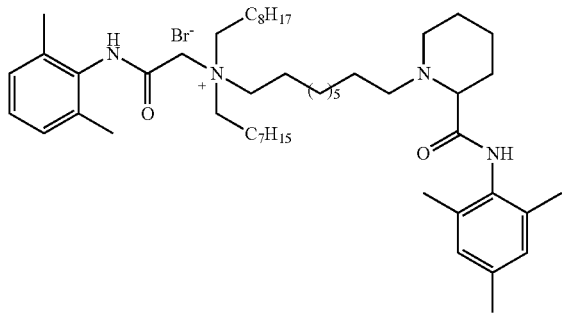

76

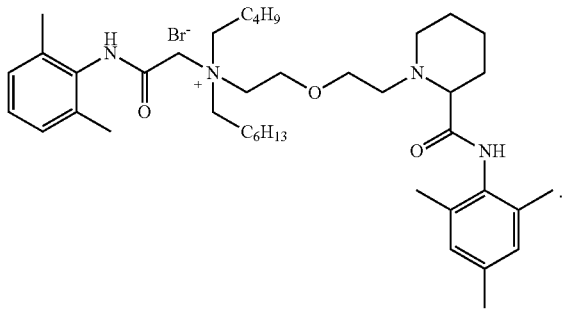

9. A method for local anesthesia, comprising administering to a subject in need thereof a preparation comprising the compound according to claim 1, or a pharmaceutically acceptable salt thereof, or a stereoisomer thereof, or a solvate thereof, together with a pharmaceutically acceptable carrier.

10. The method according to claim 9, wherein said local anesthetic medicine makes a block time of sensory nerve longer than a block time of motor nerve; and/or said local anesthesia is long-acting local anesthesia.

11. A drug preparation formed by the compound according to claim 1, or a pharmaceutically acceptable salt thereof, or a stereoisomer thereof, or a solvate thereof, with the addition of pharmaceutically acceptable excipients.

12. The method according to claim 10, wherein the local anesthesia has an anesthesia time exceeding 24 hours.

* * * * *